(12) United States Patent
Betzig et al.

(10) Patent No.: US 9,500,846 B2
(45) Date of Patent: Nov. 22, 2016

(54) RAPID ADAPTIVE OPTICAL MICROSCOPY OVER LARGE MULTICELLULAR VOLUMES

(71) Applicant: Howard Hughes Medical Institute, Ashburn, VA (US)

(72) Inventors: Robert E. Betzig, Ashburn, VA (US); Kai Wang, Asbhurn, VA (US)

(73) Assignee: Howard Hughes Medical Institute, Ashburn, VA (US)

(*) Notice: Subject to any disclaimer, the term of this patent is extended or adjusted under 35 U.S.C. 154(b) by 2 days.

(21) Appl. No.: 14/660,906

(22) Filed: Mar. 17, 2015

(65) Prior Publication Data

US 2015/0362713 A1    Dec. 17, 2015

Related U.S. Application Data

(60) Provisional application No. 61/954,236, filed on Mar. 17, 2014, provisional application No. 61/979,482, filed on Apr. 14, 2014.

(51) Int. Cl.
| | |
|---|---|
| *F21V 9/16* | (2006.01) |
| *G01J 1/58* | (2006.01) |
| *G02B 21/00* | (2006.01) |
| *G02B 21/36* | (2006.01) |
| *G01N 21/64* | (2006.01) |

(52) U.S. Cl.
CPC ....... *G02B 21/0064* (2013.01); *G01N 21/6458* (2013.01); *G02B 21/006* (2013.01); *G02B 21/008* (2013.01); *G02B 21/0056* (2013.01); *G02B 21/0072* (2013.01); *G02B 21/0076* (2013.01); *G02B 21/361* (2013.01); *G01N 2021/6419* (2013.01); *G01N 2201/0675* (2013.01)

(58) Field of Classification Search
CPC .............................. G01N 21/66; G01N 21/36
USPC ...................................................... 250/458.1
See application file for complete search history.

(56) References Cited

PUBLICATIONS

Wang et al. "Rapid adaptive optical recovery of optimal resolution over large volumes", Nature Methods 11, 625-628, Jun. 2014.*

* cited by examiner

*Primary Examiner* — Yara B Green
*Assistant Examiner* — Meenakshi Sahu
(74) *Attorney, Agent, or Firm* — Brake Hughes Bellermann LLP

(57) ABSTRACT

Excitation light is focused to a focus within a sample and the focus is scanned within a volume in the sample with scanning optical elements. Signal light emitted from the focus is de-scanned, with the one or more scanning optical elements, onto a wavefront sensor as the focus is scanned within the volume. Based on the descanned signal light, an average aberration created by the volume of the sample of a wavefront of the excitation light is determined. A wavefront of the excitation light is corrected by an amount according to the determined average aberration while the focus is scanned within the volume, the signal light is imaged onto a photosensitive detector as the focus is scanned within the volume, and a wavefront of the imaged signal light is corrected by an amount according to the determined average aberration while the focus is scanned. These steps can be repeated for a plurality of different volumes in the sample, and an image of the sample can be generated based on the detected signal light from scanned foci within the different volumes.

48 Claims, 50 Drawing Sheets

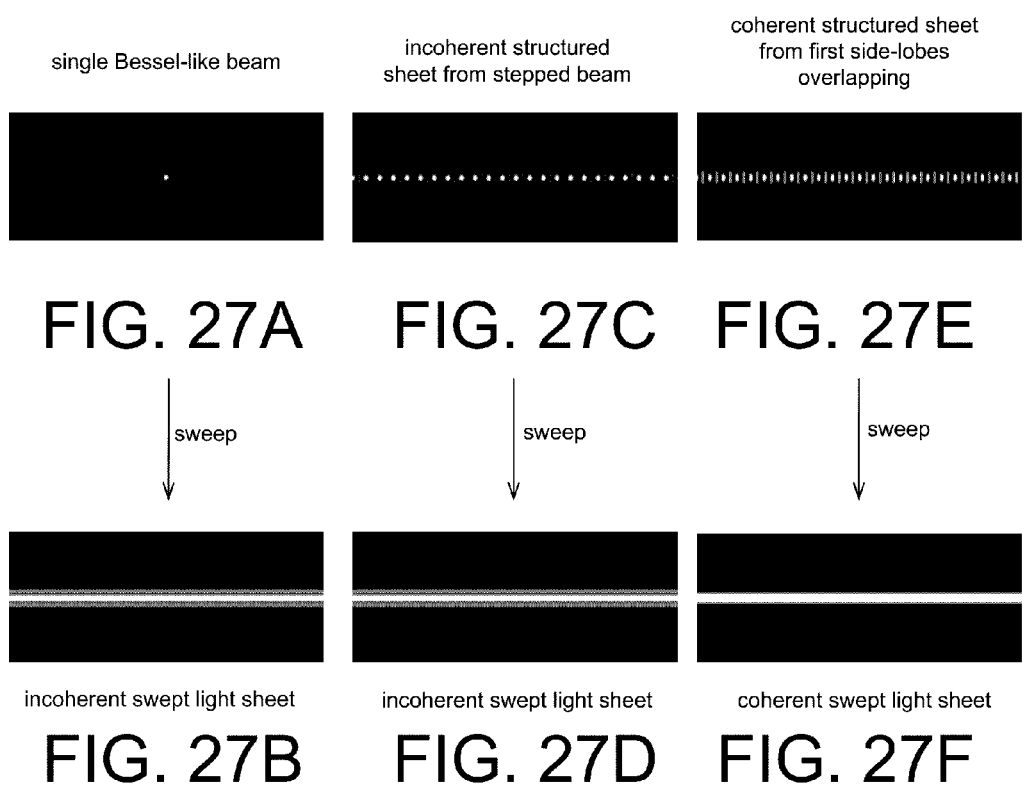

RAPID ADAPTIVE OPTICAL MICROSCOPY OVER LARGE MULTICELLULAR VOLUMES

CROSS-REFERENCE TO RELATED APPLICATIONS

This application claims priority to U.S. Provisional Patent Application No. 61/954,236, entitled "Rapid Adaptive Optical Recovery of Optimal Resolution over Large Multicellular Volumes," filed Mar. 17, 2014, and to U.S. Provisional Patent Application No. 61/979,482, entitled "Rapid Adaptive Optical Recovery of Optimal Resolution over Large Multicellular Volumes," filed Apr. 14, 2014. The subject matter of each of these earlier filed applications is hereby incorporated by reference.

TECHNICAL FIELD

This disclosure relates to microscopy and, in particular, to rapid adaptive optical microscopy over large multicellular volumes.

BACKGROUND

Optical imaging at diffraction-limited resolution in whole living organisms, where cell-cell interactions play crucial roles, is difficult due to refractive index heterogeneities arising from different cell morphologies within tissues and sub-cellular domains within cells. While adaptive optics ("AO") using a variety of approaches has been applied to this problem, AO microscopy is difficult to use in many specimens because of modal complexity and the large amplitude of the wavefront aberrations that are encountered, as well as how quickly these aberrations change as a function of position within the specimen.

SUMMARY

In a first general aspect, a method includes focusing first excitation light having a first wavelength to a first focus within a sample and scanning the first focus within a volume in the sample with one or more scanning optical elements. First signal light emitted from the first focus is de-scanned onto a wavefront sensor with the one or more scanning optical elements, as the first focus is scanned within the volume, and an average aberration created by the volume of the sample of a wavefront of the first excitation light is determined, based on the first signal light that is descanned onto the wavefront sensor. Second excitation light having a second wavelength is focused through the objective lens to a second focus within the volume in the sample, and the second focus is scanned within the volume in the sample with the one or more scanning optical elements. A wavefront of the second excitation light is corrected by an amount according to the determined average aberration while the second focus is scanned within the volume, and second signal light emitted from the sample in response to the second excitation light is imaged onto a photosensitive detector as the second focus is scanned within the volume, and a wavefront of the second signal light is corrected by an amount according to the determined average aberration while the second focus is scanned within the volume. These steps can be repeated for a plurality of different volumes in the sample, and an image of the sample can be generated based on the detected second signal light from scanned foci within the different volumes.

In another general aspect, a method includes focusing excitation light to a focus within a sample and scanning the focus within a volume in the sample with one or more scanning optical elements. Signal light emitted from the first focus is de-scanned, with the one or more scanning optical elements, onto a wavefront sensor as the focus is scanned within the volume, and, based on the signal light that is descanned onto the wavefront sensor, an average aberration created by the volume of the sample of a wavefront of the excitation light is determined. A wavefront of the excitation light is corrected by an amount according to the determined average aberration while the focus is scanned within the volume, the signal light is imaged onto a photosensitive detector as the focus is scanned within the volume, and a wavefront of the imaged signal light is corrected by an amount according to the determined average aberration while the focus is scanned within the volume. These steps can be repeated for a plurality of different volumes in the sample, and an image of the sample can be generated based on the detected signal light from scanned foci within the different volumes.

In another general aspect, a method includes focusing first excitation light with a first objective lens to a first focus within a sample, and scanning the first focus within a volume in the sample with one or more first scanning optical elements. As the first focus is scanned within the volume, first signal light emitted from the first focus is de-scanned onto a wavefront sensor with the one or more first scanning optical elements. Based on the first signal light that is de-scanned onto the wavefront sensor, a first average aberration created by the volume of the sample of a wavefront of the first excitation light is determined. Second excitation light is focused through a second objective lens to a second focus within the volume in the sample, and the second focus is scanned within the volume in the sample with the one or more second scanning optical elements. Second signal light emitted from the second focus is de-scanned, with the one or more of the second scanning optical elements, as the second focus is scanned within the volume onto a wavefront sensor. Based on the second signal light that is descanned onto the wavefront sensor, a second average aberration created by the volume of the sample of a wavefront of the second excitation light is determined. Third excitation light is provided through the second objective lens to the volume in the sample, and the third excitation light is scanned within the volume in the sample with the one or more of the second scanning optical elements. A wavefront of the third excitation light is corrected by an amount according to the determined second average aberration while the third excitation light is scanned within the volume and third signal light emitted from the sample is imaged, with the first objective lens, in response to the third excitation light onto a photosensitive detector as the third excitation light is scanned within the volume, and while correcting a wavefront of the third signal light by an amount according to the determined first average aberration while the third excitation light is scanned within the volume. These steps can be repeated for a plurality of different volumes in the sample, and an image of the sample can be generated based on the detected second signal light from scanned foci within the different volumes.

The details of one or more implementations are set forth in the accompanying drawings and the description below. Other features will be apparent from the description and drawings, and from the claims.

BRIEF DESCRIPTION OF THE DRAWINGS

FIG. 25A illustrates a cross-sectional profile in the X-Z plane of a Bessel like beam propagating in the Y direction. FIG. 25B illustrates the electric field, in the X-Z plane, of a structured light sheet formed by coherent sum of a linear, periodic array of Bessel-like beams that propagate in the Y direction. FIG. 25C illustrates the electric field, in the XZ plane, of the structured light sheet of FIG. 25B after a Gaussian envelope function has been applied to the field of the light sheet to bound the light sheet in the Z direction. FIG. 25D illustrates the pattern of phase shifts applied to individual pixels of a binary spatial light modulator to generate the field shown in FIG. 25C. FIG. 25E illustrates the cross-sectional point spread function, in the X-Z plane, of the structured plane of excitation radiation that is produced in the sample by the coherent array of Bessel-like beams, which are generated by the pattern on the spatial light modulator shown in FIG. 25D. FIG. 25F illustrates the excitation beam intensity that is produced in the sample when the array of Bessel-like beams is swept or dithered in the X direction.

FIG. 26A illustrates a cross-sectional profile in the X-Z plane of a Bessel like beam propagating in the Y direction. FIG. 26B illustrates the electric field, in the X-Z plane, of a structured light sheet formed by a coherent sum of a linear, periodic array of Bessel-like beams that propagate in the Y direction. FIG. 26C illustrates the electric field, in the XZ plane, of the structured light sheet of FIG. 26B after a Gaussian envelope function has been applied to the field of the light sheet to bound the light sheet in the Z direction. FIG. 26D illustrates the pattern of phase shifts applied to individual pixels of a binary spatial light modulator to generate the field shown in FIG. 26C. FIG. 26E illustrates the cross-sectional point spread function, in the X-Z plane, of the structured plane of excitation radiation that is produced in the sample by the coherent array of Bessel-like beams, which are generated by the pattern on the spatial light modulator shown in FIG. 26D. FIG. 26F illustrates the modulation transfer function, which corresponds to the point spread functions shown in FIG. 26E.

FIGS. 27A, 27B, 27C, 27D, 27E, and 27F are schematic diagrams of the intensities of different modes of excitation radiation that is provided to the sample. FIG. 27A is a cross-sectional in the X-Z plane of a Bessel-like beam propagating in the Y direction. FIG. 27B is a schematic diagram of the time-averaged intensities in the X-Z plane that results from sweeping the Bessel-like beam of FIG. 27A in the X direction. FIG. 27C is a cross-sectional in the X-Z plane of a superposition of incoherent Bessel-like beams propagating in the Y direction, such as would occur if the single Bessel-like beam in FIG. 27A were moved in discrete steps. FIG. 27D is a schematic diagram in the X-Z plane of the time-averaged intensity that results from moving multiple instances of the array of Bessel-like beams of FIG. 27C in small increments in the X direction and integrating the resulting signal on a camera. FIG. 27E is a cross-section in the X-Z plane of a superposition of coherent Bessel-like beams propagating in the Y direction. FIG. 27F is a schematic diagram of the time-averaged intensity in the X-Z plane that results from sweeping or dithering the array of Bessel-like beams of FIG. 27E.

DETAILED DESCRIPTION

Figure 1A:
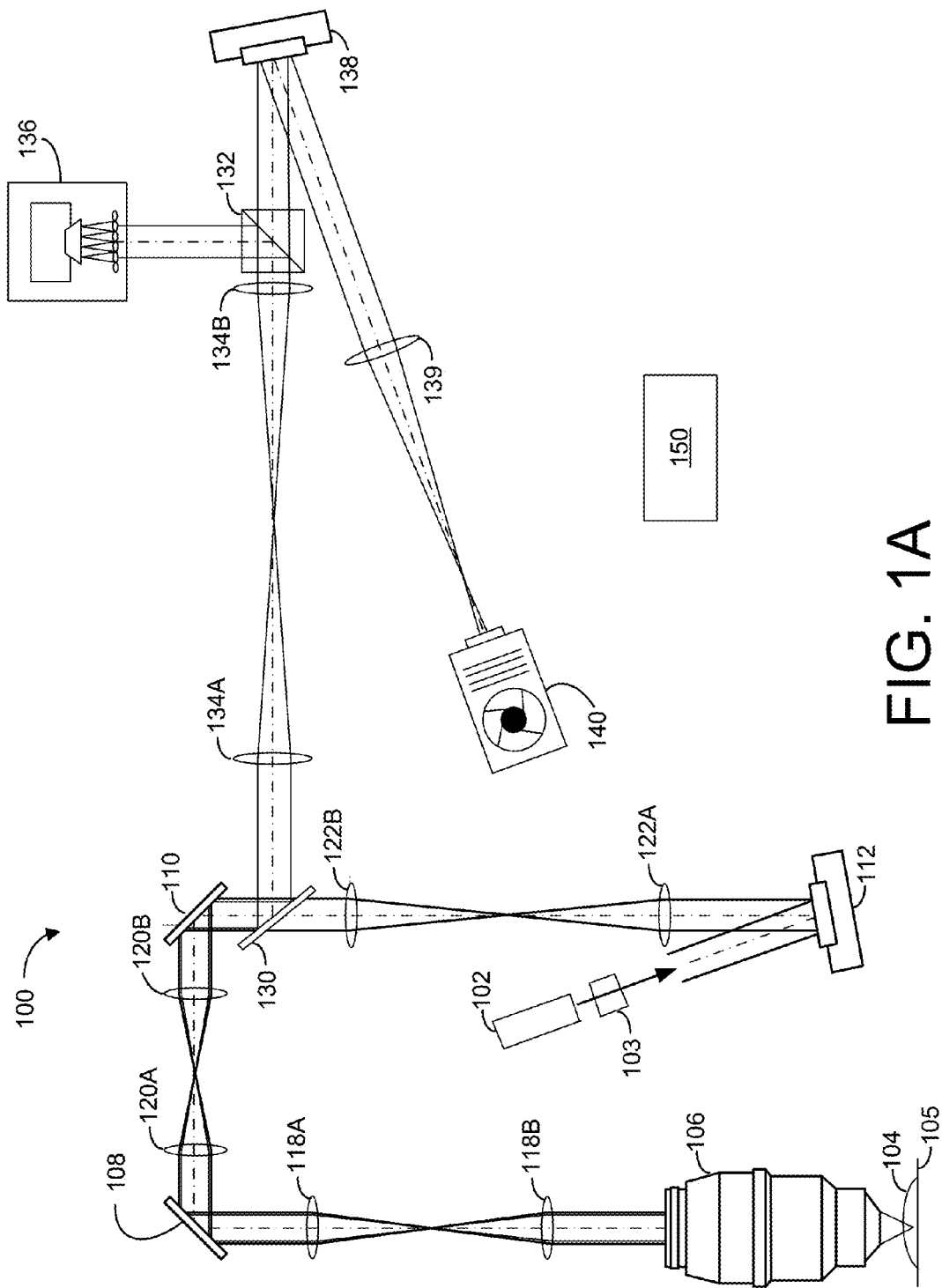
FIG. 1A is a schematic diagram of a microscope apparatus that can be used to implement the techniques described herein.

As described herein, a laser-induced guide star of the focus point of excitation light can be provided to a sample, and scanned through a portion of the sample. Light emitted from the location of the guide star in the sample can be de-scanned as the guide star is moved through the sample, and the wavefront of the de-scanned light can be directly measured as the guide star is scanned. Based on the measured wavefront, an adaptive optics correction for an averaged aberration over the portion of the sample over which the guide star is scanned can be determined. The determined averaged aberration can be applied to excitation light that is provided to the sample and/or to fluorescence emission light that is received from the sample to improve the resolution of images of the sample based on the fluorescence emission light. These techniques can be repeated for other portions of the sample, so that an aberration-corrected image of the sample can be constructed from individual aberration-corrected images of the portions of the sample.

Using such techniques, adaptive correction of complex optical aberrations can be applied at high numerical aperture and a at high update rates. Such techniques can be used to compensate for the rapid spatial variation in aberration often encountered in biological specimens and to recover diffraction-limited images of a sample over large volumes.

In some implementations, these techniques can be applied two-photon excitation mode. In some implementations, these techniques can be applied in a linear confocal fluorescence mode. Both modes provide corrective updates of complex, spatially varying aberrations sufficiently fast to recover diffraction-limited images of a sample over large imaging volumes, without observable measurement-induced photobleaching or photodamage to the sample.

Nonlinear excitation of the sample to emit fluorescence light at the position of the guide star insures that the fluorescence signal comes from a compact focal volume, without the need for exogenously introduced fluorescent point sources or pinhole filtering of out-of-focus fluorescence that can also filter out much of the modal structure in the aberration that adaptive optics techniques seek to correct. The guide star can be scanned over a small volume within the sample where the aberration of fluorescence light emitted from different positions within the volume varies, and the fluorescence light from the sample can be de-scanned such that a stationary wavefront the fluorescence light is projected to a wavefront sensor (e.g., a Shack-Hartmann lenslet array). By scanning the guide star over the volume within the sample but de-scanning the fluorescence light to maintain a stationary wavefront at the wavefront sensor, the finest, local, structure specific to each excitation point within the volume is averaged out as the guide star is scanned within the volume. As a result, the lenslets of the wavefront sensor sample the average wavefront slope over the scan volume, and a single spot appears in each cell of the sensor. This yields an accurate determination of the average aberration over the scan volume, which can be sufficient to recover nearly diffraction-limited performance over the entire scan volume.

In contrast, the AO compensation for a fixed guide star, even when locally correct, often provides less accurate correction when applied at other positions within a volume of positions that are close to the next position of the guide star. In addition, many biological specimens are so heterogeneous that the wavefront of fluorescence light can vary significantly on a scale that is small compared to even the individual lenslets of the wavefront sensor. This can result in complex speckle patterns in various cells of the sensor array of the wavefront sensor, which in turn yields inaccurate measurements of the local wavefront slope and thus incomplete or incorrect AO compensation, even at the chosen corrective point.

This techniques described herein are rapid, robust, and minimally invasive. The entire closed loop of application of the de-scanned fluorescence light to the wavefront sensor, wavefront calculation, and wavefront modulating element (WME) based correction of the excitation light wavefront and/or fluorescence light signal wavefront can be performed in times on the order of 10 ms, which facilitates scanning large sample volumes requiring many corrective volumes. The techniques described herein utilize excitable fluorophores within the sample, which exist in sufficient numbers within each scan volume to provide fluorescence light from the scanned guide star, rather using a specific, fixed fluorescent features within the sample and subsequent targeting of the guide star. Finally, photo-induced bleaching or sample damage is mitigated by the techniques described herein, because the excitation is spread over the entire scan volume, rather than concentrated at a single corrective point that may in fact be the point of greatest interest.

FIG. 1A is a schematic diagram of a microscope apparatus 100 that can be used to implement the techniques described herein. The apparatus 100 can include an excitation light source 102 that provides excitation light to a sample 104. The light source 102 can include a laser. The provision of excitation light from the light source 102 to the sample 104 can be modulated by one or more structures between the light source 102 and the sample 104. For example, a Pockels cell 103 can be computer controlled by the computing system 150 to modulate the provision of excitation light from the light source 102 to the sample 104. The sample 104 can be supported by a stage 105. The position of the stage 105 can be moved in orthogonal directions, for example, under computer control by the controller in the computing system 150.

The light source 102 can provide a plane wave of excitation light that can be focused to a focal point within the sample 104 by an objective lens 106. The focal point within the sample can be scanned in directions perpendicular to the axis of the objective 106 by first (X) galvanometer mirror 108 and a second (Y) galvanometer mirror 110. The galvanometer mirrors 108, 110 can be controlled by hardware or software, or a combination of the two, in the computing system 150. The wavefront of the excitation light can be modified by a wavefront modulating element (WME) 112 that reflects the beam of excitation light. In some implementations, the WME can include a spatial light modulator (SLM). In some implementations, the WME can include a deformable micromirror (DMD). Each of the first galvanometer mirror 108, the second galvanometer mirror 110, and the WME 112 can be optically conjugate to the rear pupil of the objective lens 106 by virtue of pairs of lenses 118A, 118B, 120A, 120B, 122A, 122B. The WME 112, both galvos 108, 110, and the objective rear pupil are all mutually conjugate, so the phase pattern from the WME is stationary at the rear pupil of the objective 106, even as the galvos scan the focused excitation light laterally across the sample 104.

In one implementation, the excitation light provided by the light source 102 can have a wavelength that is longer than the wavelength of fluorescence light emitted in response to the excitation light. For example, two photons of light provided by the light source 102 may be required to excite a label within the sample 104 to a state that emits fluorescence light. Such a configuration may be referred to as a two-photon excitation (TPE) mode of operation.

In an example implementation, light source 102 can provide pulsed light from a Ti:Sapphire laser (Coherent, Chameleon Ultra II), whose intensity is controlled by a Pockels cell 103 (Conoptics, 350-80-LA-02), and whose beam can be expanded to a $1/e^2$ diameter of 8 mm before being reflecting at 8° from the normal off of the WME 112, which can be a NIR-responsive spatial light modulator (SLM NIR, Boulder Nonlinear Systems, HSP256-1064). The SLM 112 can be used to apply the corrective pattern needed to retain a diffraction-limited two-photon excitation (TPE) focus in the specimen. The lenses 122A and 122B can be a pair of NIR achromatic relay lenses (focal lengths $f_1=150$ mm and $f_2=125$ mm) operating in a $2f_1+2f_2$ configuration then that are used to image the WME 112 onto the mirror 110 (e.g., a 5 mm mirror of a galvanometer (Y Galvo, Cambridge Technology, 6215H)). The lenses 120A, 120B, can be pair of $f_1=f_2=85$ mm relay lenses that image the WME 112 onto mirror 108 (e.g., a second 5 mm galvo mirror (X Galvo, Cambridge Technology, 6215H)). Lenses 118A, 118B can be a pair of $f_1=89$ mm and $f_2=350$ mm relay lenses that create a magnified image of the WME 112 at the rear pupil plane of the detection objective 106 (e.g., Nikon, CFI Apo LWD 25XW, 1.1 NA and 2 mm WD). Mutual conjugation of the WME 112, both galvos 108, 110, and the rear pupil of the objective 106 insures that the corrective phase pattern from the WME 112 is stationary at the rear pupil of the objective, even as the galvos 108, 110 scan the focused NIR light laterally across the sample 104.

Fluorescence light emitted from the sample 104 in response to the focused excitation light can be collected by the objective 106 and reflected off the first and second galvanometer mirrors 108, 110, and a dichroic beamsplitter 130 may reflect light having a wavelength at, or close to, the wavelength of the fluorescence light, while transmitting light having a wavelength at, or close to the wavelength of the excitation light. Fluorescence light collected by the objective 106 and reflected by the first and second galvanometer mirrors 108, 110 can be reflected by the dichroic beamsplitter 130 and then provided to polarizing beamsplitter 132 into two different paths. The polarizing beamsplitter 132 is optically conjugated to the galvanometer mirrors 108, 110, the WME 112, and the rear pupil of the objective 106 by virtue of the lens 134A, 134B. One path of light from the beam splitter is provided to a wavelength sensor 136 (e.g., a Shack-Hartmann sensor) that is configured to measure the wavefront of the fluorescence light and to determine the aberrated wavefront of the emission light. Another path of the light from the beam splitter 132 is reflected from a wavefront modulating element 138 before being focused onto a detector 140 (e.g., a photomultiplier tube). The wavelength sensor 136 and the wavefront modulating element 138 also are optically conjugate to the rear pupil of the objective 106, to the galvanometer mirrors 108, 110 and to the WME 112 by virtue of the mirrors 134A, 134B.

In the configuration shown in FIG. 1A, because the fluorescence light emitted from the focal point of the excitation light within the sample 100 is de-scanned by the galvanometer mirrors 108, 110 that scan the focal point of the excitation light through the sample, the position of the light provided to the wavefront sensor 136 remains fixed on the wavefront sensor as the focal point of the excitation light is scanned in the sample. The signal on the wavefront sensor 136 can be integrated in time as the focal point of the excitation light is scanned within a volume within the sample 104. Then, a wavefront analysis module within a computing system 150 can be used to determine average aberrations caused by the volume of the sample to incoming excitation light or to outgoing fluorescence light. A wavefront correction module within the computing system 150 can be used to generate a pattern to apply to the wavefront modulating element 112 that can be used to compensate for the determined aberrations, over the volume, in the excitation light that is supplied by the light source 102 to the sample 104. The wavefront correction module also can be used to generate a pattern to apply to the wavefront modulating element 138 that can be used to compensate for the determined aberrations, over the volume, in the fluorescence light that is received from the sample 104.

In some implementations, the determination of the average aberrations caused by the volume of the sample and the application of the pattern(s) to compensate for the aberrations can be performed as the focal point of the excitation light is scanned through the sample. In this manner, the aberration-correcting pattern(s) are continually updated as the focal point is scanned through the sample and while fluorescence signal light is measured by the detector 140 and recorded as a function of position of the focal point in the sample, thus continually correcting for sample-caused aberrations. In some implementations, the determination of the average aberrations caused by the volume can be determined, then the aberration-correcting pattern(s) can be applied, and then the volume can be rescanned by the focal point while fluorescence light is collected by the detector 140 and recorded as a function of the position of the focal point within the sample. The fluorescence signal light measured by the detector 140 as a function of the position of the focal point in the sample can be used to generate an image of the volume of the sample. The process can be repeated over many different volumes of the sample, and the recorded information for the different volumes can be combined to generate an image of the sample that includes many volumes. For example, the computing system 150 may include one or more processors and one or more memories that can process the recorded information to generate an image of the sample based on the information for the different volumes provided by the detector.

In an example implementation, the focused fluorescence emission light from the sample can be collected by the objective 106 and initially can follow the reverse path of the excitation beam. After galvo mirror 110, however, a dichroic beamsplitter 130 (e.g., Semrock FF705-Di01-25x36) can divert the emission light through the relay lens pair 134A, 134B that conjugates Galvo 110 to WME 138. A portion of this unpolarized light passes through the PBS 132, reflects off WME 138, and can focused by a lens 139 (e.g., a f=300 mm lens) before being detected by detector 140 (e.g., a photomultiplier tube (PMT, Hamamatsu, H7422-40 or R10467U-40)). The signal from this detector 140 forms the image of the sample. The other half of the fluorescence light is reflected by the PBS 132 and is sent to the wavefront sensor 136, which is positioned such that the lenslet array (e.g., having 10×10 lenses, 0.5 mm pitch, f=46.7 mm, Edmund Optics, 64-483) of the sensor 136 is conjugate to the rear pupil of the objective 106 and the two galvos 108, 110. As a result, the detected light is de-scanned by the galvos 108, 110, and a stationary wavefront is presented at the sensor 136, even as the focused excitation light is scanned laterally across the sample 104. Displacements of the foci on the wavefront sensor's camera (e.g., Andor iXon3 897 EMCCD) then solely represent the local wavefront gradients, as desired.

The PBS 132 can be used to split the fluorescence signal between the wavefront sensor 136 and the imaging PMT 140 because when the WME 138 includes an SLM, the SLM may require linearly polarized light to modulate the phase properly. However, while this configuration is perhaps the simplest for an SLM-based system, the 50% signal loss at the detector 140 is a substantial price to pay. On the other hand, the question of the optimum split ratio is a complex one, as a number of factors influence how much signal the wavefront sensor 136 requires to accurately measure the displacement of each lenslet-defined focal spot. Increasing the number of lenslets increases the complexity of the aberration that can be measured, but divides the signal at the sensor 136 among more elements. Decreasing the size of each AO corrective volume provides more local measurement of the aberration, but decreases the total integrated signal collected for each such measurement. Finally, increased imaging depth generally leads to greater aberration and thus more dramatic improvement after AO correction, but also results in more scattered background and less ballistic (focused) light at the wavefront sensor, requiring more signal to accurately measure the focal spot displacements. In short, while the 50/50 ratio of the PBS configuration represents a simple compromise that works well for the specimens studied here, other configurations, including a system with a variable split ratio, can be used for other biological systems.

Figure 1B:
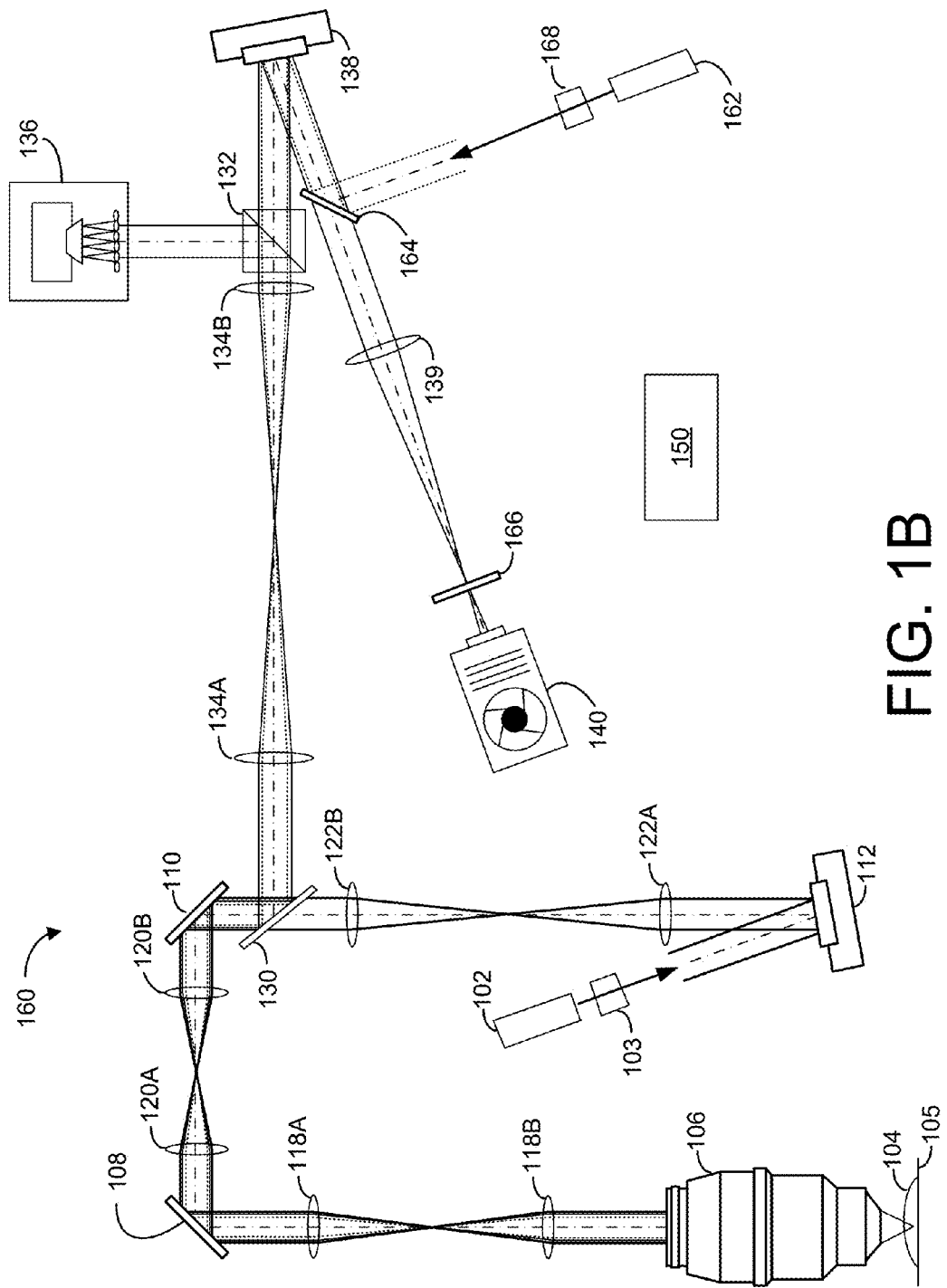
FIG. 1B is a schematic diagram of a microscope apparatus that can be used to implement the techniques described herein.

FIG. 1B is a schematic diagram of another microscope apparatus 160 that can be used to implement the techniques described herein. The microscope apparatus 160 is similar to that of the scope apparatus 100 in FIG. 1A, except that it includes a light source 162 that provides single photon excitation light to the sample 104 to image the sample. Excitation light from the light source 162 can be provided to the sample 104 by using a dichroic beamsplitter 164 that reflects light from the light source 162 and that transmits fluorescence light received from the sample. In some implementations, the light source 162 can include a number of different lasers or LEDs that provide light having different wavelengths. A particular wavelength can be selected for provision to the sample 104 by an acoustical-optic tunable filter (AOTF) 168 located between the light source 162 and the WME 138.

In addition, the apparatus 160 can include a mask 166 having a pinhole in the beam path of the fluorescence light at a location that is optically conjugate to the focal point of the excitation light in the sample 104. In some implementations, light source 102, can provide excitation light to generate the guide star within the sample via two photon excitation, and fluorescence light from the guide star is provided to the wavefront sensor 136 and used to determine average aberrations created in a volume over which the guide star is scanned in the sample. After the aberration-correcting pattern for the WME 138 has been determined, in a second step, a focal point of excitation light provided from the light source 162 can be scanned over the volume for which the aberration-correcting pattern has been determined to generate a fluorescence signal that is detected at the detector.

In an example implementation, the light source 162 can include four CW lasers having different wavelengths, λ, (e.g., λ=440 nm, 50 mW, CrystaLaser; λ=488 nm, 200 mW, Coherent Sapphire 488 LP; λ=514 nm, 300 mW, MPB Communications, model 2RU-VFL-P-300-514-R; and λ=561 nm, 200 mW, Coherent Sapphire 561 LP) whose beams are expanded to a common a $1/e^2$ diameter of 2 mm and combined into a single co-linear beam using dichroic beamsplitters (Semrock, LaserMUX family) (not shown). An acousto-optic tunable filter (AOTF, AA Opto-Electronic, AOTFnC-400.650-TN) 168 can select one or more wavelengths and control the power of each. The linearly polarized output of the AOTF 168 can be expanded to a $1/e^2$ diameter of 10 mm, inserted into the microscope beam path using the dichroic beamsplitter 164 (Semrock Di01-R442/510-25x36 or Di01-R488/561-25x36), and reflected from the wavefront modulating element 138 responsive to visible light (SLM VIS, Boulder Nonlinear Systems, HSP256-0532). The WME 138 can be used to apply the corrective pattern needed to retain both a diffraction-limited visible excitation focus in the sample 104, and a diffraction-limited focus of the fluorescence emission at a mask pinhole 166 (50 µm, Thorlabs, P50S) that provides filtering for the confocal imaging mode. After passing through the beam splitter 132 (PBS, Thorlabs, PBS251), a pair lenses 134A, 134B ($f_1$=150 mm and $f_2$=125 mm relay lenses) can image WME 138 onto the Galvo mirror 110. Thereafter, the path to the sample 104 is shared with the elements shown in FIG. 1A. Consequently, WME 138, both galvos 108, 110, and the rear pupil of the objective 106 are also mutually conjugate, and a corrective phase pattern from WME 138 is stationary at the rear pupil of the objective 106, even as the galvos scan the focused visible light laterally across the sample 104.

This confocal mode provided by the apparatus 160 can provide multicolor near-diffraction limited resolution over large regions of a sample 104, such as oligodendrocytes and neuronal nuclei of the zebrafish brain from the top of the optic tectum down 200 µm deep in the midbrain. Thus, it is possible to study sub-cellular organelles in the optically challenging environment of a living vertebrate with the clarity normally associated with isolated cultured cells. Examples include centriole pairs of centrosomes in photoreceptors of the retina, and the plasma membrane and mitochondria in a neuron ~150 µm deep in the hindbrain. Time lapse imaging of two neurons in the hindbrain shows mitochondrial dynamics in the soma and surrounding neurites.

While the confocal mode can provide better resolution than the TPE mode for depths at which the scattering of visible light is negligible, the longer scattering length of infrared light makes the TPE mode applicable at greater depths. Nevertheless, for many samples, scattering will eventually render either mode unusable, as the focus of the ballistic component of the fluorescence in each cell of the wavefront sensor 136 will become dominated by the unfocused background from the scattered component.

In some implementations, to mitigate the deleterious effect of scattering on the signal that is imaged onto the wavefront sensor 136 and used to determine the aberrated wavefront of the emission light and to determine the AO correction to be applied to the WME 138, the wavelength of light that is imaged onto the wavefront sensor can be chosen to reduce the effect of scattering within the sample on this light. For example, infrared light can be selected, because the scattering cross-section of infrared light is lower than that of visible light. In some implementations, the sample can be prepared with materials (e.g., one or more dyes) that emit infrared light in response to the excitation light that is provided to the sample. The infrared fluorescence light can be imaged onto the wavefront sensor and used to determine the aberrated wavefront of the emission and to determine the AO correction that is to be applied to the WME 138 that provides AO correction to light (e.g., visible wavelength fluorescence light) that is used to create images of the sample. In this manner, the techniques described here can be applied to media that are generally considered to scatter signal light significantly.

Because aberrations can vary rapidly as a function of position within biological samples, large volumes can be imaged by dividing them into smaller volumes, and an averaged AO correction unique to each volume can be determine. Stacked, closed-loop ultrasonic piezomotor stages (Physik Instrumente, M-663.465) can be used initially for x-y positioning of the sample to the focal point of the objective, as well as for lateral translation between processing different volumes. A closed loop ball-screw driven stage (Physik Instrumente, M-110.2DG) can provide similar functions in z. Within each volume, X Galvo and Y Galvo scan the focus laterally, while a piezo flexure stage (Physik Instrumente, P-622.2CD) steps between scan planes to build a 3D image of the volume. At each voxel, the fluorescence photons reaching PMT generate current spikes which first can be amplified (FEMTO Messtechnik GmbH, DLPCA-200) and then integrated over the pixel dwell time in a custom, fast-resetting analog integrator. The integrator output can be digitized by an FPGA-based reconfigurable I/O board (National Instruments, PCIe-7852R) just prior to integrator reset from the same board at the end of the dwell period.

In the two-photon imaging mode, AO correction can occur simultaneously with image acquisition. The exposure time of the camera of the wavefront sensor 136 can be chosen to be just long enough to yield a signal-to-noise sufficient to accurately measure the gradient of the wavefront. Calculation of the wavefront from this gradient can occur concurrently with the next exposure of the wavefront sensor, and the resulting correction of sample-induced aberration is added immediately to the individual system corrections at WME 138 and WME 112. The closed-loop update time for new AO corrections can be on the order of 10 ms, being limited in bright samples by the read-out speed of the EMCCD-based camera in the wavefront sensor 136. A sCMOS-based camera may permit faster update times for AO corrections.

In the confocal mode shown in FIG. 1B, AO correction can occur sequentially: in each corrective volume, the visible excitation is first blocked with the AOTF 168, and the NIR light from light source 102 is passed by the Pockels cell 103, and a fraction of the volume (often a single plane) is scanned by the TPE focal point while the resulting de-scanned fluorescence is collected in a single exposure at the wavefront sensor 136. After the wavefront correction is calculated and added to the system corrections at WME 112 and WME 138, the NIR light from light source 102 is blocked, and the visible light from light source 162 is passed in order to image the entire volume.

In both the TPE and confocal modes, the aberration-corrected 3D point spread function (PSF) of the apparatus 100, 160 is first determined by imaging an isolated 200 nm diameter fluorescent bead on a glass slide with system corrections applied to both WME 112, 138. For regions of the sample where AO correction recovers near diffraction-limited resolution, these measured PSFs can be used to deconvolve the 3D imaging data via the Lucy-Richardson algorithm in Matlab. This provides a sharper 3D representation of the imaging volume that depicts the sample and the relative amplitudes of its spatial frequencies more accurately. Volume renderings of the data can be created in Amira (FEI Visualization Sciences Group). For data sets with intensities covering a large dynamic range, a gamma function is often applied to visualize the dimmer features.

Figure 2:
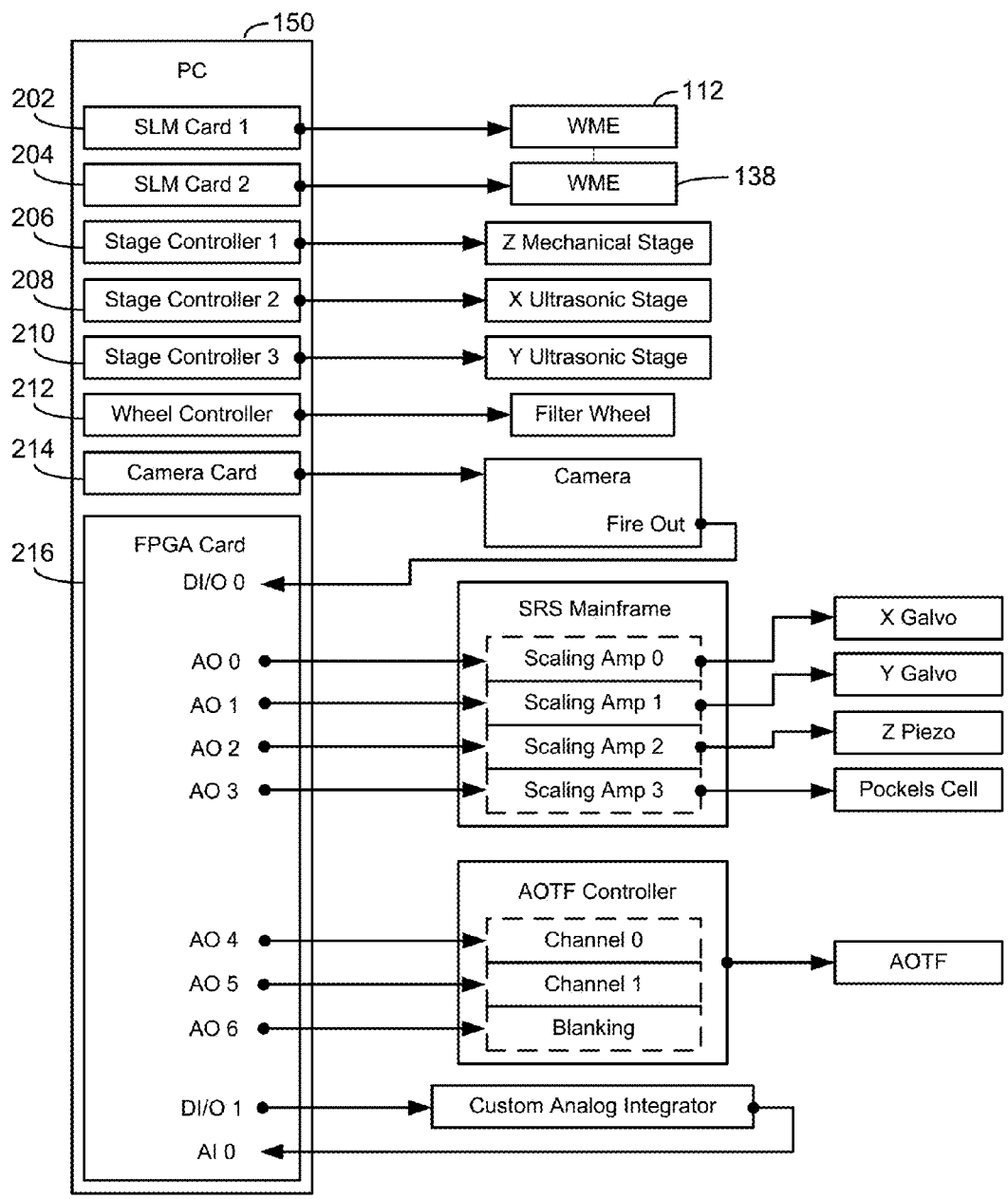
FIG. 2 is a schematic diagram of various components of a computing system that are used to control various components of an apparatus that can be used to implement the techniques described herein.

FIG. 2 is a schematic diagram of various components of the computing system 150 that are used to control various components of the apparatus 100. The components and FIG. 2 are schematic and exemplary and the computing system 150 may include different or other components that are used to control the components of apparatus 100. In addition, it is appreciated that computing system 150 can include one or more separate computing devices that operate together to control the apparatus 100.

Computing system 150 can include an WME card 202 containing hardware and/or software that controls the pattern applied to WME 112 and can include an WME card 204 containing hardware's and/or software that controls the pattern applied to WME 138. Stage controllers 206, 208, 210 can include hardware and/or software that controls, respectively, the vertical motion (i.e. along the optical axis of the detection objective 106) of the stage 105 and motion of the stage 105 in two directions that are mutually orthogonal and also orthogonal to the optical axis of the detection objective. A wheel controller 210 can include hardware and/or software that controls a filter wheel containing different wavelength filters that are inserted in the beam path between the light source 102 and the sample 104 and that allow different bandwidths of light to pass from the light source 102 to the sample 104. A camera card 214 can include hardware and/or software that control the operation of a camera in the wavefront sensor 136. For example, the camera card 214 can send a signal to the camera to activate the camera. In response, the camera can send a signal to a field programmable gate array (FPGA) card 216 that includes hardware and/or software for controlling other components of the apparatus 100.

The FPGA card 216 can send signals to scaling amplifiers that, in turn, control the operation of galvanometer mirrors 108, 110, a piezoelectric transducer that controls motion of the stage 105 in a direction along the axis of the objective lens 106, and that control the Pockels cell 103 to modulate the excitation light that is provided to the sample 104. The FPGA card 216 also can send signals to and acoustical-optic tunable filter (A OTF) controller that, in turn, send signals to and A OTF that is operated to select a wavelength of excitation light that is provided to the sample 14 from the light source 102.

Figure 3:
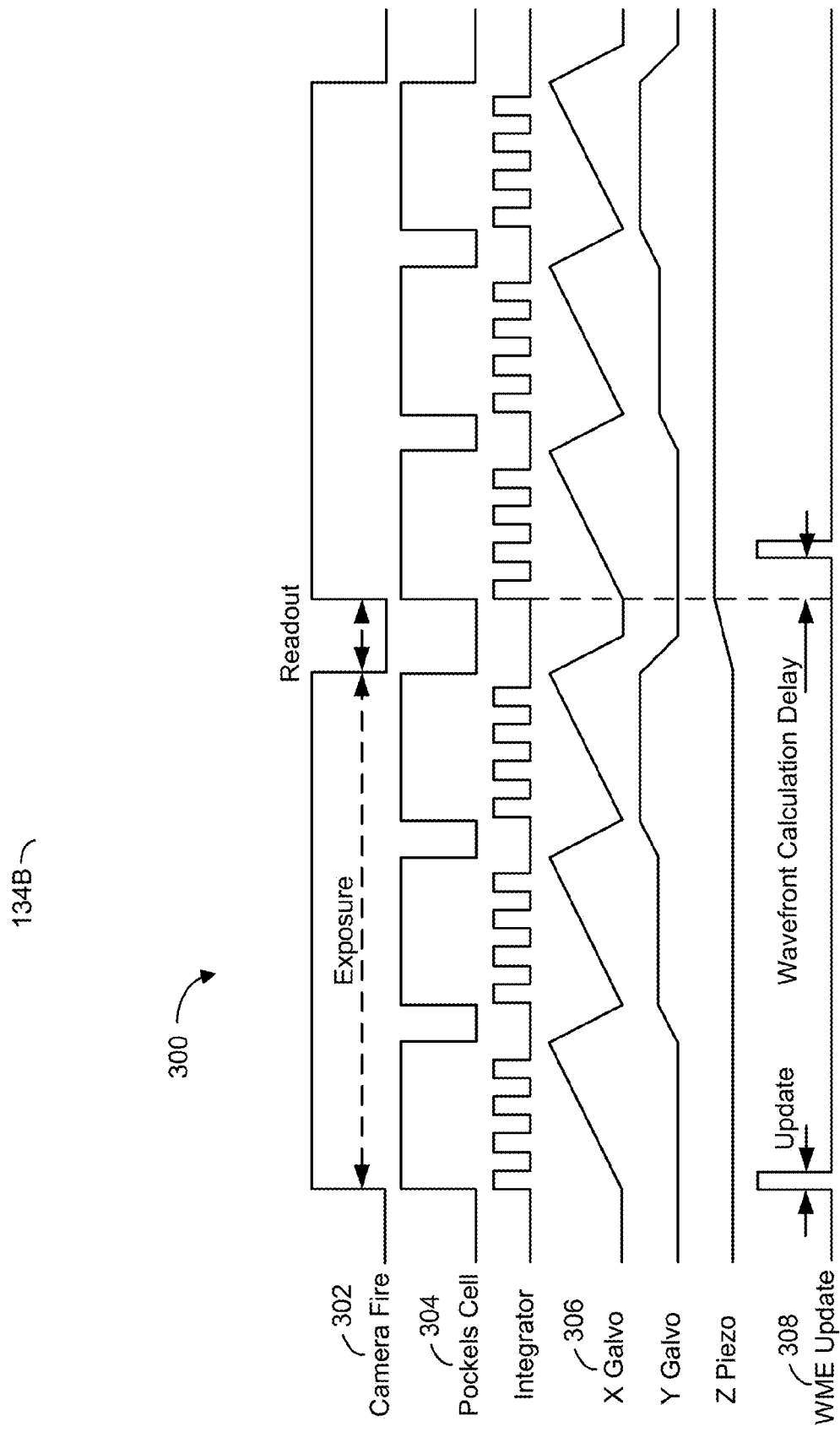
FIG. 3 is a timing diagram of the operation of various components of an apparatus that can be used to implement the techniques described herein.

FIG. 3 is a timing diagram 300 of the operation of various components of the system 100 in FIG. 1. The first line 302 of the diagram shows that a camera of the wavelength sensor 136 is turned on at a first time, $T_1$, and remains on until a time, $T_6$. Turning on the camera at time, $T_1$, coincides with: modulating excitation light from the light source 102 with the Pockels cell 103 to provide excitation light to the sample 104, as shown in the second line 304 of the diagram; with the beginning of a sweep of the focal point of the excitation light in the X-direction within the sample as shown in line 306 of the diagram; and with the updating of the pattern applied to the WME 112 and the pattern applied to the WME 138, as shown in line 308 of the diagram. Sweeping of the focal point of the excitation light in the X-direction within the sample proceeds until $T_2$, and then the excitation light is turned off at the sample by changing the state of the Pockels cell 103. Between $T_2$ and $T_3$, the galvanometer mirrors are adjusted to bring the X-axis position of the focal point of excitation light to its original position and to step the Y-axis position of the focal point of excitation light to a new position. The processes that occur between $T_1$ and $T_2$ are repeated between $T_3$ and $T_4$, and between $T_5$ and $T_6$, except that the patterns of a WMEs 112, 136 are not updated. The processes that occur between $T_2$ and $T_3$ are repeated between $T_4$ and $T_5$, except that the patterns on WMEs 112, 138 are not updated. Between $T_6$ and $T_7$, the integrated, time-averaged, aberrated wavefront is read out from the wavefront sensor, the excitation light is blocked from the sample by the Pockels cell 103, the galvanometer mirrors are adjusted to bring the X-axis and Y-axis positions of the focal point back to their original positions, and a Z position of the sample with respect to the detection objective is changed. Between $T_7$ and $T_8$, pattern(s) to be applied to the WME 112 and to the WME 138 are calculated, and then the entire process can be repeated.

In general, it may be difficult to know a priori for different organisms and different regions within a given organism how to choose the dimensions of the corrective volume. It is desirable to choose a size of the volume that is large enough to average out aberrations that are due to very localized features of the sample but that is small enough to generate an average aberration correction that is applicable to most or all of the scanned points within the volume. Fortunately, for structurally and developmentally stereotypical organisms, such as zebrafish, a library of volume sizes obtained empirically from one sample can be validly applied to subsequent ones. In addition, appropriate volume sizes can be determined empirically by comparing the resolution of images of the sample generated using volume different dimensions.

Near-diffraction-limited performance of the apparatus 100 can be attained even though a wavefront measurement based on emission light having a wavelength ($\lambda$) is applied to the WME 112 that modulates that excitation light, provided by the light source 102, that has a wavelength that is close to $2\lambda$. In addition, the wavefront measurement can occur simultaneously with TPE imaging, so there is no need to pause for correction. Finally, these techniques are sufficiently fast and non-invasive to study sub-cellular dynamics for extended periods in developing embryos, as well as the neurite-guided motility of oligodendrocytes deep in the zebrafish hindbrain.

Before measuring and correcting sample-induced aberrations, the microscope 100, 160 can be calibrated to compensate for its own aberrations that arise, for example, due to imperfect and/or misaligned optical components. These system aberrations can be measured by the phase retrieval method, described by Gerchberg, R. W. & Saxton, W. O. "A practical algorithm for the determination of phase from image and diffraction plane pictures," *Optik* 35, 237-246 (1972), which is incorporated herein by reference, since it provides an independent means to determine the correction necessary to recover an ideal diffraction-limited focus for an ideal, non-aberrating point object.

To correct the aberrations in the visible light path, the pinhole mask 166 near the detector 140 is removed, and a 3D image of an isolated, 200 nm diameter fluorescent bead on a glass slide in the sample position is obtained by scanning the visible focus in a series of xy planes, and stepping the sample in z to different planes with a piezoelectric flexure stage (Physik Instrumente, P-622.2CD). The sampling interval must be smaller than the Nyquist limit ($N_{x,y} = \lambda/(4NA)$, $N_z = \lambda/[2n(1-\sqrt{1-(NA/n)^2})]$) in each direction, and the field of view must be large enough that aberrated images of the bead are not cropped at the edges. The 3D image is then inspected, particularly for axial asymmetry indicative of spherical aberration, and the correction collar on the objective is adjusted. This process of 3D imaging and collar correction is repeated until the spherical aberration is minimized.

Next, the bead can be moved to the z plane of best focus, and a series of seven 2D images can be taken while applying seven different Zernike polynomial phase patterns of 2λ peak-to-peak amplitude on the WME 138: flat phase; positive defocus; negative defocus; positive x astigmatism; negative x astigmatism; positive y astigmatism; and negative y astigmatism. From these images, the wavefront correction for system aberration in the visible excitation path can be retrieved using the Gerchberg-Saxton algorithm described in Gerchberg, R. W. & Saxton, W. O., "A practical algorithm for the determination of phase from image and diffraction plane pictures," *Optik* 35, 237-246 (1972). Thereafter, this pattern can be applied to WME 138, and the wavefront correction for sample-induced aberrations can be added to it to provide complete correction during normal operation.

To correct for aberrations in the NIR light path between light source 102 and the objective 106, a CCD camera (AVT, Guppy F-146) can be placed at the intermediate image plane located at the focus of the first relay lens 118A after X Galvo 108. Seven 2D images of this focus are taken while applying the seven Zernike polynomial phase patterns listed above to WME 112, and the wavefront correction for system aberration in this portion of the NIR excitation path is retrieved using the Gerchberg-Saxton algorithm. Thereafter, this pattern is applied to WME 112, and the wavefront correction for sample-induced aberrations is added to it to provide complete correction during normal operation.

To calibrate the wavefront sensor, the visible and NIR wavefront corrections for system aberration are applied to WME 138 and WME 112, respectively. A 2D image of a field of fluorescent beads is then taken in the TPE imaging mode while integrating the signal at the camera of the wavefront sensor 136. The resulting image on the camera includes of an array of foci, matching the elements of the lenslet array. The centroids of these foci are determined to sub-pixel precision, and serve as the calibration reference. Thereafter, the displacements of these centroids from their reference positions indicate the local gradient of the sample-induced wavefront error, from which the wavefront itself can be calculated using a generalized matrix inversion method.

Although the apparatus 100 and the apparatus 160 use a focal point of light to generate fluorescence signal emission light that is detected and processed to generate an image of the sample, excitation light can be provided to the sample 104 in other ways as well. For example, excitation light can be provided to the sample 104 in the form of a thin sheet of light. Such techniques are described, for example, in U.S. patent application Ser. No. 13/844,405, entitled, "Structured Plane Illumination Microscopy," filed Mar. 15, 2013, which is incorporated herein by reference, and are described in more detail below in the section entitled, "Thin Light Sheets."

When a thin light sheet is provided in a plane to a sample, fluorescence emission light emitted in a direction that has a component orthogonal to the plane can be detected and processed to generate an image of the sample. Using a thin sheet of light provided in the focal plane of the detection objective can reduce the unwanted background light generated in regions of the sample that are out of focus for the detection objective. Using the adaptive optics techniques described herein, sample-induced aberrations that would distort the thin light sheet can be compensated, so that a higher quality sheet of excitation light can be provided to the sample.

Figure 4:
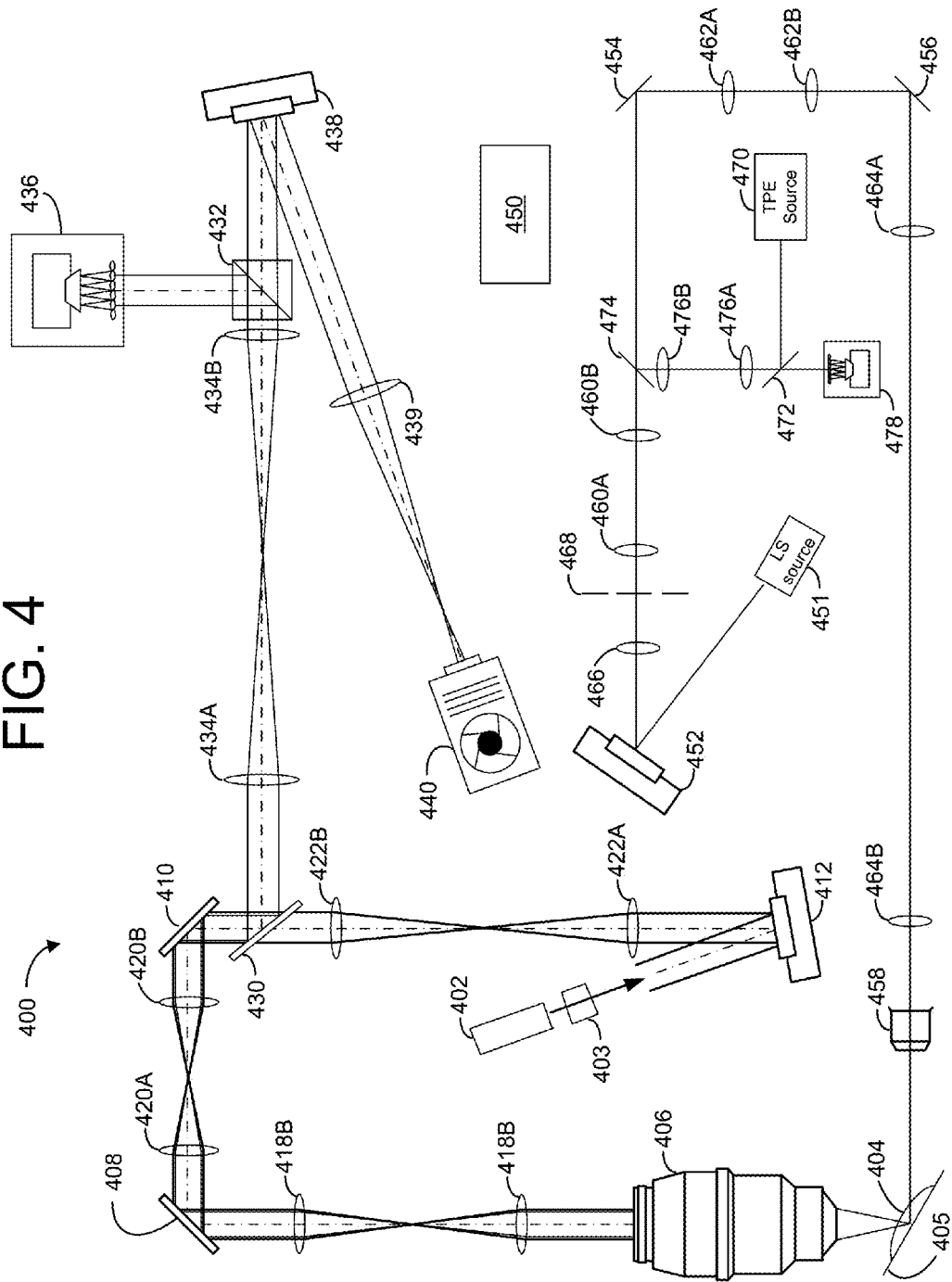
FIG. 4 is a schematic diagram of a microscope apparatus that can be used to implement the techniques described herein.

FIG. 4 is a schematic diagram of another microscope apparatus 400 that can be used to implement the techniques described herein. The apparatus 400 includes an excitation pathway between a light source 451 and the sample 404. The light source 451 provides excitation light to the sample 404. The apparatus 400 includes a detection pathway between the sample 404 and a detector 440.

The excitation pathway from the source of excitation light 451 includes a wavefront modulating element 452, an X-axis galvanometer mirror 454, a Y-axis of galvanometer mirror 456, and an objective lens 458. The objective 458 focuses the excitation light provided to a rear pupil of the objective into a pattern that creates a thin sheet of excitation light within the sample 404 or that can be used to create a thin sheet of excitation light within the sample 404. The X-axis galvanometer 454 and the Y-axis galvanometer 456 can be used to steer the beam of excitation light in directions orthogonal to the propagation direction of the excitation light in the sample.

Light that is modulated by the wavefront modulating element 452 can be imaged by a lens 466 onto an apodization mask 468 that is conjugate to the rear pupil of the objective lens 458. Pairs of relay lenses 460A, 460B and 462A, 462B and 464A, 464B serve to ensure that the apodization mask 468 and the galvanometer mirrors 454, 456 are mutually conjugate to each other and also are conjugate to rear pupil of the objective 458. The WME 428 is conjugate to the focal point of the excitation light within the sample 404. A phase pattern that is applied to the WME 452, in conjunction with the apodization mask 468, can create a pattern at the rear pupil of the objective lens 458 that, when focused by the objective lens into the sample 404 creates the thin sheet of excitation light or that creates a beam of excitation light that, when swept within the sample, creates the thin sheet of excitation light.

To determine the sample-induced aberrations, a light source 470 can supply excitation light to the sample 404. In some implementations, the light source 470 is a two-photon excitation source, such that the wavelength of light emitted from the source 470 is longer than the wavelength of fluorescence light emitted in response to the light provided to the sample by the source 470. Dichroic mirrors 472, 474 can reflect the light from the light source 470 into the pathway that includes the X-axis galvanometer mirror 454, the Y-axis galvanometer mirror 456, and the objective lens 458. A pair of relay lenses 476A, 476B can conjugate the light source 470 to the mirrors 454, 456 and to the rear pupil of the objective 458. Fluorescence light generated in response to the excitation light from the source 470 can be collected by the objective lens 458 and provided to a wavefront sensor 478 that can be used to determine a wavefront of the fluorescence light, from which sample-induced aberrations in the excitation pathway can be determined. A phase pattern that compensates for the sample-induced aberrations can be determined, and then a total phase pattern can be applied to the WME 452, or the total phase pattern serves both to generate the pattern at the rear pupil of the objective 458 that generates the thin light sheet within the sample and that compensates for the sample-induced aberrations, such aberrations of the thin light sheet within the sample are reduced. Operation of the light sources 451 and 470, the WME 452, the wavefront sensor 478, and the galvanometer mirrors 454, 456 can be controlled by one or more computing system 450.

The detection pathway between the sample 404 and the detector 440 can be similar to the detection pathway between the sample 104 and the detector 140 in FIG. 1A. For example, an excitation light source 402 can provide excitation light to a sample 404, and the excitation light can be modulated by one or more structures between the light source 402 and the sample 404. For example, a Pockels cell 403 can be computer controlled by the computing system 450 to modulate the provision of excitation light from the light source 402 to the sample 404. The sample 404 can be supported by a stage 405. The position of the stage 405 can be moved in orthogonal directions, for example, under computer control by a controller in the computing system 450.

The light source 402 can provide a plane wave of excitation light that can be focused to a focal point within the sample 404 by an objective lens 406. The focal point within the sample can be scanned in directions perpendicular to the axis of the objective 406 by first (X) galvanometer mirror 408 and a second (Y) galvanometer mirror 410. The galvanometer mirrors 408, 410 can be controlled by hardware or software, or a combination of the two, in the computing system 450. The wavefront of the excitation light can be modified by a wavefront modulating element 412 that reflects the beam of excitation light. Each of the first galvanometer mirror 408, the second galvanometer your 410, and the WME 412 can be optically conjugate to the rear pupil of the objective lens 406 by virtue of pairs of lenses 418A, 418B, 420A, 420B, 422A, 422B. The WME 412, both galvos 408, 410, and the objective rear pupil are all mutually conjugate, so the phase pattern from the WME 412 is stationary at the rear pupil of the objective 406, even as the galvos scan the focused excitation light laterally across the sample 404.

In one implementation, the excitation light provided by the light source 402 can have a wavelength that is longer than the wavelength of fluorescence light emitted in response to the excitation light. For example, two photons of light provided by the light source 402 may be required to excite a label within the sample 404 to a state that emits fluorescence light.

Fluorescence light emitted from the sample 404 in response to the focused excitation light can be collected by the objective 406 and reflected off the first and second galvanometer mirrors 408, 410, and a dichroic beamsplitter 430 may reflect light having a wavelength at, or close to, the wavelength of the fluorescence light, while transmitting light having a wavelength at, or close to the wavelength of the excitation light. Fluorescence light collected by the objective 406 and reflected by the first and second galvanometer mirrors 408, 410 can be reflected by the dichroic beamsplitter 430 and then provided to polarizing beamsplitter 432 into two different paths. The polarizing beamsplitter 432 is optically conjugated to the galvanometer mirrors 408, 410, the WME 412, and the rear pupil of the objective 406 by virtue of the lens 434A, 434B. One path of light from the beam splitter is provided to a wavelength sensor 436 (e.g., a Shack-Hartmann sensor) that is configured to measure the wavefront of the fluorescence light and to determine the aberrated wavefront of the emission light. Another path of the light from the beam splitter 432 is reflected from a wavefront modulating element 438 before being focused onto a detector 440 (e.g., a photomultiplier tube). The wavelength sensor 436 and the wavefront modulating element 438 also are optically conjugate to the rear pupil of the objective 406, to the galvanometer mirrors 408, 410 and to the WME 412 by virtue of the mirrors 434A, 434B.

In the configuration shown in FIG. 4, because the fluorescence light emitted from the focal point of the light from light source 402 is de-scanned by the galvanometer mirrors 408, 410 that scan the focal point through the sample, the position of the light provided to the wavefront sensor 436 remains fixed on the wavefront sensor as the focal point of the excitation light is scanned in the sample. The signal on the wavefront sensor 436 can be integrated in time as the focal point of the excitation light is scanned within a volume within the sample 404. Then, a wavefront analysis module within a computing system 410 can be used to determine average aberrations caused by the volume of the sample to outgoing fluorescence light. A wavefront correction module within the computing system 410 can be used to generate a pattern to apply to the wavefront modulating element 438 to compensate for the determined aberrations, over the volume, in the fluorescence light that is received from the sample 404.

Because excitation light for imaging the sample is provided by the excitation pathway (including, for example, the light source 451) and not by the light source 402, in some implementations, the WME 412 can be replaced by a flat mirror.

Thus, the excitation pathway and the detection pathway shown in FIG. 4 can be used in combination with each other, with the excitation pathway providing a thin sheet of excitation light that can be scanned through a small volume within the sample 404. The sample-induced aberrations to the sheet of excitation light within the volume can be compensated by applying an appropriate phase pattern to the WME 452 to optimize the sheet of excitation light that is provided within the sample 404. Similarly, in the detection pathway, wavefront sensor 436 can be used to determine an appropriate phase pattern to apply to WME 438 to compensate for sample-induced aberrations to fluorescence signal light emitted from the volume within sample in response to the sheet of excitation light that is scanned through the volume. The sheet of excitation light can be scanned through the volume, for example, in a direction parallel to the axis of the objective lens 406 and/or in a direction perpendicular to the axes of both objective lens 406 and objective lens 458 (in some configurations, the axes of objective lens 406 and objective lens 458 can be perpendicular to each other). In this manner, an image of the volume of the sample can be generated in which adaptive optics techniques are used to compensate for sample-induced aberrations both to the sheet of excitation light in the volume and to the detected fluorescence light emitted from the volume. This process can be repeated for other volume is in the sample, and an image of the sample can be generated based on the images of the different volumes.

Thin Light Sheets

Figure 5:
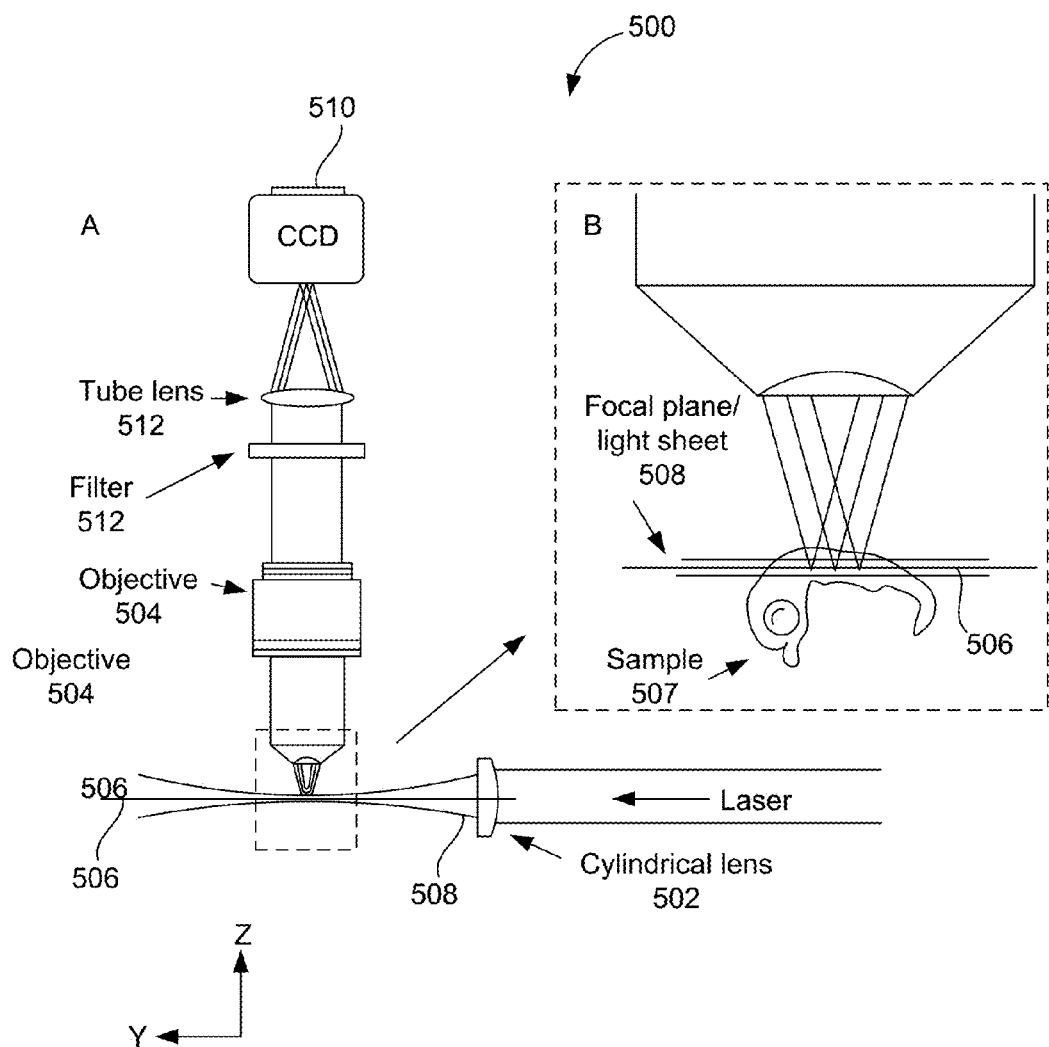
FIG. 5 is a schematic diagram of a light sheet microscopy (LSM) system.

FIG. 5 is a schematic diagram of a light sheet microscopy (LSM) system 500. As shown in FIG. 5, LSM uses a beam-forming lens 502, external to imaging optics, which includes an objective 504, to illuminate the portion of a specimen in the vicinity of the focal plane 506 of the objective. In one implementation, the lens 502 that provides illumination or excitation light to the sample is a cylindrical lens that focuses light in only one direction, thereby providing a beam of light 508 that creates a sheet of light coincident with the objective focal plane 506. A detector 510 then records the signal generated across the entire illuminated plane of the specimen. Because the entire plane is illuminated at once, images can be obtained very rapidly.

In another implementation, termed Digital Laser Scanned Light Sheet Microscopy (DSLM), the lens 502 can be a circularly symmetric multi-element excitation lens (e.g., having a low numerical aperture (NA) objective) that corrects for optical aberrations (e.g., chromatic and spherical aberrations) that are prevalent in cylindrical lenses. The illumination beam 508 of light then is focused in two directions to form a pencil beam of light coincident with the focal plane 506 of the imaging objective 504. The width of the pencil beam is proportional to the 1/NA, whereas its length is proportional to $1/(NA)^2$. Thus, by using the illumination lens 502 at sufficiently low NA (i.e., NA<<1), the pencil beam 508 of the excitation light can be made sufficiently long to encompass the entire length of the desired field of view (FOV). To cover the other direction defining the lateral width of the FOV, the pencil beam can be scanned across the focal plane (e.g., with a galvanometer, as in confocal microscopy) while the imaging detector 510 integrates the signal that is collected by the detection optics 512 as the beam sweeps out the entire FOV.

A principal limitation of these implementations is that, due to the diffraction of light, there is a tradeoff between the XY extent of the illumination across the focal plane of the imaging objective, and the thickness of the illumination in the Z direction perpendicular to this plane. In the coordinate system used in FIG. 5, the X direction is into the page, the Y direction is in the direction of the illumination beam, and the Z direction is in the direction in which imaged light is received from the specimen.

Figure 6:
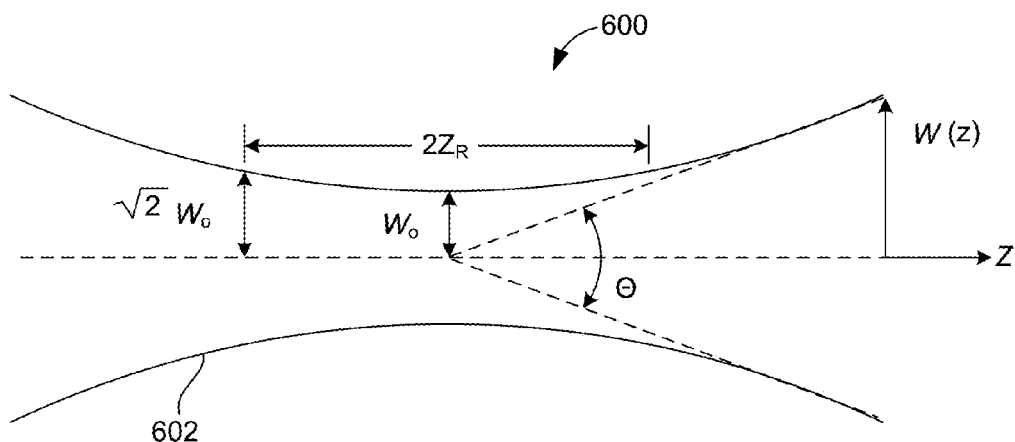
FIG. 6 is a schematic diagram of a profile of a focused beam of light.

FIG. 6 is a schematic diagram of a profile 600 of a focused beam of light. As shown in FIG. 6, illumination light 602 of wavelength, $\lambda$, that is focused to a minimum beam waist, $2w_o$, within the specimen will diverge on either side of the focus, increasing in width by a factor of $\sqrt{2}$ in a distance of $z_R = \pi w_o^2/\lambda$, the so-called Rayleigh range. Table 1 shows specific values of the relationship between the usable FOV, as defined by $2z_R$, and the minimum thickness $2w_o$ of the illumination sheet, whether created by a cylindrical lens, or by scanning a pencil beam created by a low NA objective.

TABLE 1

| $2w_o$ (µm, for $\lambda$ = 500 nm) | $2z_R$ (µm, for $\lambda$ = 500 nm) |
| --- | --- |
| 0.2 | 0.06 |
| 0.4 | 0.25 |
| 0.6 | 0.57 |
| 0.8 | 1.00 |
| 1.0 | 1.57 |
| 2.0 | 6.28 |
| 5.0 | 39.3 |
| 10.0 | 157 |
| 20.0 | 628 |

From Table 1 it can be seen that, to cover FOVs larger than a few microns (as would be required image even small single cells in their entirety) the sheet thickness must be greater than the depth of focus of the imaging objective (typically, <1 micron). As a result, out-of-plane photobleaching and photodamage still remain (although less than in widefield or confocal microscopy, provided that the sheet thickness is less than the specimen thickness). Furthermore, the background from illumination outside the focal plane reduces contrast and introduces noise which can hinder the detection of small, weakly emitting objects. Finally, with only a single image, the Z positions of objects within the image cannot be determined to an accuracy better than the sheet thickness.

This description discloses microscopy and imaging apparatus, systems, methods and techniques, which enable a light sheet or pencil beam to have a length that can be decoupled from its thickness, thus allowing the illumination of large fields of view (e.g., tens or even hundreds of microns) across a plane having a thickness on the order of, or smaller than, the depth of focus of the imaging objective by using illumination beams having a cross-sectional field distribution that is similar to a Bessel function. Such illumination beams can be known as Bessel beams. Such beams are created by focusing light, not in a continuum of azimuthal directions across a cone, as is customary, but rather at a single azimuthal angle or range of azimuthal angles with respect to the axis of the focusing element. Bessel beams can overcome the limitations of the diffraction relationship shown in FIG. 6, because the relationship shown in FIG. 6 is only valid for lenses (cylindrical or objectives) that are uniformly illuminated.

Figure 7:
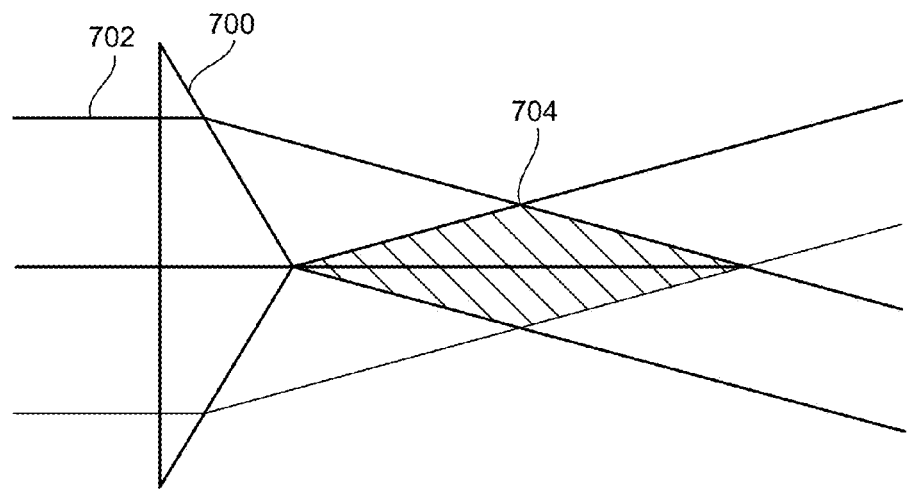
FIG. 7 is a schematic diagram of a Bessel beam formed by an axicon.

FIG. 7 is a schematic diagram of a Bessel beam formed by an axicon 700. The axicon 700 is a conical optical element, which, when illuminated by an incoming plane wave 702 having an approximately-Gaussian intensity distribution in directions transverse to the beam axis, can form a Bessel beam 704 in a beam that exits the axicon.

Figure 8:
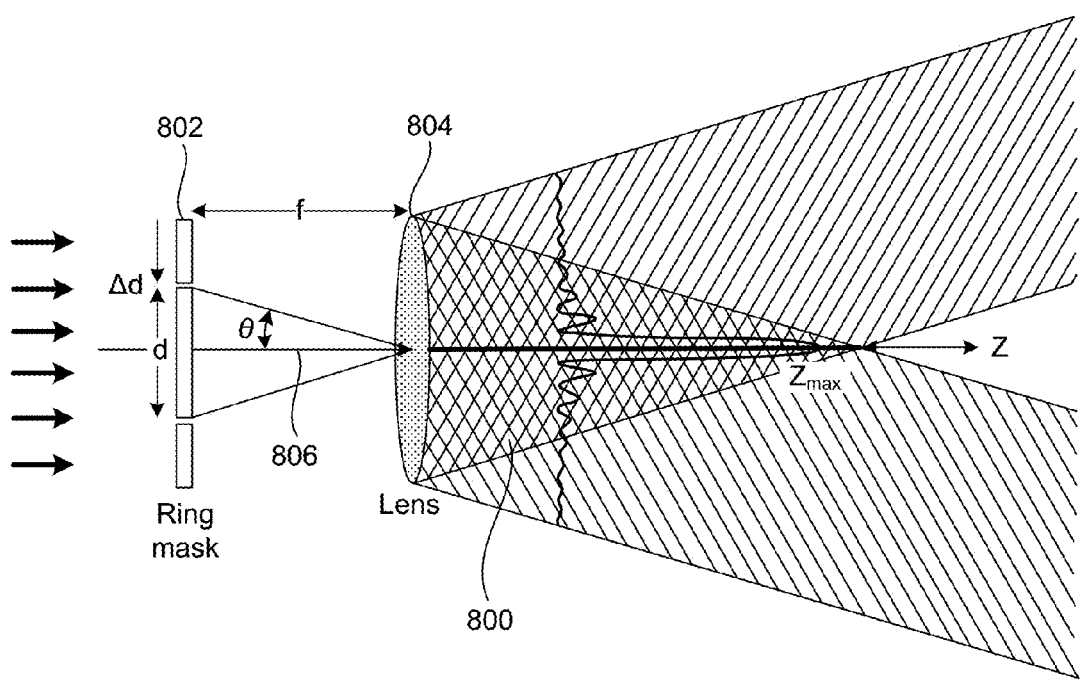
FIG. 8 is a schematic diagram of a Bessel beam formed by an annular apodization mask.

FIG. 8 is a schematic diagram of a Bessel beam 800 formed by an annular apodization mask 802, where the annular mask 802 is illuminated to create a thin annulus of light at the back focal plane of a conventional lens 804. The mask 802 is separated from the lens 804 by the focal length, f. An angle, $\theta$, can be defined as the inverse tangent of half the distance, d, from the center of the annular ring to a point within the ring divided by the focal length, where $d_o$ can be used to denote the minimum diameter of the annular ring. Ideally, in either case shown by FIG. 7 or by FIG. 8, the axial wavevectors $k_z$ of all rays converging to the focus are the same, and hence there is no variation of the beam along this direction. In practice, the finite diameter of the axicon 700, or the finite width, $\Delta d$, of the annular ring in the apodization mask 802 restricts the Bessel beam to a finite length. The optical system of the annular apodization mask 802 and the lens 804 can be characterized by a minimum and maximum numerical aperture, where the maximum numerical aperture is proportional to $d_o + \Delta d$, and the minimum numerical aperture is proportional to $d_o$. In other implementations, different optical elements, other than an axicon or an apodization mask, can be used to create an annulus of light. For example, a binary phase mask or a programmable spatial light modulator can be used to create the annulus of light.

Figure 9:
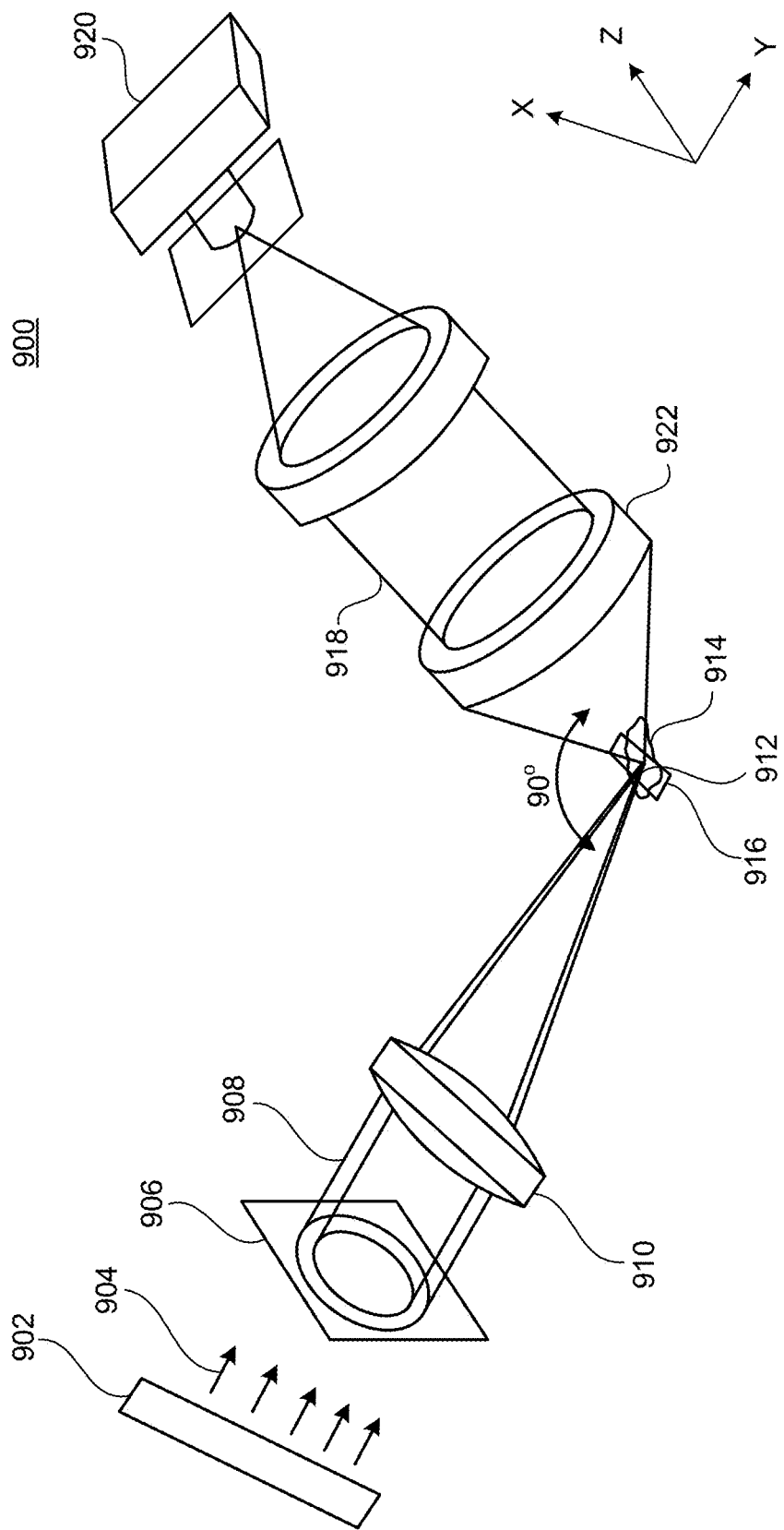
FIG. 9 is a schematic diagram of a system for Bessel beam light sheet microscopy.

FIG. 9 is a schematic diagram of a system 900 for Bessel beam light sheet microscopy. A light source 902 emits a light beam 904 that strikes an annular apodization mask 906. An annulus of excitation light 908 illuminates the back focal plane of microscope objective 910 to create an elongated Bessel beam 912 of light in a sample 914. By scanning this beam in a plane 916 transverse to the axis of the Bessel beam 912 and coincident with the focal plane of a detection objective 904 while simultaneously integrating the collected signal 918 with a camera 920 located at a corresponding image plane of imaging optics 922, an image is obtained from a much thinner slice within the sample than is the case when either conventional light sheet microscopy or DSLM is used.

Figure 10A:
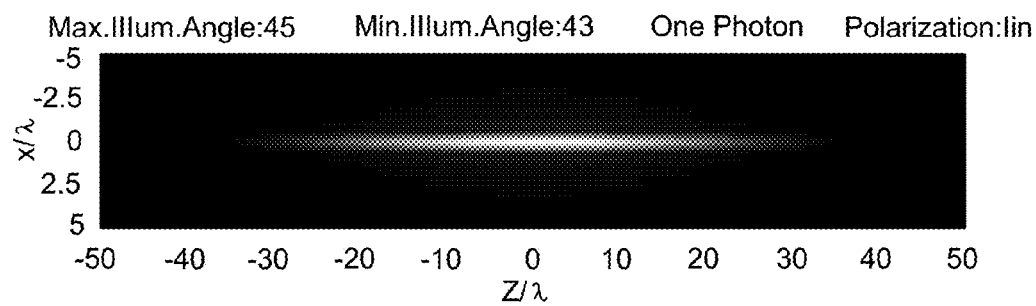
FIG. 10A is a plot of the intensity profile of a Bessel beam.
Figure 10B:
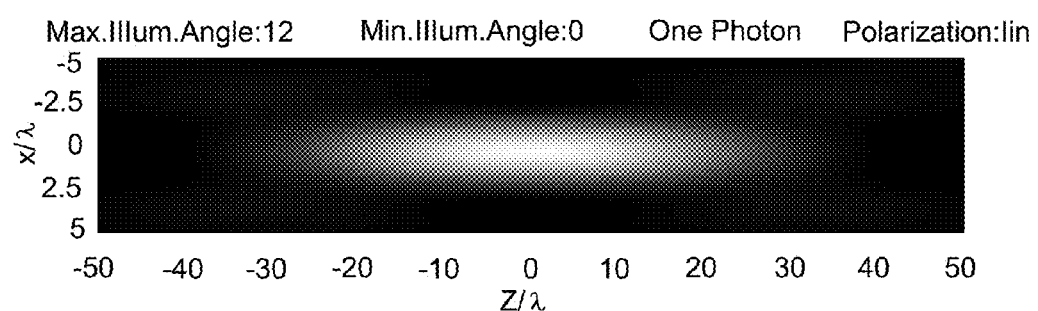
FIG. 10B shows a plot of the intensity profile of a conventional beam.
Figure 11A:
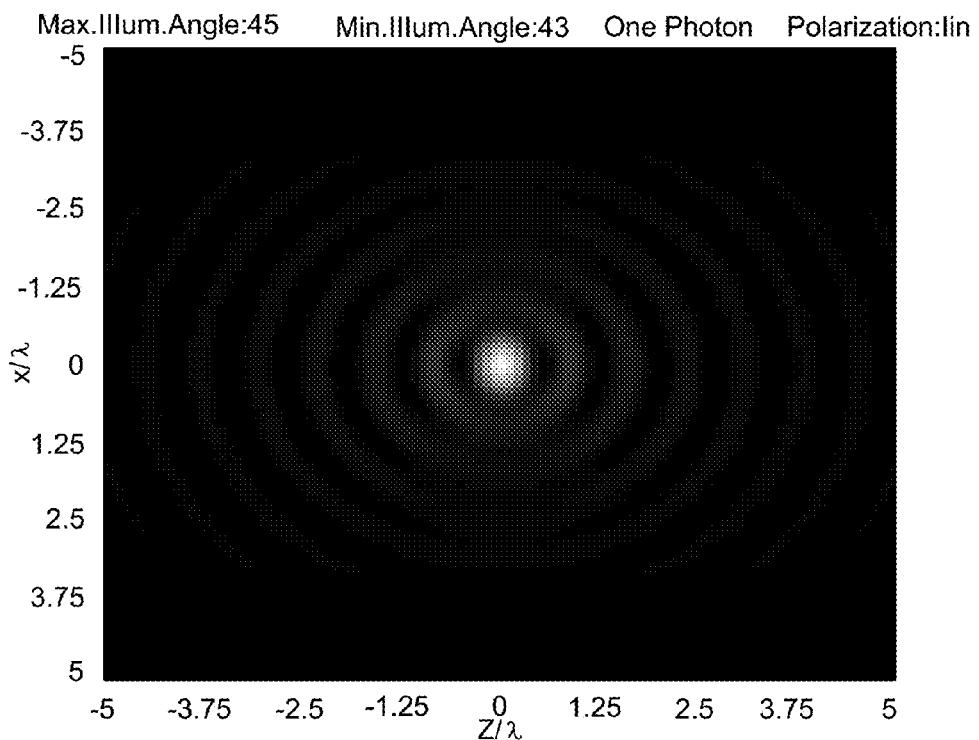
FIG. 11A is a plot of the intensity profile of a Bessel beam of FIG. 10A in the directions transverse to the propagation direction of the beam.
Figure 11B:
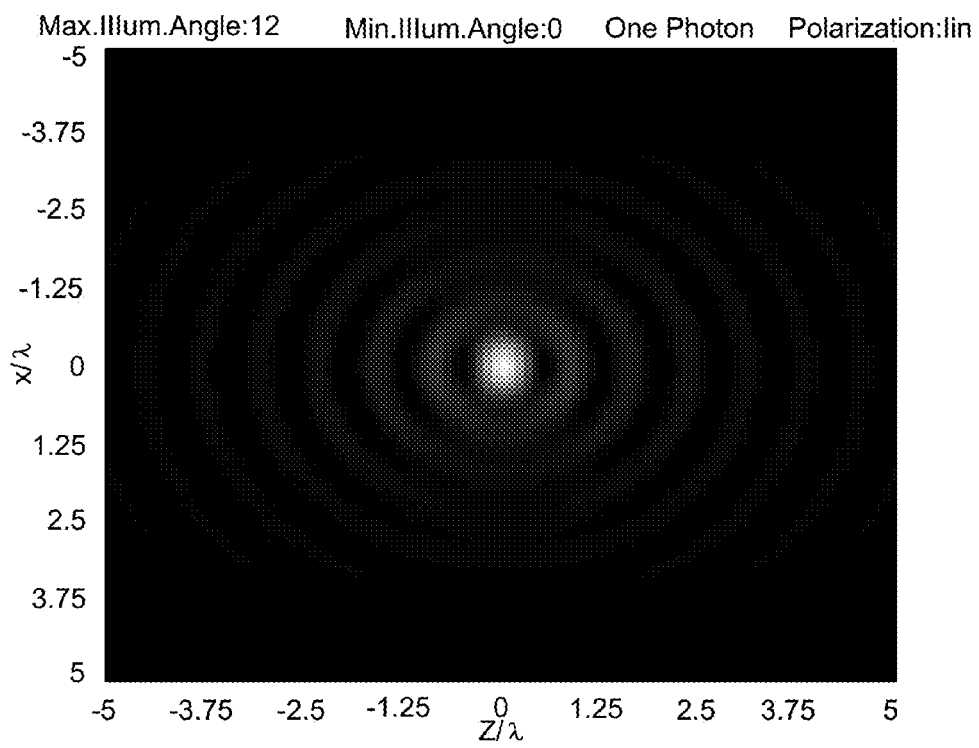
FIG. 11B is a plot of the intensity profile of the conventional beam of FIG. 10B in the directions transverse to the propagation direction of the beam.

How much thinner the sheet of excitation light can be with Bessel beam illumination than with conventional light sheet microscopy or DSLM can be seen from a comparison of FIG. 10A, which shows a plot of the intensity profile of a Bessel beam, and FIG. 10B, which shows a plot of the intensity profile of a conventional beam. In the plots of FIGS. 9 and 10, Y is along the axis of the propagation direction of the beam, X is the direction of the excitation polarization (when linearly polarized light is used), and Z is along the axis of detection optics objective 922 and is orthogonal to X and Y. FIG. 11A is a plot of the intensity profile of a Bessel beam of FIG. 10A in the directions transverse to the propagation direction of the beam, and FIG. 11B is a plot of the Gaussian intensity profile of the conventional beam of FIG. 11A in the directions transverse to the propagation direction of the beam.

As seen in FIG. 10A, annular illumination across a small range of angles ($\theta$=43 to 45 degrees) results in a Bessel-like beam approximately 50 wavelengths $\lambda$ long in the Y direction, or roughly the same length obtained by conventional illumination using a plane wave having a Gaussian transverse intensity profile that is focused by a lens into an illumination beam having a cone half-angle of 12 degrees, as seen in FIG. 10b. However, the thickness of the Bessel beam is much narrower than the thickness of the conventional beam, yielding a much thinner sheet of excitation when scanned across a plane.

Figure 12A:
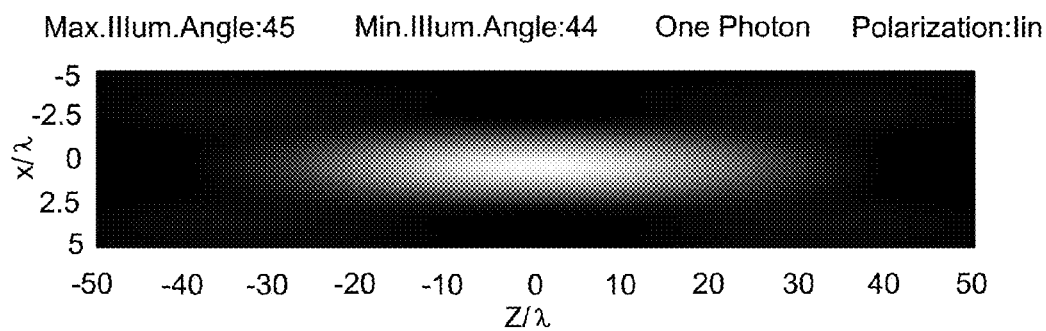
FIG. 12A is a plot of the intensity profile in the YZ plane of a Bessel beam generated from an annular mask having a thinner annulus in the annulus used to generate the intensity profile of the Bessel beam of FIG. 10A.
Figure 12B:
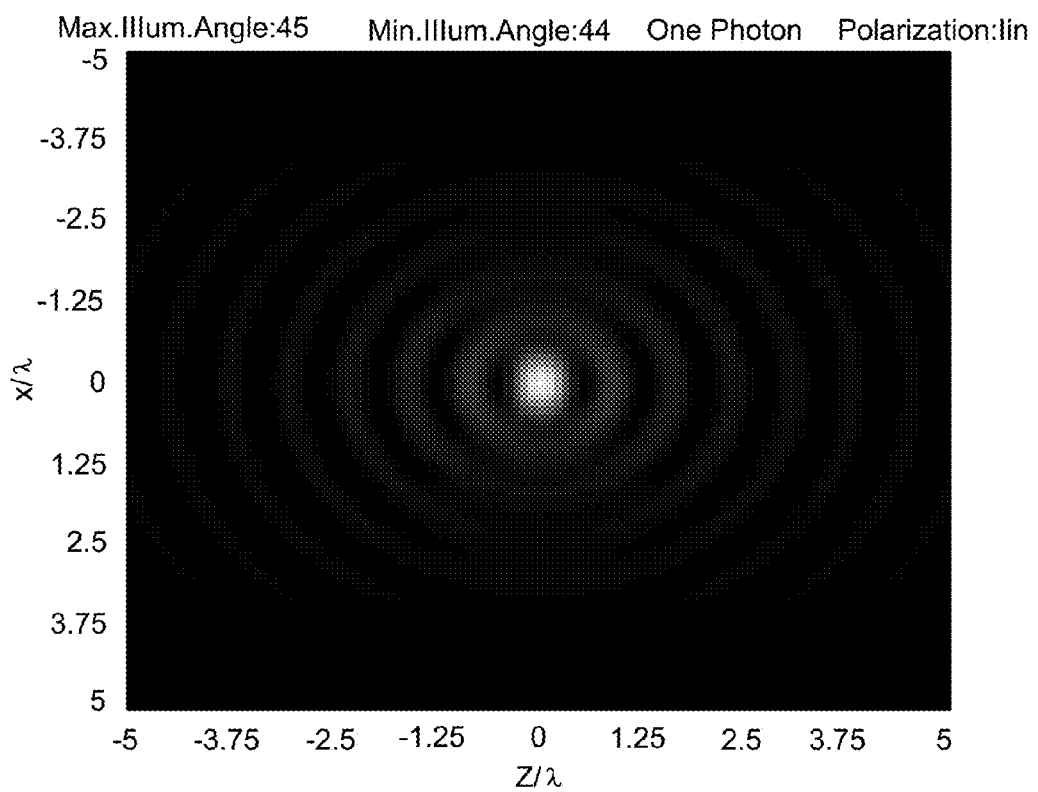
FIG. 12B is a plot of the transverse intensity profile in the XZ directions for the beam of FIG. 12A.

Furthermore, even longer Bessel-like beams can be made without compromising their cross-sectional width simply by restricting the annular illumination over an even smaller range of angles. FIG. 12A is a plot of intensity profile in the YZ directions of a Bessel beam generated from an annular mask having a thinner annulus than is used to generate the intensity profile of the Bessel-like beam of FIG. 10A, and FIG. 12B is a plot of the transverse intensity profile for the beam in the XZ directions. As shown in FIG. 12A, annular illumination across a small range of angles ($\theta$=44 to 45 degrees) results in in the YZ intensity profile of the Bessel-like beam shown in FIG. 12A, where the Bessel-like beam has a length of approximately 100 wavelengths in the Y direction. However, the transverse intensity profile of the longer Bessel beam is relatively unchanged compared with shorter Bessel beam, as can be seen from a comparison of FIG. 11A and FIG. 12B, and the thickness of the beam is not significantly greater than the thickness of the beam whose intensity profile is shown in FIG. 10A. In contrast, with conventional illumination the usual approach of lengthening the beam by reducing the NA results in an unavoidably larger diffraction limited cross-section, roughly in accordance with Table 1.

Figure 13A:
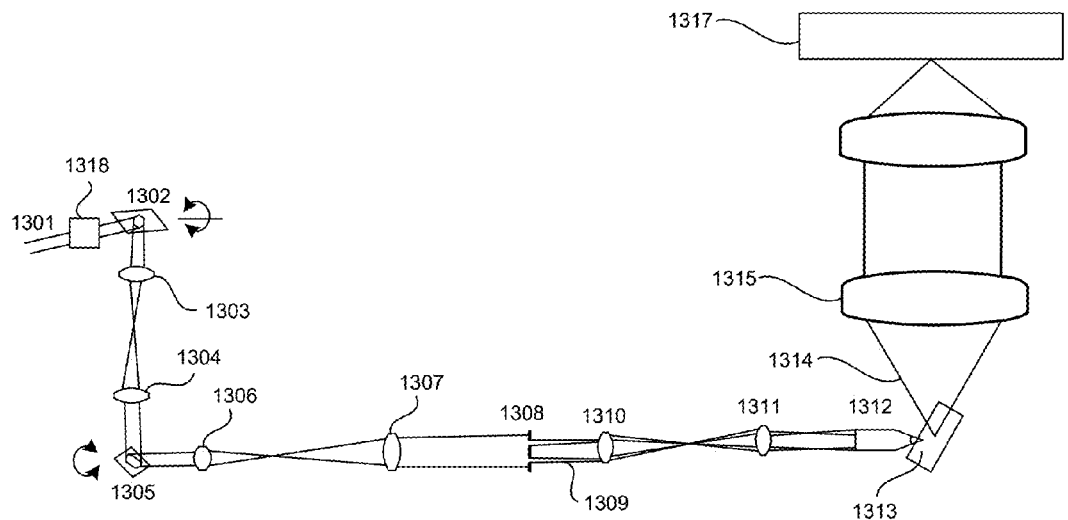
FIG. 13A is a schematic diagram of another system for implementing Bessel beam light sheet microscopy.

FIG. 13A is a schematic diagram of another system 1300 for implementing Bessel beam light sheet microscopy. Collimated light 1301, such as a laser beam having a Gaussian intensity profile, is reflected from first galvanometer-type mirror 1302 and then imaged by relay lens pair 1303 and 1304 onto a second galvanometer-type mirror 1305 positioned at a point optically conjugate to the first galvanometer-type mirror 1302. A second lens pair 1306 and 1307 then relays the light to annular apodization mask 1308 conjugate with the second galvanometer-type mirror 1305. The annular light beam transmitted through this mask 1308 is then relayed by a third lens pair 1310 and 1311 onto a conjugate plane coincident with the back focal plane of excitation objective 1312. Finally, the annular light is focused by objective 1312 to form a Bessel-like beam 1313 that is used to provide excitation light to a specimen.

The rotational axis of galvanometer mirror 1302 is positioned such that tilting this galvanometer-type mirror 1302 causes the Bessel-like beam 1313 to sweep across the focal plane of detection objective 1315 (i.e., in the X direction), whose axis is orthogonal to (or whose axis has an orthogonal component to) the axis of the excitation objective 1312. The signal light 1314 can be directed by detection optics, including the detection objective 1315, to a detection camera 1317. The galvanometers-type mirrors 1302, 1305 can provide sweep rates of up to about 2 kHz, and with resonant galvanometer-type mirrors (e.g., Electro-Optical Products Corp, model SC-30) sweep rates can exceed 30 kHz. Extremely high frame rate imaging is then possible when the system is used in conjunction with a high frame rate detection camera (e.g., 500 frames/sec with an Andor iXon+DU-860 EMCCD, or >20,000 frames/sec with a Photron Fastcam SA-1 CMOS camera coupled to a Hamamatsu C10880-03 image intensifier/image booster).

The rotational axis of the galvanometer mirror 1305 is positioned such that tilting of this mirror causes Bessel-like beam 1313 to translate along the axis of detection objective 1315. By doing so, different planes within a specimen can be accessed by the Bessel beam, and a three dimensional (3D) image of the specimen can be constructed, with much higher axial resolution than in conventional light sheet microscopy, due to the much narrower sheet of excitation afforded by Bessel-like excitation. In order to image each plane in focus, either detection objective 1315 must be moved synchronously with the motion of the Bessel beam 1313 imparted by the tilt of galvanometer-type mirror 1305 (such as with a piezoelectric transducer (e.g., Physik Instrumente P-726)), or else the effective plane of focus of the detection objective 1315 must be altered, such as by using a second objective to create a perfect image of the sample. Of course, if 3D image stacks are not desired, the second galvanometer 1305 and relay lenses 1306 and 1307 can be removed from the system shown in FIG. 13A, and the first galvanometer 1302 and relay lenses 1303 and 1304 can be repositioned so that the apodization mask 1308 is at a conjugate plane relative to galvanometer-type mirror 1302. An acousto-optical tunable filter (AOTF) 1318 can be used to block all excitation light from reaching the specimen when desired.

The system in FIG. 13A is typically quite wasteful of the energy in light beam 1301, because most of this light is blocked by apodization mask 1308. If greater efficiency is desired, a diffractive optical element such as a binary phase mask or spatial light modulator and a collimating lens can be used to create an approximately annular light beam prior to more exact definition of this beam and removal of higher diffractive orders by the apodization mask 1308.

Figure 13B:
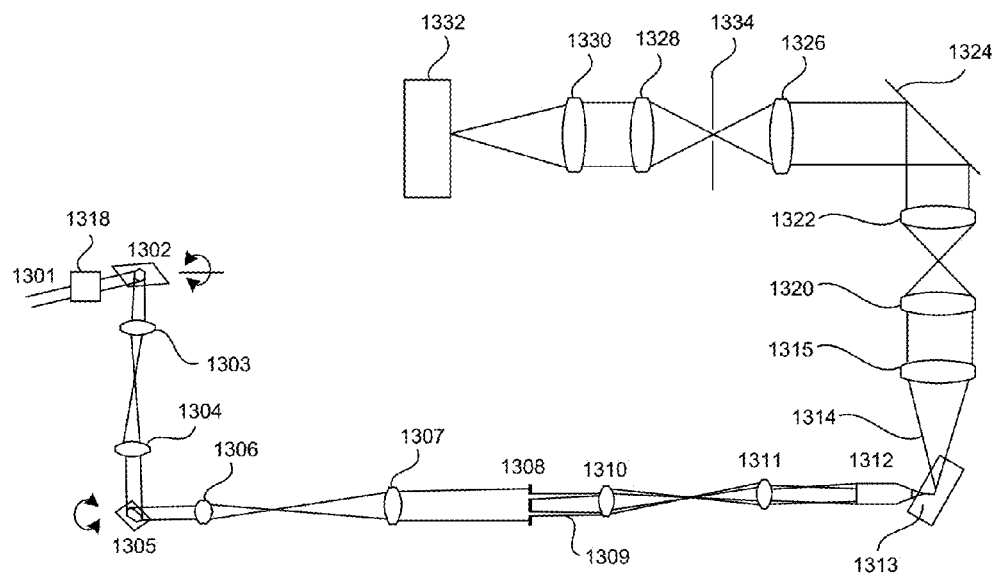
FIG. 13B is a schematic diagram of another system for implementing Bessel beam light sheet microscopy.

In another implementation, shown in FIG. 13B, signal light 1314 received by detection objective 1315 can be transmitted through relay lenses 1320, 1322 and reflected off a galvanometer-type mirror 1324 and then transmitted through relay lenses 1326 and 1328 and focused by a tube lens 1330 onto a detector 1332. An aperture mask (e.g., an adjustable slit) 1334 can be placed at a focal plane of lens 1326, and the when the mask defines a slit the width of the slit 1334 can be selected to block signal light from positions in the sample corresponding to side lobes of the Bessel-like beam illumination light, while passing signal light from positions in the sample corresponding to the central peak of the Bessel-like beam illumination light. The galvanometer-type mirror 1324 can be rotated in conjunction with galvanometer-type mirror 1302, so that when the Bessel-like beam is scanned in the X direction within the sample signal light from different positions within the sample passes through the slit 1334.

Figure 14:
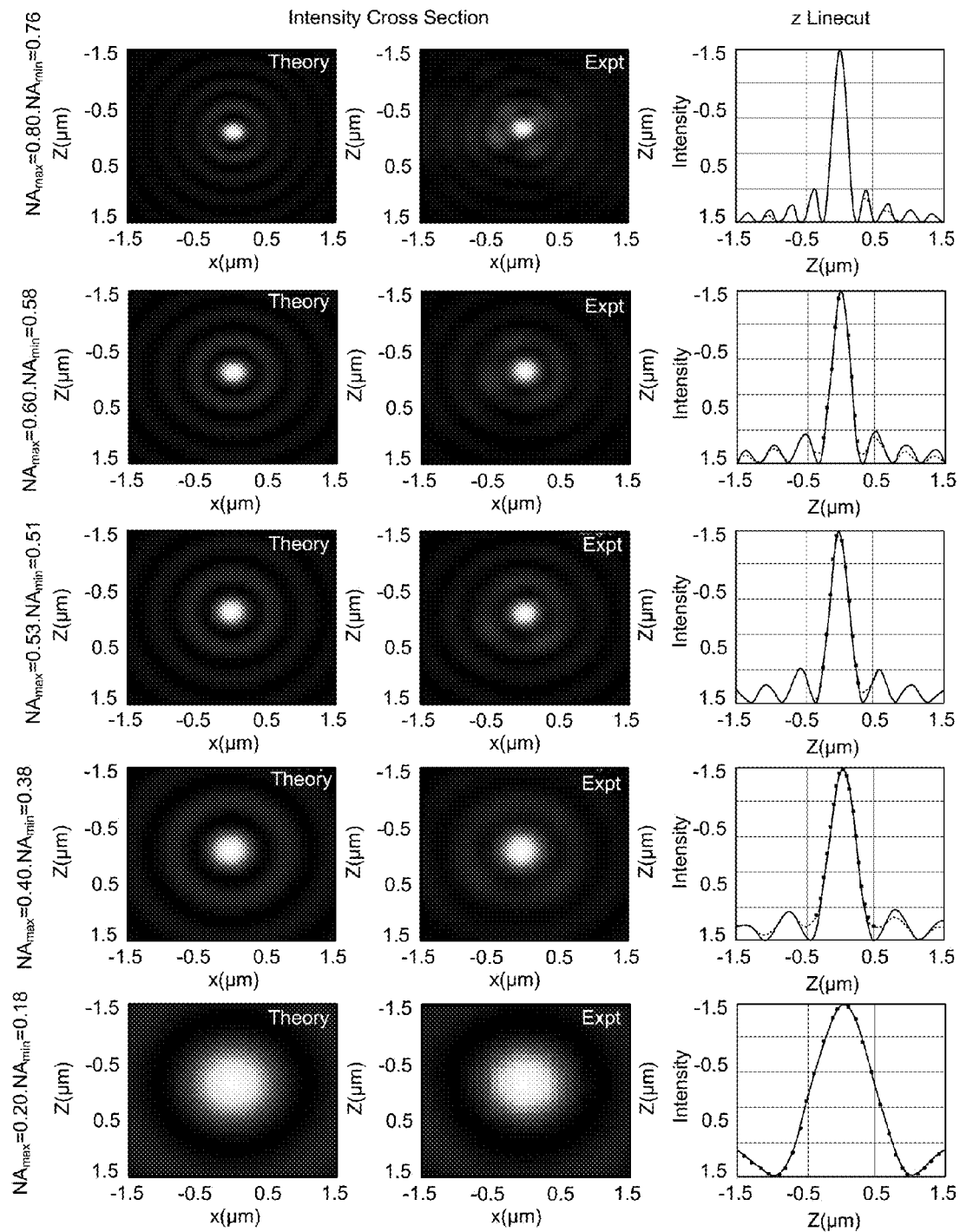
FIG. 14 shows a number of transverse intensity profiles for different Bessel-like beams.

Bessel-like beams include excitation intensity in rings other than the central excitation maximum, which are evident in FIGS. 11A and 12B, and substantial energy resides in the side lobes of a Bessel-like beam. Indeed, for an ideal Bessel beam of infinite extent, each side lobe contains energy equal to that in the central peak. Also, for an ideal Bessel beam, the ratio of the Rayleigh length of the beam to the minimum waist size of the beam is infinite. FIG. 14 shows a number of transverse intensity profiles for different Bessel-like beams. In FIG. 14, the first column shows theoretical two-dimensional intensity plots in the XZ plane, the second column shows experimental intensity plots in the third column shows a one-dimensional intensity profile at the X=0 plane. Different rows in FIG. 14 correspond to Bessel-like beams that are created using different annular apodization masks. Each row indicates the maximum and minimum numerical aperture of the annular ring of the mask. In the first row, the maximum numerical aperture is 0.80, and the minimum numerical aperture is 0.76. In the second row, the maximum numerical aperture is 0.60, and the minimum numerical aperture is 0.58. In a third row, the maximum numerical aperture is 0.53 and the minimum numerical aperture is 0.51. In the fourth row the maximum numerical aperture is 0.40, and the minimum numerical aperture is 0.38. In the fifth row, the maximum numerical aperture is 0.20, and the minimum numerical aperture is 0.18.

Figure 15A:
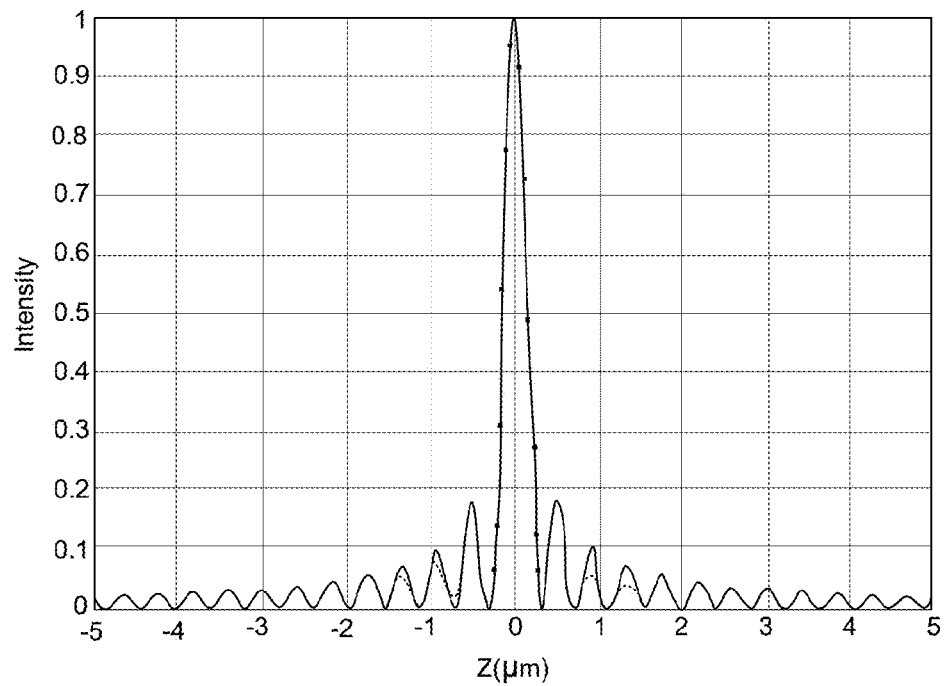
FIG. 15A shows the theoretical and experimental one-dimensional intensity profile of a Bessel-like beam at the X=0 plane.
Figure 15B:
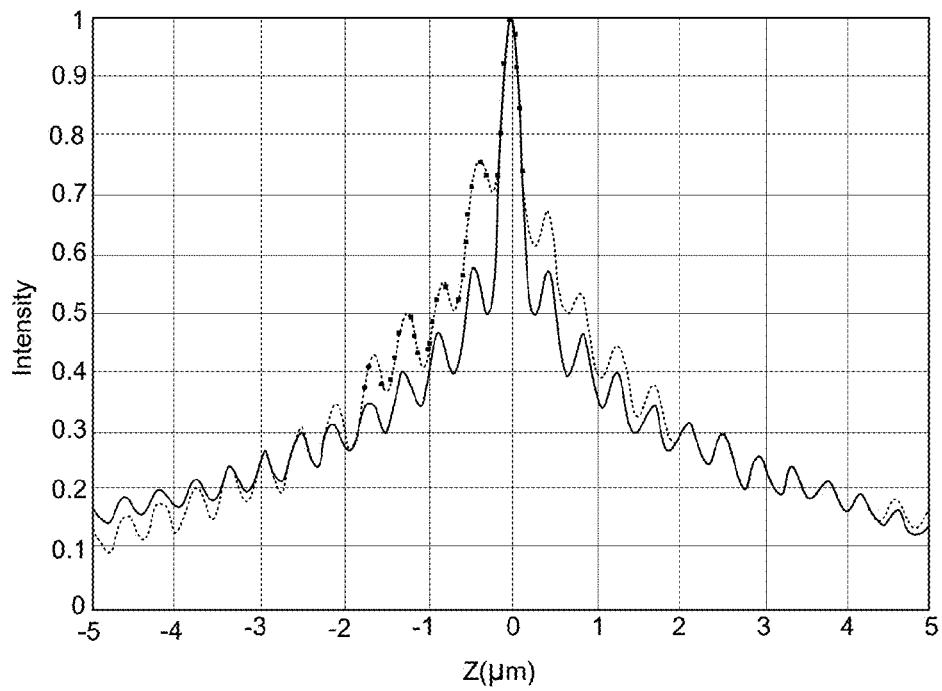
FIG. 15B shows an integrated intensity profile when the Bessel beam of FIG. 15 A is swept in the X direction.

Because of the intensity in the side lobes, the integrated fluorescence excitation profile after the beam is swept in the X direction exhibits broad tails, as shown in FIG. 15. FIG. 15A shows the theoretical and experimental intensity profile in the Z direction of a Bessel-like beam, when the center of the beam is fixed at the X=0 and Z=0 plane, where experimental values are shown by dots and theoretical values are shown by solid lines. The intensity profile shown in FIG. 15A is representative of a Bessel-like beam formed from an annular apodization mask that generates an annulus of 488 nm light at a rear pupil of an excitation objective, where the annulus has a maximum numerical aperture of 0.60 and a minimum numerical aperture of 0.58. When this Bessel-like beam is swept in the X direction to create a sheet of excitation light centered on the Z=0 plane, integrated fluorescence excitation profile shown in FIG. 15B results because of the side lobes in the beam. Thus, the side lobes of the Bessel beam can contribute out-of-focus background fluorescence and premature photobleaching of the sample. A number of techniques can be used to mitigate the effect of these lobes.

Figure 16A:
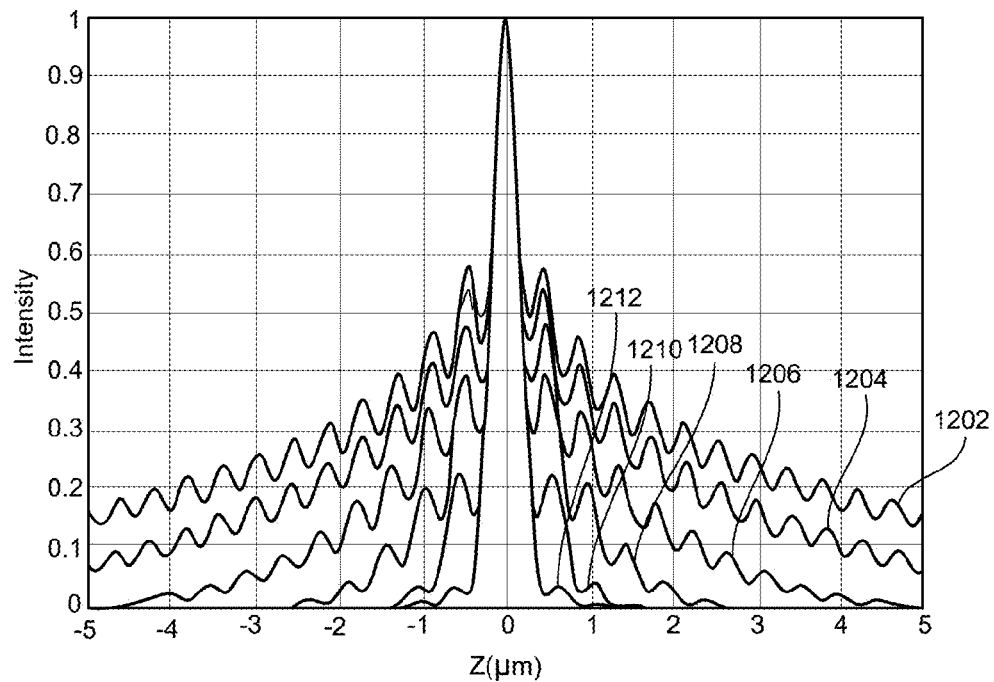
FIG. 16A shows plots of the width of fluorescence excitation profiles of a swept beam, where the beam that is swept is created from annuli that have different thicknesses.
Figure 16B:
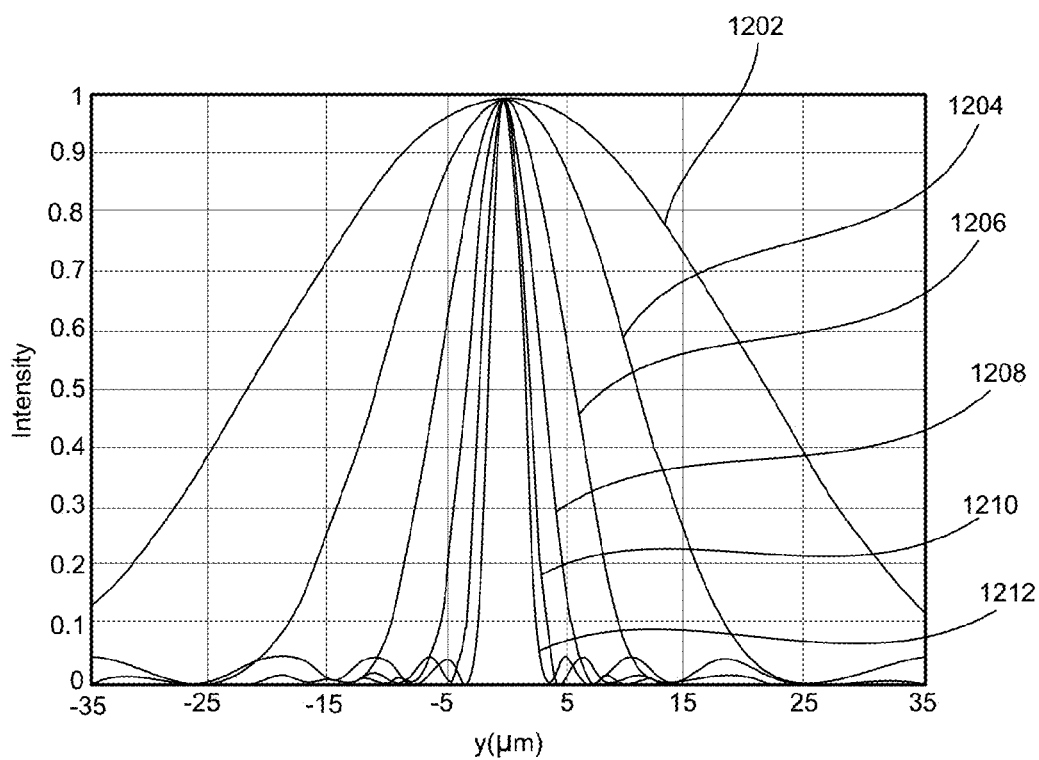
FIG. 16B shows plots of the axial intensity profile of the beam that is swept in the Z direction.

Choosing a thicker annulus in the annular mask 906 suppresses these tails, but it does so at the expense of the length of the beam, as the beam becomes more Gaussian and less Bessel-like in character. This effect can be seen in FIG. 16A and FIG. 16B. FIG. 16A shows plots of the width of fluorescence excitation profiles of beams swept in the X direction in the Z=0 plane, where the beams that are swept are created from annuli that have different thicknesses. FIG. 16B shows plots of the axial intensity profiles (i.e., in the Y direction) of the beams that are swept. For each of the beams whose intensity profiles are plotted in FIG. 16A and FIG. 16B, the maximum numerical aperture is 0.60. A beam with an intensity profile 1602 has a minimum numerical aperture equal to 0.58. A beam with an intensity profile 1604 has a minimum numerical aperture equal to 0.56. A beam with an intensity profile 1606 has a minimum numerical aperture people equal to 0.52. The beam with an intensity profile 1608 has a minimum numerical aperture equal to 0.45. A beam with an intensity profile 1610 has a minimum numerical aperture equal to 0.30. A beam with an intensity profile 1612 as a minimum numerical aperture equal to 0.00, i.e., it is equivalent to the Gaussian beam that fully illuminates a circular aperture.

Thus, as can be seen from a comparison of the plot FIG. 16A and FIG. 16B, a trade-off exists between minimizing the deleterious effects of the side lobes of the beam and maximizing the axial length of the field of view of the beam. Therefore, by selecting an annulus having a thickness that achieves a length of the field of view that is just sufficient to cover a region of interest in a specimen, but that is not substantially longer than the region of interest, the deleterious effects of the side lobes can be minimized. Therefore, the system 900 shown in FIG. 9, can include a plurality of different apodization masks 906 in which the thickness of the open annular region varies, and a particular one of the apodization masks 906 can be selected to image a region of the specimen 914, where the selected mask is chosen such that the length of the field of view of beam just covers the region of interest. When referring to FIG. 8, the different apodization masks can have open regions with different widths, $\Delta d$.

Thus, a comparison of the plots in FIG. 16A and FIG. 16B shows the profiles of the beam changing from a profile that best approximates that of a lowest order ($J_O$) Bessel function (plot 1602) to a Gaussian profile (1212). This comparison indicates that the deleterious effect of the side lobes can be reduced by using a beam having a profile that is not substantially similar to that of a Bessel function, at the expense of having a beam with a shorter axial length. This means that it can be advantageous to select a beam profile having a minimum length necessary to create the desired image, so that the effect of the side lobes of the beam, which create background haze and photobleaching, can be minimized. Thus, the beam that may be selected may not have a profile that approximates that of a Bessel function, but the beam also may not have a profile of a Gaussian beam, because the annular mask 906 blocks the portion of the incoming light 904 on the axis of the excitation objective 910 such that the $k_z=0$ of the beam 916 are removed. In particular, in one implementation, the selected beam can have a ratio of a Rayleigh length, $z_R$ to a minimum beam waist, $w_o$, of more than $2\pi w_o/\lambda$ and less than $100\pi w_o/\lambda$. In another implementation, the selected beam can have a non-zero ratio of a minimum numerical aperture to a maximum numerical aperture of less than 0.95. In another implementation, the selected beam can have a non-zero ratio of a minimum numerical aperture to a maximum numerical aperture of less than 0.9. In another implementation, the selected beam can have a ratio of a minimum numerical aperture to a maximum numerical aperture of less than 0.95 and greater than 0.80. In another implementation, the selected beam can have a non-zero ratio of a minimum numerical aperture to a maximum numerical aperture of less than 0.9. In another implementation, the selected beam can have a ratio of a minimum numerical aperture to a maximum numerical aperture of less than 0.95 and greater than 0.80. In another implementation, the selected beam can have a ratio of energy in a first side lobe of the beam to energy in the central lobe of the beam of less than 0.5.

The length of the beam 916 that is necessary to image a specimen can be reduced by tilting a cover slip that supports the specimen with respect to the direction of the incoming beam 916. For example, if a specimen that resides on a cover slip is 5 μm thick in the direction normal to the cover slip and has lateral dimensions of 50 μm×50 μm then, if the cover slip lies in the Z=0 plane, the beam 916 would have to be 50 μm long to span the specimen. However, by tilting the plane of the cover slip at a 45° angle to the direction of the incoming beam 916, then the beam would only need to be 5 μm×√2 long to span the sample. Thus, by placing a thin specimen on a cover slip and tilting the cover slip with respect to the direction of the incoming beam, a shorter length beam can be used, which has the advantage of reducing the effect of background haze and photobleaching due to side lobes of the beam. To image the specimen on a tilted cover slip, the beam 916 can be scanned in the X direction by tilting the galvanometer-type mirror 1302, and can be scanned in the Z direction either by introducing a third galvanometer (not shown) and a third pair of relay lenses (not shown) into the system 1300 shown in FIG. 13A to scan the beam 916 in the Z direction or by translating the Z position of the specimen, e.g., via a piezoelectric transducer (not shown and FIG. 13A) coupled to the cover slide that supports the specimen. This mode of operation in which a specimen on a cover slip is imaged when the cover slip is tilted (e.g., at an angle between 10 and 80 degrees) with respect to the direction of the incoming illumination beam can be used to image thin (e.g., less than 10 µm thick) specimens, such as individual cells that are mounted or cultured on to the cover slip.

Another approach to isolate the central peak fluorescence from that generated in the side lobes is to exclude the latter via confocal filtering with a virtual slit. When the detector includes a plurality of individual detector elements, only those elements of the detector which an image the portion of the sample that is illuminated by the central lobe of the illumination beam can be activated to record information that is used to generate an image, while the individual detector elements upon which an image of the portion of the sample that is illuminated by side lobes of the illumination beam are not activated, such that they do not record information that is used to generate an image.

Figure 17A:
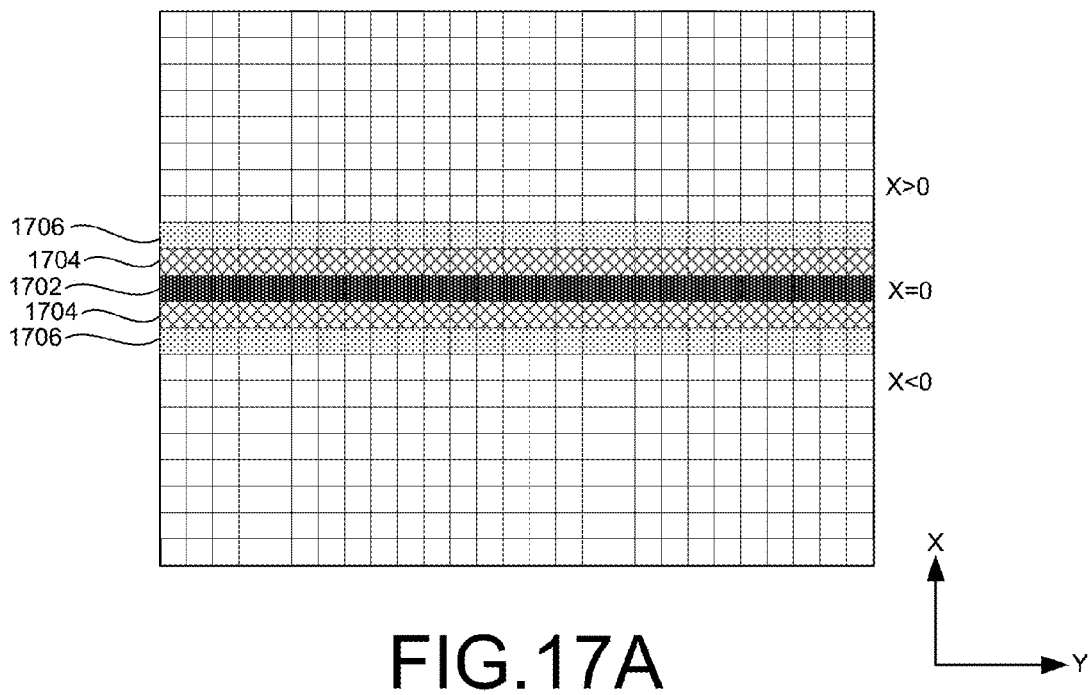
FIG. 17A is a schematic diagram of a surface of a detector having a two-dimensional array of individual detector elements in the X-Y plane.

For example, FIG. 17A is a schematic diagram of a surface of a detector having a two-dimensional array of individual detector elements in the XY plane. When the center of the central lobe of the excitation beam is located at X=0 and side lobes are located at X>0 and X<0, then the detector elements 1702 onto which fluorescence or detection light is focused from the X=0 position within the specimen at the focal plane of the detection objective 1315 (or detector elements corresponding to the smallest absolute value of X for a particular Y position) can be activated to record information, while neighboring detector elements corresponding to higher absolute values of X for the particular Y position can be un-activated such that they do not record information that is used to generate an image. As shown in FIG. 17A, detector elements 1702 located on the detector surface at positions that correspond most closely with fluorescence light from X=0 positions within the specimen can be activated to record information, while neighboring detector elements 1704, 1706 are unactivated, so they do not record fluorescence light from positions within the sample that are not illuminated by the central portion of the excitation beam.

Figure 17B:
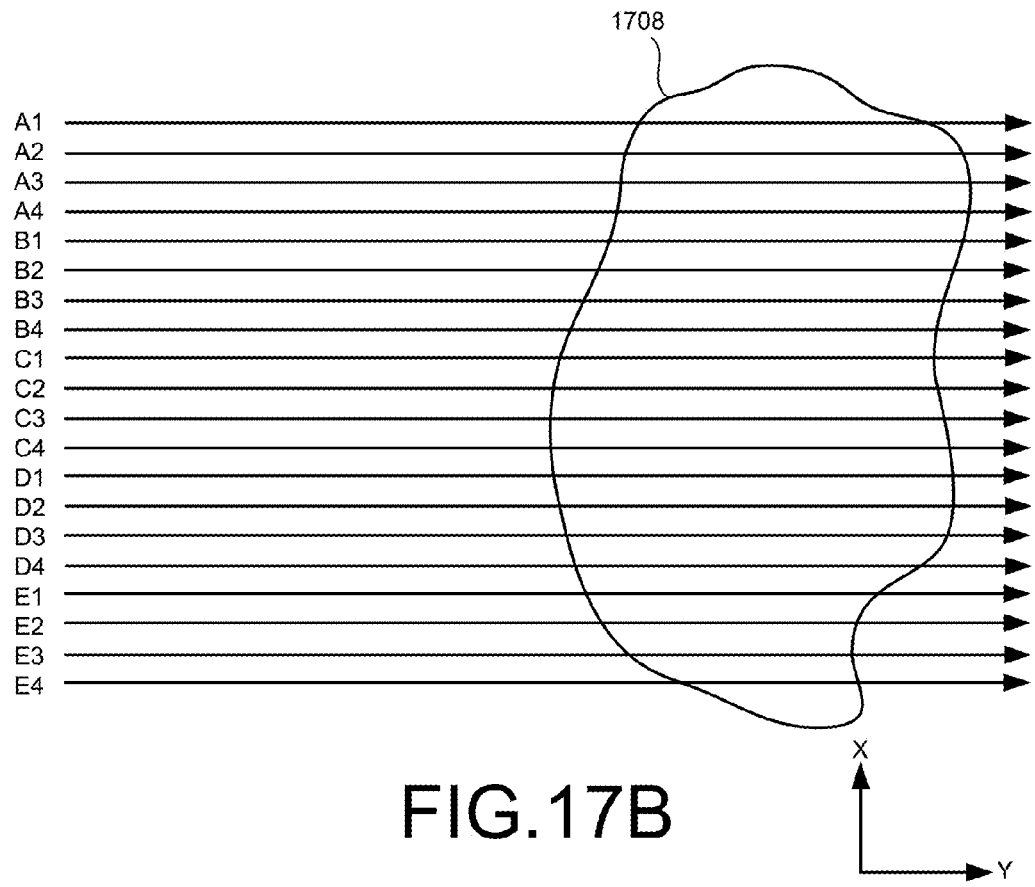
FIG. 17B is a schematic diagram of "combs" of multiple Bessel-like excitation beams that can be created in a given Z plane, where the spacing in the X direction between different beams is greater than the width of the fluorescence band generated by the side lobes of the excitation beams.

FIG. 17B is a schematic diagram of "combs" of multiple Bessel-like excitation beams that can be created in a given Z plane. A comb of beams can be created by inserting a diffractive optical element (DOE, not shown) in the beam path between the light source and the galvanometer-type mirrors 1302, 1305, where the DOE diffracts a plurality of beams at different angles from the DOE, which end up being parallel to and spatially shifted from each other within the specimen. In the specimen at the focal plane of the detection objective, the spacing in the X direction between different beams of the comb is greater than the width of the fluorescence band generated by the side lobes of the beams. This allows information to be recorded simultaneously from rows of individual detector elements corresponding to the centers of the different beams of the comb, without the side lobes of neighboring beams interfering with the recorded signal for a particular beam.

For example, as shown in FIG. 17B, a comb of beams that illuminate a plane of a specimen 1708 can include the beams A1, B1, C1, D1, and E1, where the beams are separated by distances great enough so that side lobes of one beam in the comb do not overlap with a central portion of a neighboring beam. In this manner, multiple "stripes" of an image can be simultaneously recorded. This process is then repeated, with additional images collected as the comb of Bessel-like illumination beams is translated in discrete steps having a width that corresponds to the spacing in the X direction between individual detector elements until all "stripes" of the final image have been recorded. For example, the beams can be moved to new positions of A2, B2, C2, D2, and E2, where the spacing between the positions A1 and A2, the spacing between positions B1 and B2, etc. corresponds to the spacing between neighboring individual detector elements in the detector. Thus, fluorescence light from the beam position C1 could be detected at a detector element 1702, while fluorescence light from the beam position C2 can be detected at individual detector elements 1704. The image is then digitally constructed from the information in all of the different stripes of the image. An acousto-optical tunable filter (AOTF) 1318 can be used to block all excitation light from reaching the specimen between steps.

Another technique to reduce the influence of the side lobes and to reduce the Z-axis size of the field of view from which detection light is received is to employ structured illumination (SI) based optical sectioning. In a widefield microscopy implementation of SI, a periodic excitation pattern can be projected through an epi-illumination objective to the focal plane of the objective, and three images of a sample, $I_n$ (n=1,2,3), are acquired as the pattern is translated in steps of ⅓ of the period of the pattern. Since the observable amplitude of the pattern decreases as it becomes increasingly out of focus (i.e., in a direction perpendicular to the focal plane), combining the images according to:

$$I_{final} = \left| \sum_{n=1}^{N} I_n \exp(2\pi i n / N) \right| \quad (1)$$

with N=3 removes the weakly modulated out-of-focus component and retains the strongly modulated information near the focal plane. In equation (1), I is an intensity at a point in the image, and n is an index value indicating an image from which $I_n$ is taken. Equation (1) is but one example of a linear combination of the individual images that will remove the weakly modulated out-of-focus component and retain the strongly modulated information near the focal plane.

To use SI using a Bessel-like beam with a wavelength, X, that illuminates a thin plane of a specimen and where light is emitted in a direction perpendicular to (or in a direction with a component perpendicular to the illumination plane, the beam may not be swept continuously, but rather can be moved in discrete steps to create a pattern of illumination light from which an image $I_n$ can be generated. When the stepping period is larger than or approximately equal to the minimum period of $\lambda/2NA_{Bessel}^{max}$ required to produce a resolvable grating, but smaller than or approximately equal to $\lambda/NA_{Bessel}^{max}$, the imposed pattern of illumination light contains a single harmonic, as required for the three-image, three-phase SI algorithm.

Thus, referring to FIG. 13A, the Bessel-like beam 1313 can be moved across the X direction in discrete steps having a period greater than or approximately equal to $\lambda/2NA_{Bessel}^{max}$ and less than or approximately equal to $\lambda/NA_{Bessel}^{max}$ by controlling the position of the galvanometer-type mirror 1302, and detection light can be received and signals corresponding to the detected light can be recorded by the detector 1317 when the beam 1313 is in each of the positions. While the galvanometer-type mirror is being moved from one position to the next position, the illumination light can be blocked from reaching the sample by the AOTF. In this manner, an image h can be generated from the detected light that is received when the illumination beam 1313 is at each of its different positions. Then, additional images, $I_2 \ldots I_N$, can be created by again stepping the beam 1313 across the specimen in the X direction to create a pattern of illumination light, but with the patterns spatially shifted from the position of the first pattern by (i-1)/N of the period of the pattern, for i=2 to N. A final image of the specimen then can be constructed from the recorded signals through the use of equation (1).

Figure 18A:
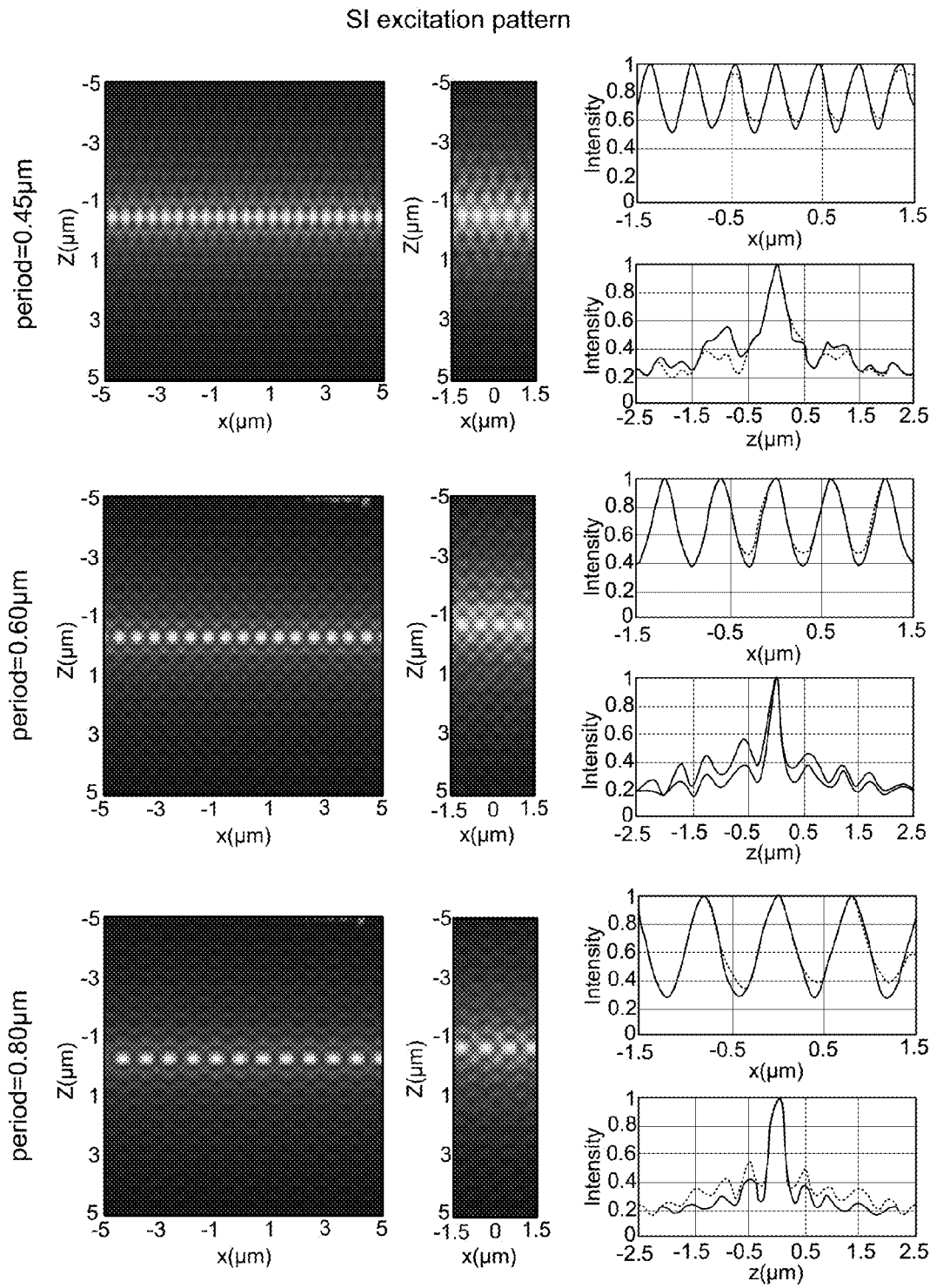
FIG. 18A shows theoretical and experimental single-harmonic structured illumination patterns that can be created with Bessel-like beams having a maximum numerical aperture of 0.60 and the minimum vertical aperture of 0.58, which are created with 488 nm light.
Figure 18B:
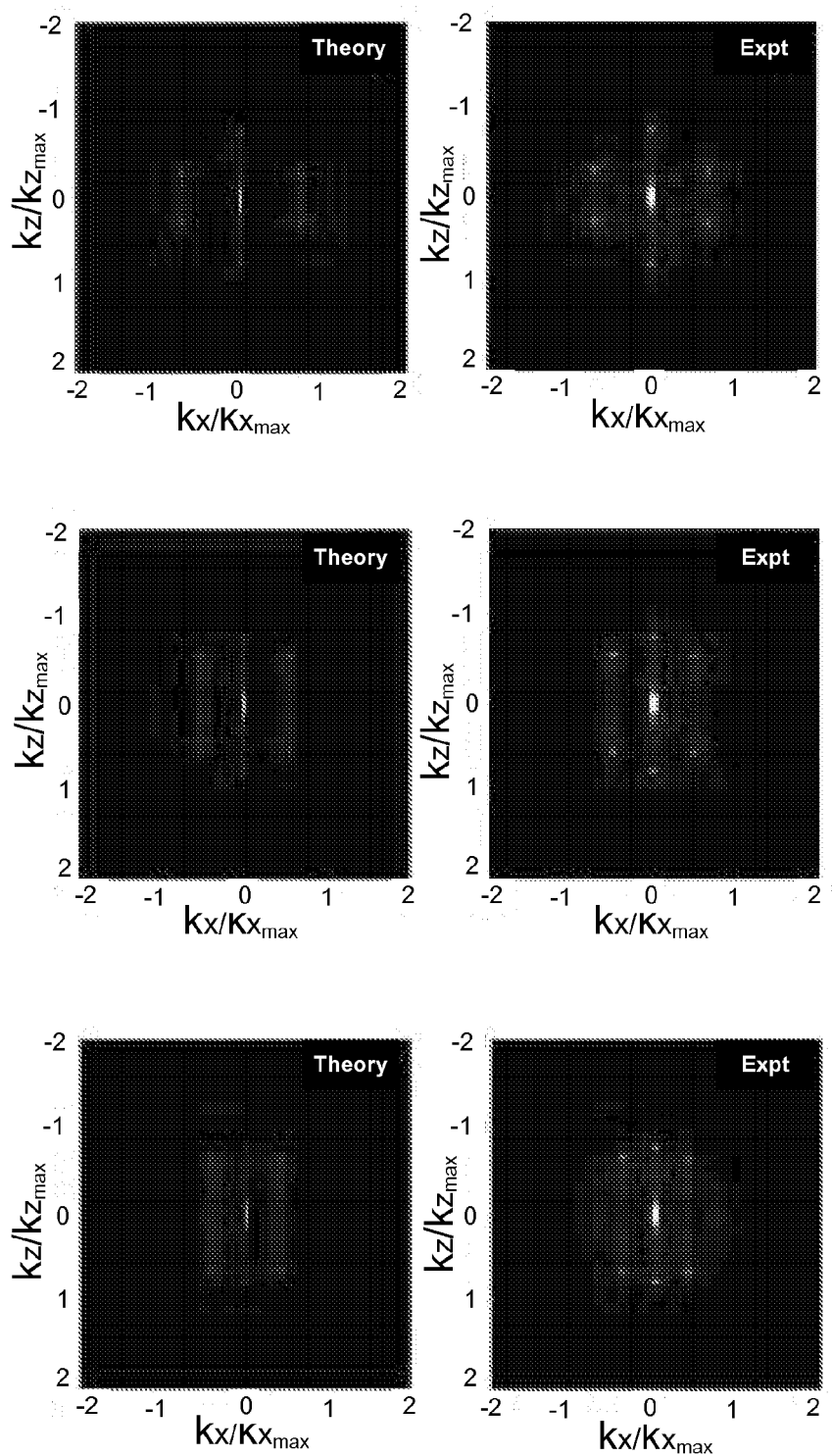
FIG. 18B shows theoretical and experimental modulation transfer functions in reciprocal space, which correspond to the point spread functions shown in the two left-most columns of FIG. 18A.

FIG. 18A shows theoretical and experimental structured illumination patterns that can be created with a 488 nm light Bessel-like beam having a maximum numerical aperture of 0.60 and the minimum numerical aperture of 0.58, that is moved across the X direction in discrete steps. The leftmost column of figures shows theoretical patterns of the point spread functions of the excitation light produced by stepping the beam across the X direction in discrete steps. The middle column shows experimentally-measured patterns, and the third column shows one-dimensional intensity patterns for the Z=0 plane (top figure) and the X=0 (bottom figure) plane, respectively, in each of the three rows of FIG. 18A. In the first row of FIG. 18A, the period the pattern (i.e., the spacing between successive positions of the center of the Bessel-like being as the beam is stepped in the X direction) is 0.45 µm. In the second row, the period of the pattern is 0.60 µm. In the third row the period of the pattern is 0.80 µm. FIG. 18B shows theoretical and experimental modulation transfer functions (MTFs) in reciprocal space, which correspond to the point spread functions shown in the two left-most columns of FIG. 18A. All of the MTFs are normalized to the maximum frequency, $k_{max}=2NA_{exc}^{max}/\lambda$ set by Abbe's Law, with $NA_{exc}^{max}=0.8$ for the excitation objective.

As described above, rather than stepping a single beam across the X direction, a comb of multiple Bessel-like beams, which are spaced by more than the width of the fringes of the beams in the comb, can be used to illuminate the specimen simultaneously, and then the comb of beams can be stepped in the X direction using the step size described above, so that different stripes of the specimen can be imaged in parallel and then an image of the specimen can be constructed from the multiple stripes.

The excellent optical sectioning of the single harmonic SI mode results from the removal of the $k_x=0$ band in the excitation modulation transfer function (MTF) under application of Eq. (1). However, due to the energy in the Bessel side lobes, considerably more spectral energy exists in this band than in the two side bands, so that its removal proves wasteful of the photon budget and reduces the SNR of the final images substantially. Somewhat more energy can be transferred to the side bands using single harmonic excitation having a period far beyond the $\lambda/2NA_{detect}^{max}$ Abbe limit, but at the expense of proportionally poorer optical sectioning capability.

Figure 19A:
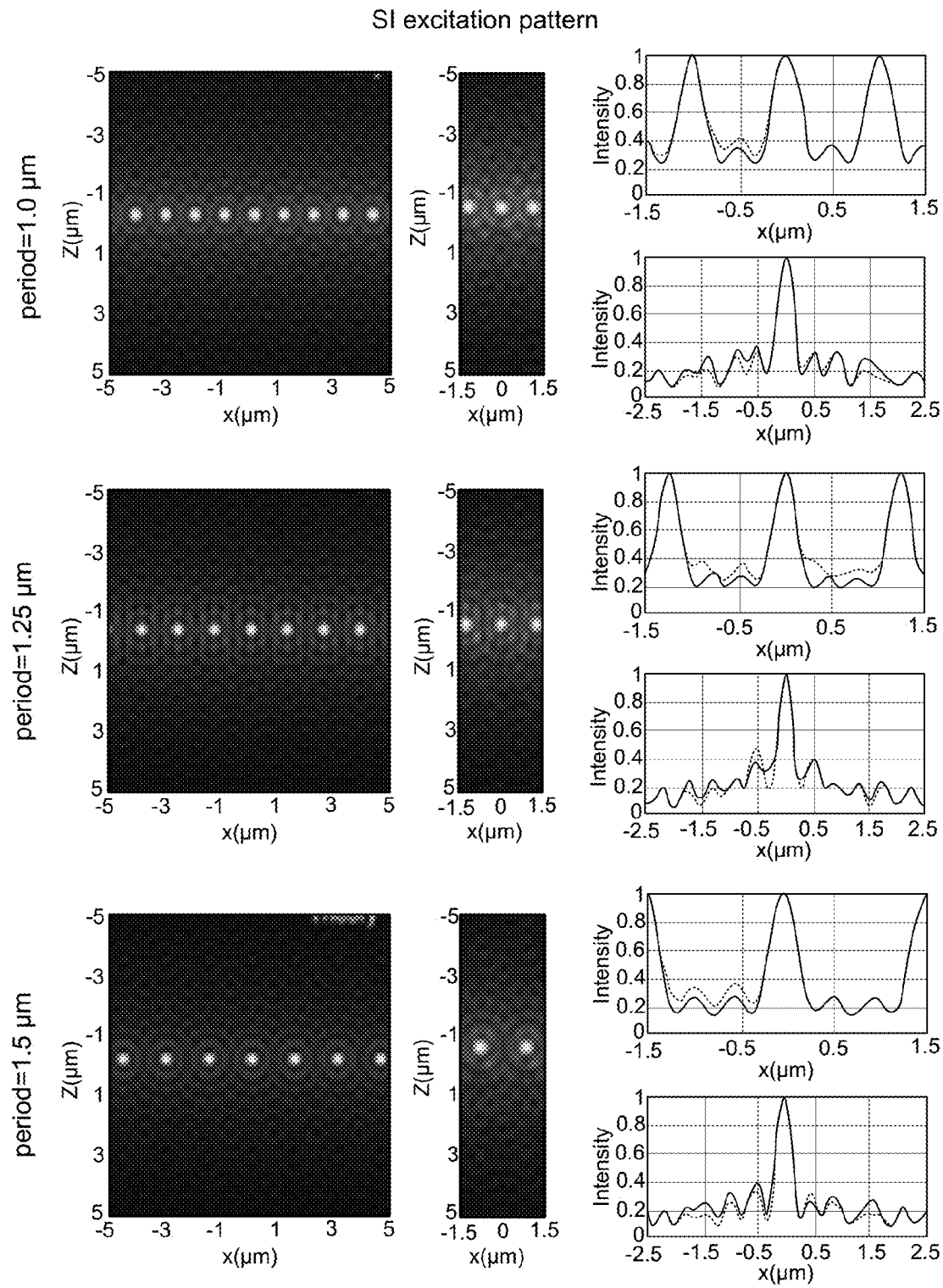
FIG. 19A shows theoretical and experimental higher-order harmonic structured illumination patterns that can be created with Bessel-like beams having a maximum numerical aperture of 0.60 and the minimum vertical aperture of 0.58, which are created with 488 nm light.

An alternative that can better retain both signal and axial resolution is to create a multi-harmonic excitation pattern by stepping the beam at a fundamental period larger than $\lambda/NA_{Bessel}^{max}$, as seen in FIG. 19A, which shows theoretical and experimental higher-order harmonic structured illumination patterns that can be created with Bessel-like beams having a maximum numerical aperture of 0.60 and the minimum vertical aperture of 0.58, which are created with 488 nm light. To create a single SI image with a pattern having H harmonics, Eq. (1) is again used, except with N≥H+2 images, each with the pattern phase shifted by 2π/N relative to its neighbors.

Figure 19B:
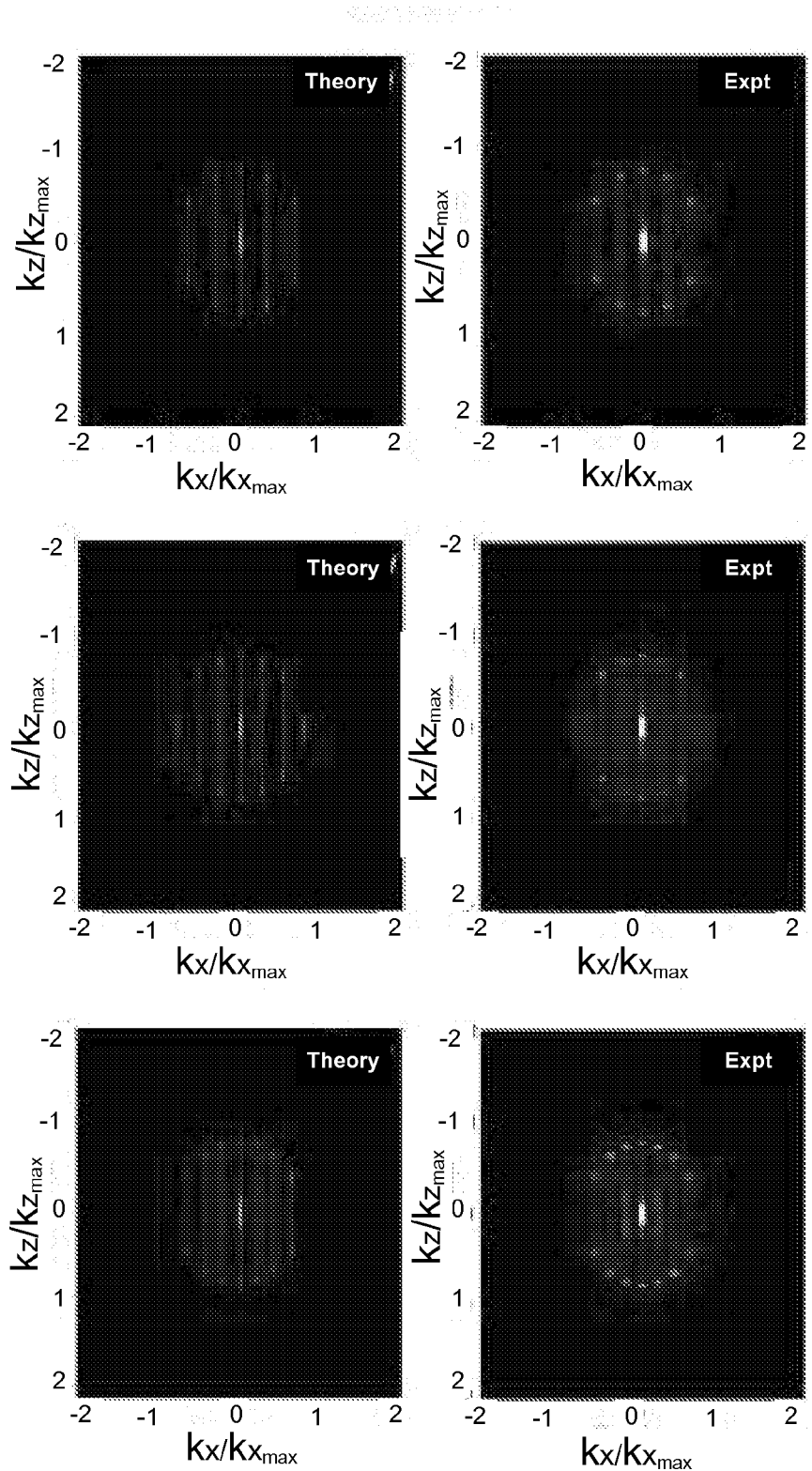
FIG. 19B shows theoretical and experimental modulation transfer functions (MTFs) in reciprocal space, which correspond to the point spread functions shown in the two left-most columns of FIG. 19A.

FIG. 19B shows theoretical and experimental modulation transfer functions (MTFs) in reciprocal space, which correspond to the point spread functions shown in the two left-most columns of FIG. 19A. As shown in FIG. 19B, with increasing H, more side bands are generated in the MTF that contain a greater combined fraction of the total spectral energy relative to the $k_x=0$ band, thus yielding higher signal-to-noise (SNR) images. Due to the greater weighting of these sidebands to lower $k_z$, axial resolution (i.e., along the axis of the detection objective 1315) of this multi-harmonic SI mode is slightly less (0.29 µm FWHM for N=9 phases) than in the single harmonic case, yet images of fixed and living cells still exhibit isotropic 3D resolution, albeit at the cost of more data frames required per image plane, and thus lower speed.

In addition to this speed penalty, both single-harmonic and multi-harmonic SI modes still generate some excitation beyond the focal plane, and are thus not optimally efficient in their use of the photon budget. Both these issues can be addressed using two-photon excitation (TPE), which suppresses the Bessel side lobes sufficiently such that a thin light sheet can be obtained even with a continuously swept beam. As a result, high axial resolution and minimal out-of-focus excitation is achieved in fixed and living cells with only a single image per plane. Some additional improvement is also possible with TPE-SI, but the faster TPE sheet mode can be preferred for live cell imaging. The benefits of TPE are not limited to structured illumination excitation of the specimen, but are beneficial during other modes of Bessel-like beam plane illumination of the specimen to reduce out of focus excitation and photo damage by the illumination beam. Other forms of non-linear excitation with a Bessel like beam, such as coherent anti-Stokes Raman scattering (CARS), can also reap similar benefits.

Thus, the improved confinement of the excitation light to the vicinity of the focal plane of the detection objective made possible by Bessel beam plane illumination leads to improved resolution in the axial direction (i.e., in the direction along the axis of the detection objective) and reduced photobleaching and phototoxicity, thereby enabling extended observations of living cells with isotropic resolution at high volumetric frame rates. For example, extended imaging of the endoplasmic reticulum in a live human osteosarcoma cell (U2OS cell line) in the linear multi-harmonic SI mode was performed. Despite the fact that over three-hundred image slices were required to construct each 3D image stack, the dynamics of the ER could be followed over 45 minutes at a rate of 1 stack/min with axial resolution of ~0.3 µm.

Even longer duration observations were found to be possible in the TPE sheet mode. For example, portions of three consecutive image stacks from a series of one hundred such stacks showed the evolution of numerous filopodia on the apical surface of a HeLa cell transfected with mEmerald/Lifeact. Significantly, the imaging speeds achievable in this mode (51.4 image planes/sec, 6 sec stack interval) enable even complex, rapid 3D cellular processes to be visualized with sufficient time resolution. This is further underscored by consecutive images of the retrograde flow of membrane ruffles formed at the leading edge of a transformed African green monkey kidney cell (COS-7 cell line, transfected with mEmerald/c-src). Such ruffles can surround and engulf extracellular fluid to create large intracellular vacuoles, a process known as macropinocytosis, which was directly demonstrated using the techniques described herein. The visualization of these processes in four dimensional spatiotemporal detail (0.12×0.12×0.15 μm×12.3 sec stack interval) across 15 minutes cannot currently be achieved with other fluorescence microscopy techniques.

For sufficiently bright samples, the pixel rate of EMCCD cameras becomes a limiting factor. To achieve even higher imaging speeds in such cases, a scientific CMOS camera (125 MHz, Hamamatsu Orca Flash 2.8) can be used. To exploit the full speed of the camera, a third galvanometer-type mirror that can be tilted can be placed at a plane conjugate to the rear pupil of the detection objective and used to tile several image planes across the width of the detector, which were then are read out in parallel.

Figure 20:
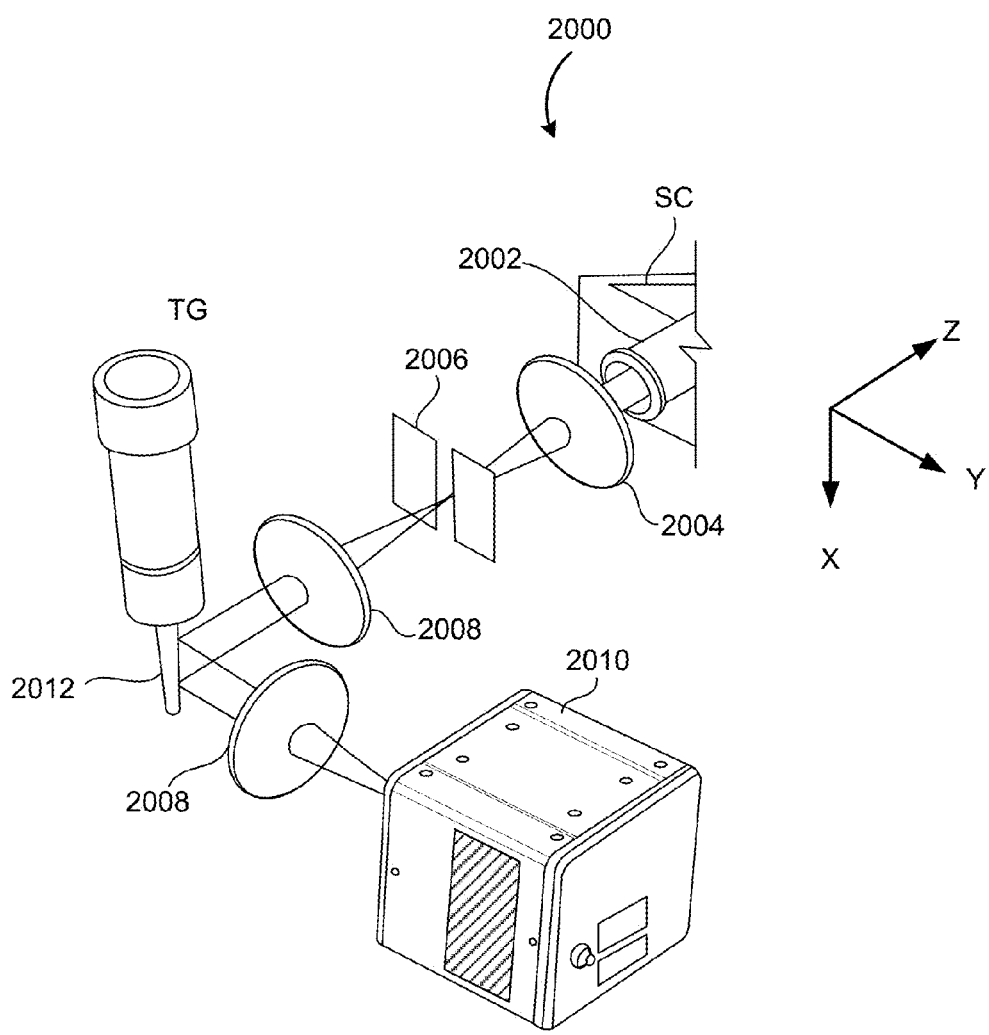
FIG. 20 shows a system with a galvanometer-type mirror placed at a plane that is conjugate to the detection objective between the detection objective and the detector.

FIG. 20 shows a system 2000 with a mirror placed at a plane that is conjugate to the detection objective between the detection objective and the detector. In the system 2000, detection light collected by detection objective 2002 can be focused by a tube lens 2004 to form an image at the plane of an adjustable slit 2006. The image cropped by the adjustable slit 2006 is reimaged by relay lenses 2008 onto a high-speed detection camera 2010. A galvanometer-type mirror 2012 is placed the plane between the relay lenses 2008 that is conjugate to the back focal plane of the detection objective 2012. By changing the angle of galvanometer-type mirror, multiple images can be exposed across the surface of the detection camera 2010 and then read out in parallel to exploit the full speed of the detection camera 2010.

With this configuration, the 3D dynamics of chromatid separation in early anaphase could be studied in the TPE sheet mode at rates of 1 volume/sec. Significantly, even at these imaging rates, the excitation did not arrest mitosis. Moreover, the intracellular trafficking of vesicles in a COS-7 cell could be observed over the course of 7000 frames acquired in a single plane at 191 frames/sec.

Three-dimensional live cell imaging can be performed with Bessel-like beans with the use of fluorescent proteins to highlight selected portions of a specimen. A key aspect of fluorescent proteins (FPs) is that their spectral diversity permits investigation of the dynamic interactions between multiple proteins in the same living cell. For example, after transfection with mEmerald/MAP4 and tdTomato/H2B, microtubules in a pair of U2OS cells surrounding their respective nuclei, were imaged in the linear, nine-phase multi-harmonic SI mode. Nevertheless, although many vectors are available for linear imaging, the need for N frames of different phase per image plane can limits the use of SI with Bessel-like beams to processes which evolve on a scale that matches the time required to collect frames at the desired spatial resolution. Of course, this limitation does not apply for fixed cells, where the linear SI mode is preferred, due to its superior axial resolution and the availability of a wider array of fluorescent dyes as well as FPs for protein specific labeling. For example, three-color isotropic 3D imaging of the actin cytoskeleton of an LLC-PK1 cell stained with Alexa Fluor 568 phalloidin, the nuclear envelope tagged with mEmerald/lamin B1, and nuclear histones tagged with mNeptune/H2B was performed.

For imaging multiple proteins exhibiting faster dynamics, the TPE sheet mode can be used. However, this presents its own challenges: orange/red FPs such as tdTomato and mCherry do not have the same TPE brightness and photostability of green FPs such as EGFP or mEmerald and require a second expensive ultrafast light source, since the time required to retune and realign a single source is prohibitive for live cell imaging. Fortunately, the 3D isotropic resolution of the Bessel TPE sheet mode permits multiple proteins tagged with the same FP to be imaged simultaneously, as long as they are known a priori to be spatially segregated. For example, the fragmentation of the Golgi apparatus between metaphase (t=0 min) and anaphase (t=10 min) was observed, as identified by chromosome morphology (green), and the re-constitution of the Golgi (t=20 min) around the daughter nuclei in telophase (t=40 min).

As described herein, Bessel beam plane illumination microscopy techniques offer 3D isotropic resolution down to ~0.3 μm, imaging speeds of nearly 200 planes/sec, and the ability, in TPE mode, to acquire hundreds of 3D data volumes from single living cells encompassing tens of thousands of image frames. Nevertheless, additional improvements are possible. First, substantially greater light collection making still better use of the photon budget is obtained by using a detection objective with a numerical aperture of 1.0 or greater. Although mechanical constraints would thereby force the use of an excitation objective with a numerical aperture of less than 0.8 thus lead to a somewhat anisotropic point spread function (PSF), the volumetric resolution would remain similar, since the slight loss of axial resolution would be offset by the corresponding transverse gain.

As noted above, SI using the algorithm in Eq. (1) is also photon inefficient, as it achieves high axial resolution by removing substantial spectral energy that resides in the $k_x=0$ band of the MTF. An alternative would be to use the algorithms of 3D superresolution SI, which assign the sample spatial frequencies down-modulated by all bands of the excitation to their appropriate positions in an expanded frequency space. By doing so, shorter exposure times and fewer phases are needed to record images of acceptable SNR, making linear Bessel SI a more viable option for high speed multicolor imaging. In addition, resolution can be extended to the sum of the excitation and detection MTF supports in each direction—an argument in favor of using three mutually orthogonal objectives. Indeed, the marriage of Bessel beam plane illumination and 3D superresolution SI permits the latter to be applied to thicker, more densely fluorescent specimens than the conventional widefield approach, while more efficiently using the photon budget.

Superresolution SI can be performed by extending the structured illumination techniques described above with respect to FIG. 18 and FIG. 19. By illuminating the sample with a structured illumination pattern, normally inaccessible high-resolution information in an image of a sample can be made accessible in the form of Moiré fringes. A series of such images can be processed to extract this high-frequency information and to generate reconstruction of the image with improved resolution compared to the diffraction limited resolution.

Figures 21A, 21B, 21C, 21D, 21E:
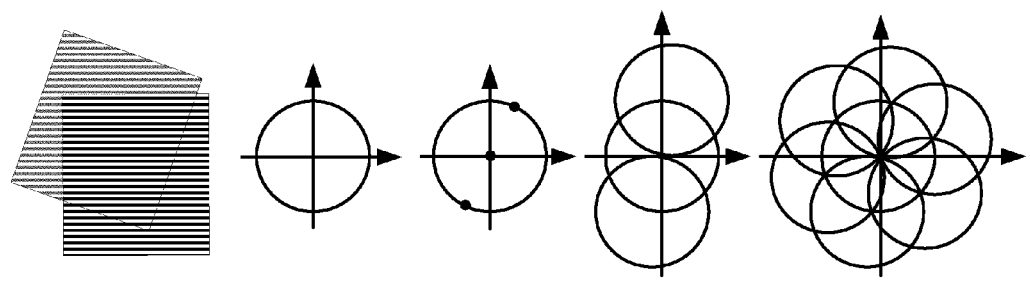
FIG. 21A shows two overlapping structured patterns.
FIG. 21B shows a reciprocal space representation of one of the patterns of FIG. 21A.
FIG. 21C shows shows a reciprocal space representation of the other pattern of FIG. 21A.
FIG. 21D shows an observable region of a reciprocal space representation of specimen structure shifted from the reciprocal space origin.
FIG. 21E shows observable regions of reciprocal space representations of specimen structure shifted from the reciprocal space origin, where the different representations correspond to different orientations and/or phases of a structured pattern overlayed with the specimen structure.

The concept of super resolution SI exploits the fact that when two patterns are superimposed multiplicatively a beat pattern will appear in the product of the two images, as seen in FIG. 21A. In the case of Bessel-like beam plane illumination microscopy, one of the patterns can be the unknown sample structure, for example, the unknown spatial distribution of regions of the sample that receive illumination light and that emit signal light—and the other pattern can be the purposely structured pattern of excitation light that is written in the form of parallel Bessel-like beams. Because the amount of signal light emitted from a point in the sample is proportional to the product of the local excitation light intensity and the relevant structure of the sample, the observed signal light image that is detected by the detector will show the beat pattern of the overlap of the two underlying patterns. Because the beat pattern can be coarser than those of the underlying patterns, and because the illumination pattern of the Bessel-like beams is known, the information in the beat pattern can be used to determine the normally unresolvable high-resolution information about the sample.

The patterns shown in FIG. 21A can be Fourier transformed into reciprocal space. For example, the Fourier transform of the structure of a sample that is imaged by an a convention widefield optical system is constrained by the Abbe resolution limit would be represented by a circle having a radius of $2NA/\lambda$, as shown in FIG. 21B, where the low resolution components of the sample are close to the origin, and the high-resolution components are close to the edge of the circle. The Fourier transform of a 2D illumination pattern that consists of a sinusoidal variation in the illumination light in one dimension and having a period equal to the diffraction limit of the optical system has three non-zero points that lie on the circle shown in FIG. 21C. One point resides at the origin and the other two points are offset from the origin in a direction defined by the orientation of the illumination pattern by distances proportional to the inverse of the spatial period of the pattern. When the specimen is illuminated by structured illumination, the resulting beat pattern between the specimen structure and the illumination structure represents information that has changed position in reciprocal space, such that the observable region of the sample in physical space then contains new high-frequency information represented by the two regions and FIG. 21D that are offset from the origin. For example, the regions of the offset circles in FIG. 21D that fall outside the central circle represent new information that is not accessible with a conventional eidefield technique. When a sequence of such images is obtained using structured excitation radiation that is oriented in different directions multiple circles that lie outside the central circle are produced, as shown in FIG. 21E. From this plurality of images, information can be recovered from an area that can be twice the size of the normally observable region, to increase the lateral resolution by up to a factor of two is compared with widefield techniques.

In an implementation using a structured illumination pattern of Bessel-like beams, as explained above with respect to FIG. 18 and FIG. 19, N images can be recorded with the spatial phase of the illumination pattern between each image shifted by $\Lambda/N$ in the X direction, where $\Lambda$ is the spatial period of the pattern and N is the number of harmonics in reciprocal space. Then, a Fourier transform can be performed on each of the N images, and the reciprocal space images can moved to their true positions in reciprocal space, combined through a weighted-average in reciprocal space, and then the weight-averaged reciprocal space image can be re-transformed to real space to provide an image of the sample. In this manner, a superresolution image of the sample can be obtained, where the resolution of the image in both the X and Z directions can be enhanced over the Abbe diffraction limited resolution. The resolution enhancement in the X direction can be up to a factor of two when the NA of the structured excitation and the NA of the detection are the same. However, the excitation lens NA is usually lower than that of the detection lens, so the extension beyond the Abbe limit is usually less than a factor of two but more than a factor of one. In the Z direction, the resolution improvement can be better than a factor of two, since the transverse Z resolution of the excitation can exceed the transverse Z resolution of the detection.

In another implementation, more than one excitation objective can be used to provide a structured illumination pattern to the sample, where the different excitation objectives can be oriented in different directions, so that super resolution of the sample can be obtained in the directions transverse to the Bessel-like beams of each of the orientation patterns. For example, a first excitation objective can be oriented with its axis along the Y direction (as described above) and can illuminate the sample with an illumination pattern of Bessel-like beams that provides a superresolution image of the sample in the X and Z directions, and a second excitation objective can be oriented with its axis along the X direction and can illuminate the sample with an illumination pattern of Bessel-like beams that provides a superresolution image of the sample in the Y and Z directions. The superresolution information that can be derived from illumination patterns from the different excitation objectives can be combined to yield extended resolution in all three directions.

In another implementation, highly inclined, objective-coupled sheet illumination has been used to image single molecules in thicker regions of the cell where autofluorescence and out-of-focus excitation would be otherwise prohibitive under widefield illumination. With the thinner light sheets possible with Bessel beam plane illumination, only in-focus molecules would be excited, while out-of-focus ones would not be prematurely bleached. As such, it would be well suited to live cell 3D particle tracking and fixed cell photoactivated localization microscopy.

At the other extreme, the TPE sheet mode may be equally well suited to the imaging of large, multicellular specimens, since it combines the self-reconstructing property of Bessel beams with the improved depth penetration in scattering media characteristic of TPE. In addition to large scale 3D anatomical mapping with isotropic resolution, at high frame rates it might be fruitfully applied to the in vivo imaging of activity in populations of neurons. When the sample is excited with two-photon excitation radiation, additional spatial frequencies are introduced to images generated from detected light that is emitted from the sample, and the additional spatial frequencies can provide additional information that may be exploited to enhance the resolution of a final image of the sample generated through the super resolution structured illumination techniques described herein. The infrared excitation light used in TPE can penetrate tissue with reduced scattering and aberration, and the out-of-focus emission from the side lobes of the excitation beam can be suppressed. Similarly, the suppression of the side lobes confines the TPE excitation radiation more closely to the Z=0 plane permitting substantial axial resolution improvement when applied to SR-SIM.

Figure 22A:
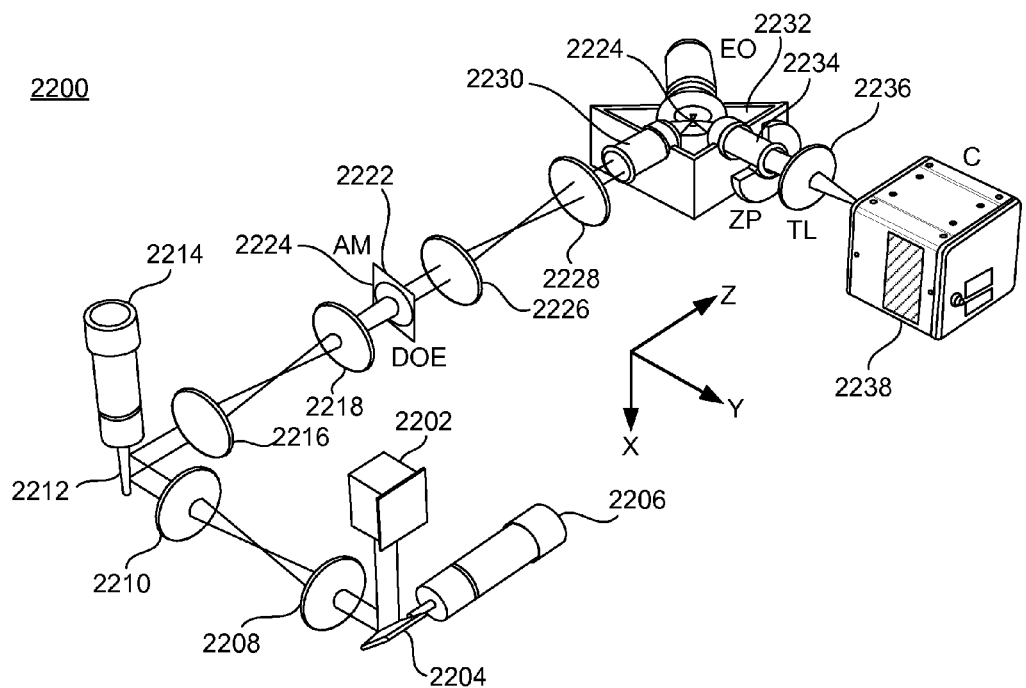
FIG. 22A is a schematic diagram of a system for producing an array of Bessel-like beams in a sample.

FIG. 22A is a schematic diagram of a system 2200 for generating and providing an array of Bessel-like excitation beams to a sample, similar to the comb of beams show in FIG. 17B, and for imaging the light emitted from the sample due to interaction between the Bessel-like beams and the sample.

As shown in FIG. 22A, a light source 2202 (e.g., a laser) can produce coherent, collimated light such as a beam having a Gaussian intensity profile, which can be reflected from first galvanometer-type mirror 2204. The mirror 2204 can be controlled by a fast motor 2206 that is used to rotate the mirror and steer the beam in the X direction. After the beam is reflected from the mirror 2204, it is imaged by relay lens pair 2208 and 2210 onto a second galvanometer-type mirror 2212 positioned at a point optically conjugate to the first galvanometer-type mirror 2204. The mirror 2212 can be controlled by a fast motor 2214 that is used to rotate the mirror and steer the beam in the Z direction.

A second lens pair 2216 and 2218 then can relay the light to a diffractive optical element (DOE) 2224 located just in front of an annular apodization mask (AM) 2222 that is conjugate with the second galvanometer-type mirror 2212. The DOE 2220 can be, for example, a holographic diffractive optical element, that creates, in the far field from the DOE, a fan of Gaussian beams. In some implementations, the DOE can create a fan of seven beams. The apodization mask 2222, located just after the DOE 2220, can be used in combination with the DOE to generate an array of Bessel-like beams in the sample 2240.

The annular light beams transmitted through the AM 2222 are relayed by a third lens pair 2226 and 2228 onto a conjugate plane coincident with the back focal plane of excitation objective 2230. Finally, the annular light beams are focused by the objective 2230 to form a fan of Bessel-like beam s that are used to provide excitation light to the sample 2240. The sample 2240 can be placed in an enclosed sample chamber 2232 that can be filled with aqueous media and that can be temperature controlled. Signal light emitted from the sample can be collimated by a detection objective 2234 and focused by a tube lens 2236 onto a position sensitive detector 2238. The signal light emitted from the sample can be generated through a non-linear signal generation process. For example, in one implementation, the signal light may be generated through a two-photon process, such that the signal light has a wavelength that is one half the wavelength of the excitation light of the Bessel-like beams.

Figure 22B:
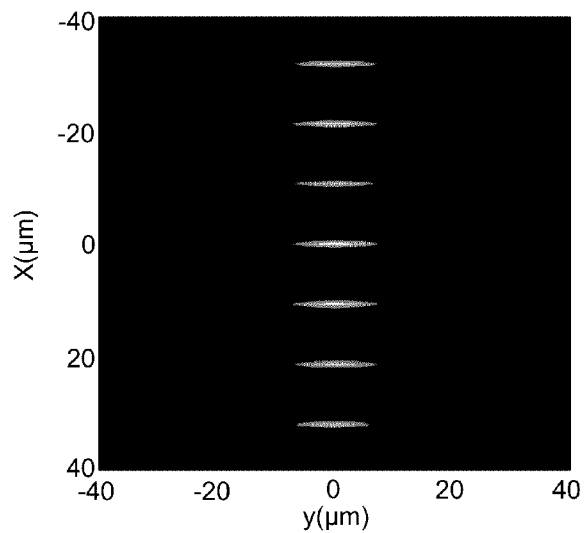
FIG. 22B is a view of an array of Bessel-like beams.
Figure 22C:
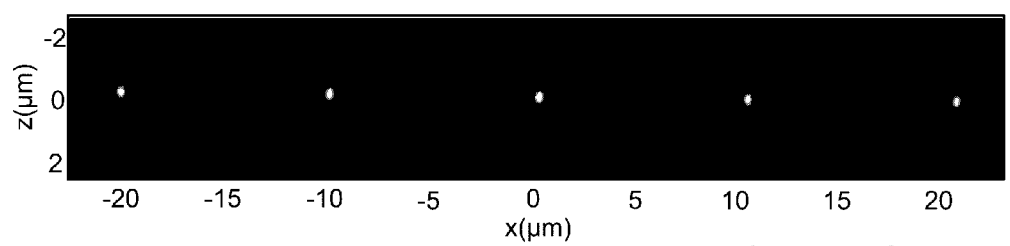
FIG. 22C is another view of the array of Bessel-like beams shown in FIG. 22B.
Figure 22D:
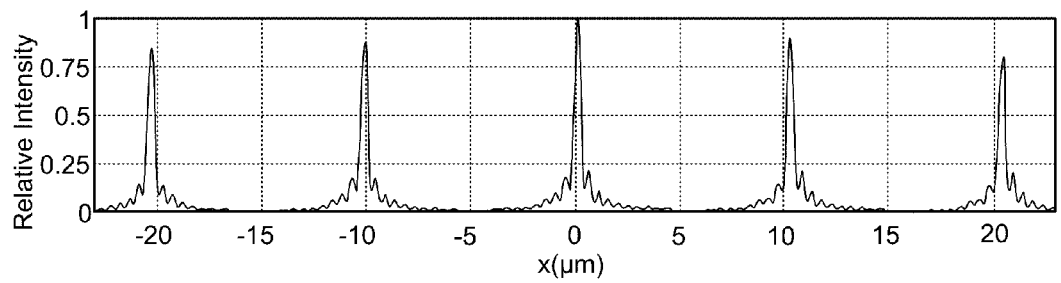
FIG. 22D is a plot of the relative intensity of light produced by the array of Bessel-like beams shown in FIG. 22B and FIG. 22C along a line in which the beams lie.

FIGS. 22B and 22C, are example diagrams showing an array of substantially parallel Bessel-like beams produced by the system 2200. FIG. 22B shows the array of beams in the X-Y plane, and FIG. 22C shows the array of beams in the X-Z plane, although FIG. 22C shows only five of the seven Bessel-like beams. In one implementation, a diffractive optical element that produces seven beams in combination with the other beam-forming optics of system 2200, including the apodization mask 2222 and the excitation objective 2230, can create the array of seven Bessel-like beams shown in FIGS. 22B and 22C. As shown in FIGS. 22B and 22C, the beams, for particular parameters and configurations of the beam-forming optics of system 2200, including the dimensions of the apodization mask, the numerical aperture of the excitation objective 2230, etc. the Bessel-like beams that are produced in the sample can extend over a length of approximately 10 µm, and can have central lobes with diameters on the order of 1 µm. FIG. 22D is a schematic figure showing a relative intensity plots of five of the seven Bessel-like beams along the X-axis at the Y=0, Z=0 plane. As shown in FIG. 22D, in this implementation, the intensity profiles of neighboring Bessel-like beams do not substantially overlap. Nevertheless, use of the array of N non-overlapping beams spreads the excitation energy over N beams instead of concentrating the energy in just one beam, and, therefore, the sample is subject to less damage. In addition an array having a plurality of beams can be stepped across the sample to create an incoherent structured illumination pattern over a given field of view faster than one beam can be stepped.

The rotational axis of galvanometer mirror 2204 can be positioned such that tilting this galvanometer-type mirror 2204 causes the array of Bessel-like beams to sweep across the focal plane of detection objective 2234 (i.e., in the X direction), whose axis is orthogonal to (or whose axis has an orthogonal component to) the axis of the excitation objective 2230. Thus, through control of the galvanometer-type mirror 2204, the array of Bessel-like beams can be swept in the X direction to produce a thin sheet of light in a plane.

The signal light emitted from the sample 2240 can be directed by detection optics, including the detection objective 2234, to a detector 2238. The galvanometers-type mirrors 2204, 2212 can provide sweep rates of up to about 2 kHz, and with resonant galvanometer-type mirrors (e.g., Electro-Optical Products Corp, model SC-30) sweep rates can exceed 30 kHz. Extremely high frame rate imaging is then possible when the system is used in conjunction with a high frame rate detection camera.

The rotational axis of the galvanometer mirror 2212 can be positioned such that tilting of this mirror causes the array of Bessel-like beams to translate along the Z axis of detection objective 2234. By doing so, different planes within a specimen can be accessed by the Bessel beam, and a three dimensional (3D) image of the specimen can be constructed, with much higher axial resolution than in conventional light sheet microscopy, due to the much narrower sheet of excitation afforded by array of Bessel-like excitation. In order to image each plane in focus, either detection objective 2234 must be moved synchronously with the motion of the array of Bessel-like beams imparted by the tilt of galvanometer-type mirror 2212 (such as with a piezoelectric transducer), or else the effective plane of focus of the detection objective 2234 must be altered, such as by using a second objective to create a perfect image of the sample. In another implementation, the excitation plane and the detection plane can remain fixed and the sample can be moved through the planes, for example, by using a piezoelectric transducer to move the sample through the beam to cover different z planes. For relatively flat samples, this allows the use of a shorter Bessel-like beams in the Y-direction with less energy in the side-lobes.

The plurality of Bessel-like beams can lie in a plane within the sample and can be equally spaced from neighboring beams, such that the plurality of beams form a pattern in the plane having a spatial period, $\Lambda$. The array of beams can be scanned in a direction perpendicular to their propagation direction (e.g., in the X direction). In some implementations, the array of beams can be scanned in a series of discrete steps. For example, the array of beams can be scanned from its original position in N-1 discrete steps, where N is an integer, and the steps can have a length of $(N-1)\cdot\Lambda/N$. Images of the sample can be recorded based on light emitted from the sample when the array of Bessel-like beams is in each of the N different positions within the sample (i.e., in the original position and in the N-1 scanned positions). Then, a final image of the sample can be generated through a linear combination of the N individual images of the sample. For example, the linear combination of the different images can be created according to $$I_{final} = \left| \sum_{n=1}^{N} I_n \exp(2\pi i n / N) \right|.$$

where $I_{final}$ is an intensity of the final image at a particular position within the sample, n is an index variable corresponding to the different individual images that are generated, and In is an intensity of the particular position within the sample in the nth individual image.

In some implementations, the array of the Bessel-like beams can be spatially dithered (i.e., rapidly changed in a periodic manner) at a dither frequency back and forth in the plane of the array of beams. For example, the galvanometer-type mirror 2204 can be tilted back and forth to dither the spatial position of the array of Bessel-like beams. The array of Bessel-like beams can be spatially dithered over a distance greater than or approximately equal to the spatial period, Λ, of the pattern of the array of Bessel-like beams. While dithering the array, the Bessel-like beams can be moved in the plane at the array (e.g., along the X axis) at a substantially constant rate, so that the time-averaged intensity of light in the plane of the array is substantially constant. When the inverse of the dither frequency is greater than the integration time of the detector 2238, the excitation light provided by the array of Bessel-like beams in the sample can appear to the detector as a uniform sheet of excitation light.

The system in FIG. 22A is typically quite wasteful of the energy in light beam 2201, because most of this light is blocked by apodization mask 2208. If greater efficiency is desired, a diffractive optical element such as a binary phase mask or spatial light modulator and a collimating lens can be used to create an approximately annular light beam prior to more exact definition of this beam and removal of higher diffractive orders by the apodization mask 2208.

The different, substantially parallel Bessel-like beams that are produced from the light of the light source and the beam-forming optics shown in FIG. 22A, can be created from a single source of coherent light, and the beam-forming optics can be held in stable positions, such that fixed phase relationships exist between the different substantially parallel Bessel-like beams in the sample. In some implementations, for example, in the implementation shown in FIGS. 22B, 22C, and 22D, the different Bessel-like beams can be spaced apart from the other with the spacing that is great enough so that the light from neighboring Bessel beams does not interact substantially.

Another technique to reduce the influence of the side lobes and to improve the Z-axis resolution of images obtained of a sample is to employ structured illumination using a coherent array of Bessel-like beams that are provided simultaneously to the sample, such that interference between the beams of the coherent array improves the Z-axis confinement of the plane of structured illumination that is used to provide excitation radiation to the sample. One way to imagine the creation of such a structured illumination plane is to think of the plane being created by different beams that are spaced apart from their neighboring beams by distances small enough for neighboring beams to overlap and interfere with each other. For example, in some implementations neighboring Bessel-like beams can be spaced by distances that are less than or comparable to a diameter of a first side lobe of the Bessel-like beams. Interference between the beams then creates a structured light sheet of high modulation depth within the desired Z=0 plane, improving the performance in optically sectioned or superresolution structured plane illumination. In addition, destructive interference between the side lobes outside the Z=0 plane reduces the out-of focus excitation from the side lobes, reducing phototoxicity and decreasing the thickness of the light sheet created by sweeping or dithering the structured light sheet.

Figure 23:
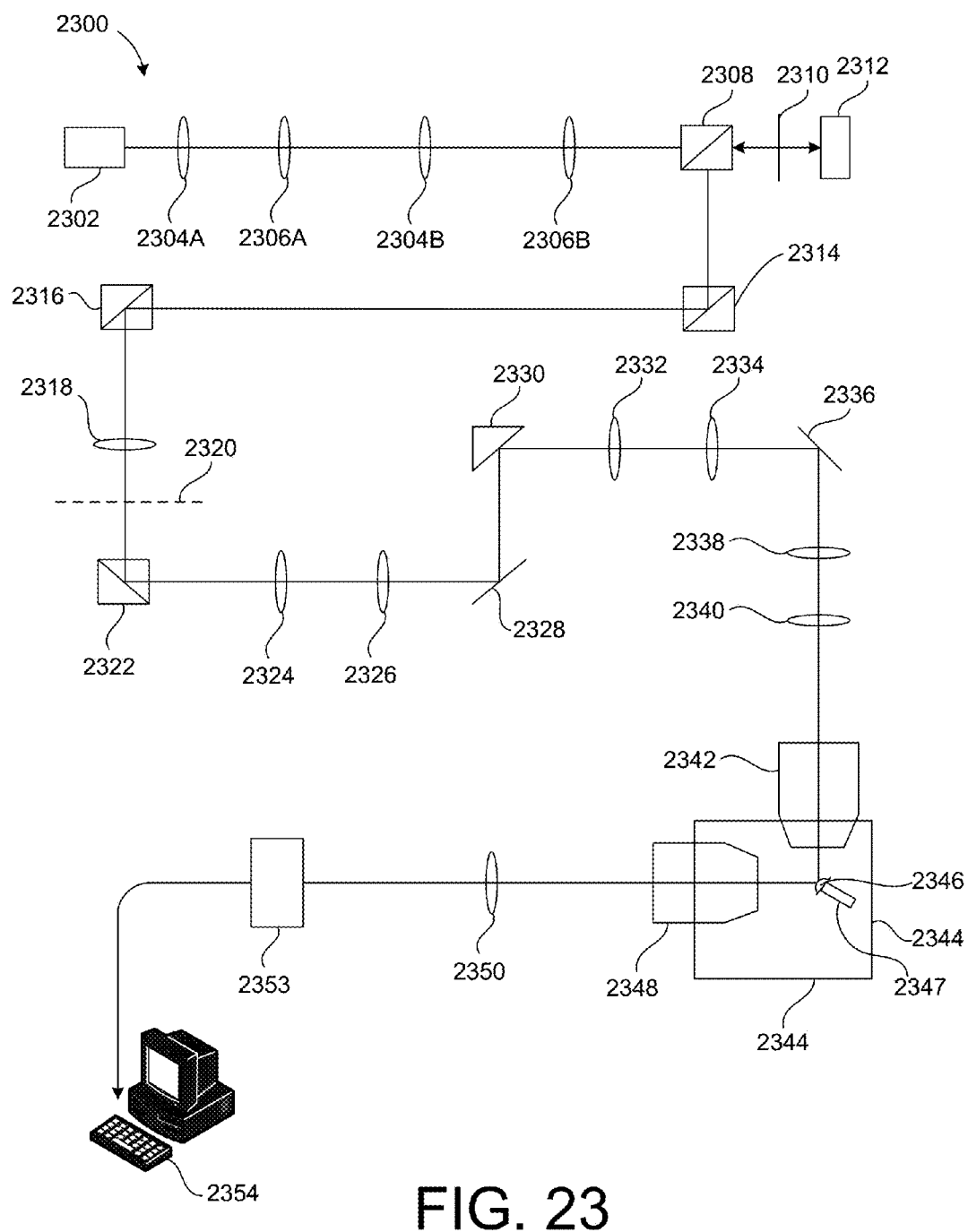
FIG. 23 is a schematic diagram of another system for producing an array of Bessel-like beams in a sample.

FIG. 23 is a schematic diagram of another system 2300 for producing an array of Bessel-like beams in a sample. As shown in FIG. 23, the light beam from the light source 2302 can be spatially expanded in the X direction by a pair of cylindrical lenses 2304A, 2304B and can be spatially reduced in the Z direction by a pair of cylindrical lenses 2306A, 2306B to produce a beam having an intensity profile that is wide in the X direction and narrow in the Z direction.

The beam can pass through a beam splitter 2308 half-wave plate 2310 and then impinge on a wavefront modulating element (WME) 2312 that independently modulates individual portions of the entire wavefront. The insertion of the half-wave plate 2310 in the beam path can make the WME 2312 operate as a phase modulator of portions of the beam that strike the WME. In some implementations, the WME can include a liquid-crystal phase-only spatial light modulator. In another implementation, the WME can include a ferroelectric binary spatial light modulator. In other implementations, the WME 2312 can include a deformable mirror (e.g., a piston-tip-tilt mirror) or an array of micromirrors. By controlling the WME 2312 (e.g., by control of the individual pixels of a spatial light modulator or individual mirrors within an array of micrometers or control of individual elements of a piston-tip-tilt mirror), the wavefront of the light reflected from the WME 2312, and consequently the wavefront(s) of downstream beam(s) (e.g., beams in the sample 2346), can be controlled. For example, the WME 2312 can be programmed to modulate the wavefront of the incoming light beam such that the outgoing light beam from the WME subsequently defines an array of coherent Bessel-like beams that overlap and interfere with each other to create a plane of structured illumination in the sample 2346. The WME 2312 can be optically conjugated to the sample 2346, so that modulations introduced by the WME can be propagated to the sample.

The WME 232 can be used to control the relative phases of individual beamlets (or portions of the incoming wavefront) that are reflected from the WME. For example, the WME 2312 can be used to control the relative phases of individual portions of the wavefront that strike the WME 2312 and that then propagate into the sample 2346. In some implementations, this relative phase control of individual portions of the reflected wave front can result in control of relative phases of individual Bessel-like beams in array of beams in the sample 2346.

In some implementations, the WME 2312 can include a spatial light modulator, and in some implementations the spatial light modulator can be a binary spatial light modulator, in which each pixel of the spatial light modulator can have one of two different states that affect the light modulated by the pixel. In some implementations, the WME 2312 can be used to scan the array of Bessel-like beams within the sample—either within the plane of the array or perpendicular to the plane (e.g. in the Z axis direction).

An advantage of using a reflective spatial light modulator (SLM) as the WME is that, with a high number of pixels (e.g., 1024×1280 pixels), it can be readily divided into many subregions, and in part because the subregions are truly independent, and not mechanically coupled, as in a deformable mirror.

After modulation by the WME 2312, the light reflected from the WME can be reflected by the beam splitter 2308 and reflected by mirrors 2314, 2316. Then, the light can be imaged by a lens 2318 onto an apodization mask 2320 that is conjugate to the rear pupil of the excitation objective 2342. After the apodization mask 2320, the light can be reflected off of a mirror 2322, transmitted through relay lenses 2324, 2326, reflected off galvanometer mirror 2328, mirror 2330, transmitted through relay lenses 2332, 2334, reflected off galvanometer mirror 2336, and transmitted through relay lenses 2338, 2340 to the rear pupil plane of excitation objective 2342. Then, the light can be focused by excitation objective 2342 onto the sample 2346 that is housed in chamber 2344.

Mirror 2328 can operate as a galvanometer-type mirror to translate the structured plane illumination in the X direction within the sample, and the mirror 2328 can be conjugated to the apodization mask 2320 by relay lenses 2324, 2326. Mirror 2336 can operate as a galvanometer-type mirror to translate the structured plane illumination in the Z direction within the sample, and the mirror 2336 can be conjugated to mirror 2328 by relay lenses 2332, 2334. The rear pupil plane of excitation objective 2342 can be conjugated to mirror 2336 by relay lenses 2338 and 2340. The combination of lenses 2318, 2324, 2326, 2332, 2334, 2338, and 2340 as well as excitation objective 2342 then serve to conjugate WME 2312 to an excitation plane within the sample 2346. The sample 2346 can be supported on a translation stage 2347 that can be used to translate the sample in space. In some implementations, the translation stage 2347 can translate the sample 2346 with respect to a beam of radiation that is provided to the sample, while the position of the beam remains fixed.

Light emitted from the sample 2346 due to the interaction of the excitation light with the sample can be collected by the detection objective 2348 and then focused by lens 2350 onto a detector 2352. Information collected by the detector 2352 can be sent to a computing device 2354, which may include one or more processors and one or more memories. The computing device may process the information from the detector 2352 to create images of the sample 2346 based on the information provided by the detector 2352.

The WME 2312 can control the wavefront of the light leaving the WME, such that the plurality of Bessel-like beams is created in the sample 2346. Furthermore, the WME 2312 can control the relative phases of the individual Bessel-like beams in the sample. The relative phases of the individual Bessel-like beams can be controlled such that neighboring Bessel-like beams interfere destructively with each other at positions that are out of the plane of the array of Bessel-like beams. For example, the destructive interference can occur within the Z≠0 plane when the array of Bessel-like beams is in the Z=0 plane. For example, the first side lobes of neighboring Bessel-like beams can destructively interfere where they intersect with each other at locations that are not in the plane of the array. For example, the intersection point can occur at a position that is closer to the plane of the array than a diameter of the first side lobe of the Bessel-like beams. Techniques for using a spatial light modulator WME to create structured light sheets within the sample are described in more detail below.

Figure 24:
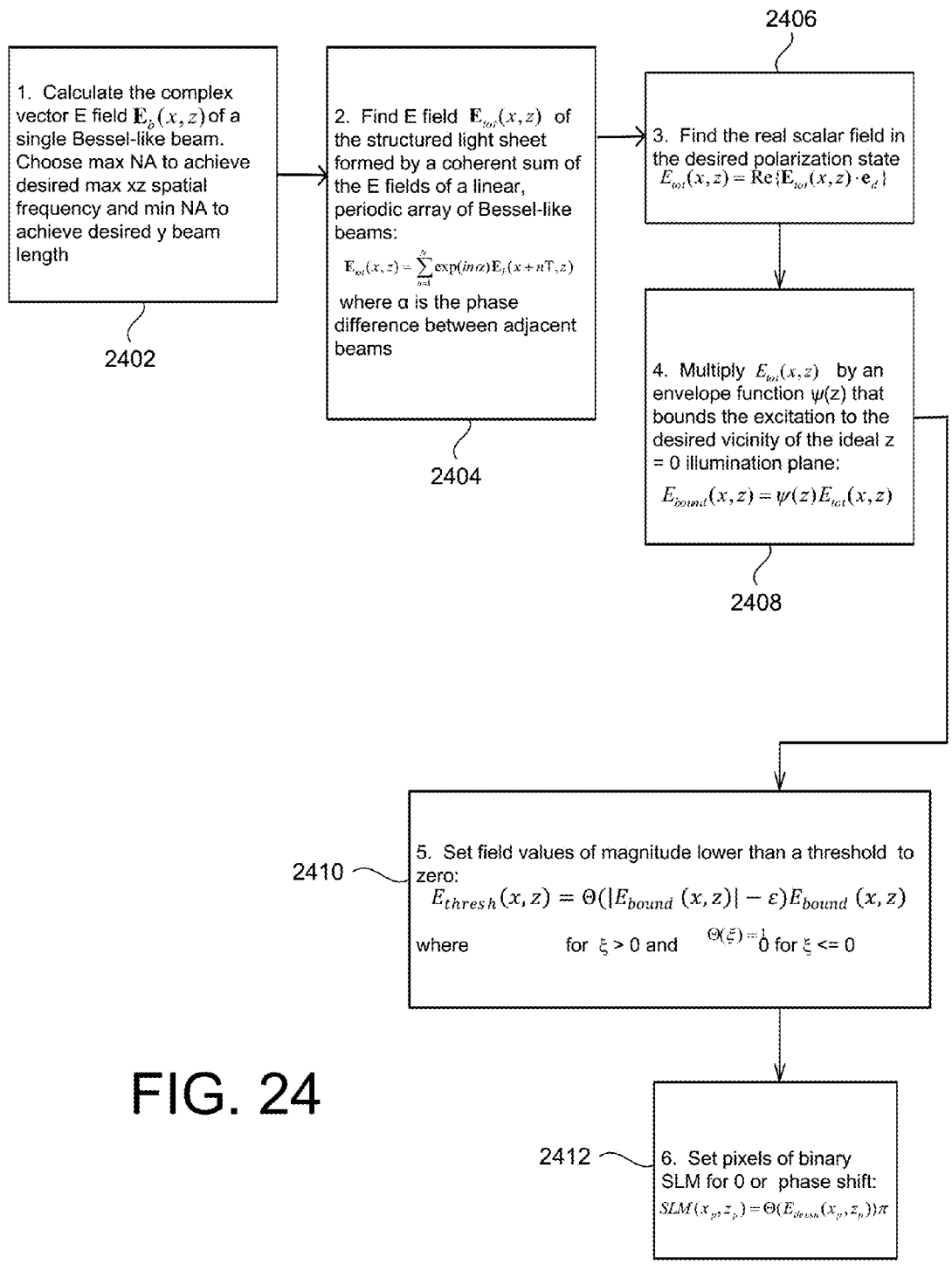
FIG. 24 is a flowchart of a process of determining a pattern to apply to a binary spatial light modulator, which will produce a coherent structured light sheet having a low height in the Z direction over a sufficient length in the Y direction to image samples of interest.

FIG. 24 is a flowchart of a process 2400 of determining a pattern to apply to a binary spatial light modulator, which will produce a coherent structured light sheet having a relatively low thickness in the Z direction over a sufficient length in the Y direction to image samples of interest. In the process 2400, the complex electric field $$E_b(x,z)$$

of a single Bessel-like beam propagating in the Y direction into the sample is calculated (step 2402). The complex electric field is chosen based on a maximum NA to achieve a desired maximum X-Z spatial frequency and based on a minimum NA to achieve a desired beam length in the Y direction. Then, the complex electric field $$E_{tot}(x,z)$$

of the structured light sheet that is formed by a coherent sum of a plurality of Bessel-like beams in a linear periodic array of Bessel-like beams can be calculated (step 2404). The total complex electric field of the array of beams can be expressed as:

$$E_{tot}(x,z) = \sum_{n=1}^{N} \exp(in\alpha) E_b(x+nT, z)$$

where α is the phase difference between adjacent beams in the array, and for T is the spatial period of the array of beams. In some implementations, α can be set equal to 0 or π (i.e., all beams can have the same phase, or beams can have alternating opposite phases). Then, the real scalar field in the desired polarization state can be determined (step 2406), where the real scalar field is given by:

$$E_{tot}(x,z) = \text{Re}\{E_{tot}(x,z) \cdot e_d\}.$$

Next, the real scalar field can be multiplied by an envelope function ψ(z) that bounds the excitation light to the desired vicinity of the ideal Z=0 illumination plane (step 2408). The product of the real scalar field and the envelope function gives the function for the bound field:

$$E_{bound}(x,z) = \psi(z) E_{tot}(x,z).$$

In some implementations, the envelope function can be a Gaussian function:

$$\psi(z) = \exp(-z^2/a^2)$$

Then, the field values having a magnitude lower than a threshold value, ε, can be set to zero (step 2410). The thresholding step can be expressed mathematically as:

$$E_{thresh}(x,z) = \Theta(|E_{bound}(x,z)| - \epsilon) E_{bound}(x,z)$$

where Θ(ξ)=1, for ξ>0 and 0 for ξ<0. Then, individual pixels values of a binary SLM that is used as the WME 2312 can be set to impose a 0 or π phase shift on light that interacts with the SLM (step 2412), according to:

$$SLM(x_p, z_p) = \Theta(E_{thresh}(x_p, z_p))\pi,$$

where the "p" subscript references an individual pixel of the SLM.

Figure 25A:
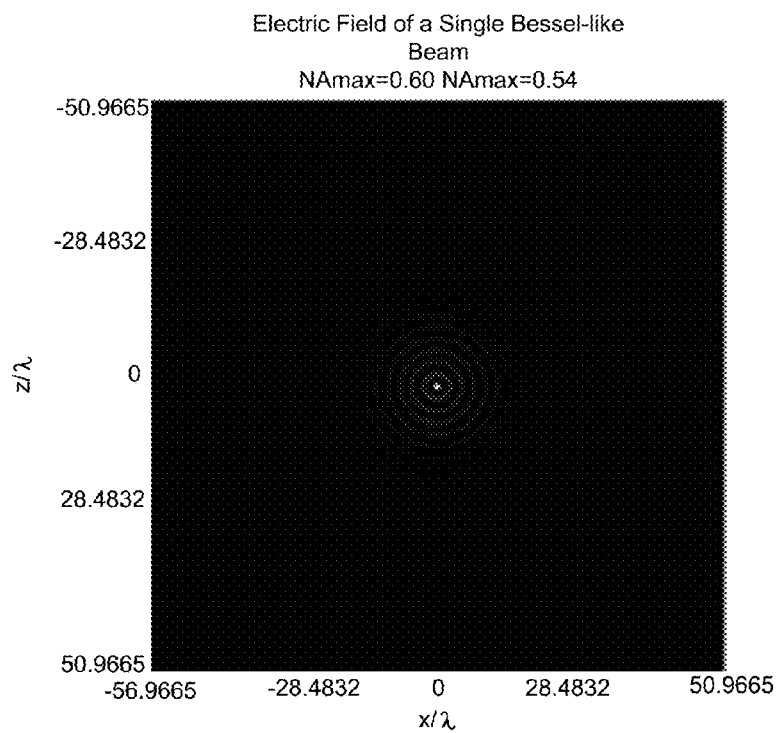
FIGS. 25A, 25B, 25C, 25D, 25E, and 25F show a series graphical illustrations of the process of FIG. 24.

FIGS. 25A, 25B, 25C, 25D, 25E, and 25F show a series of graphical illustrations of the process 2400, when the processes used to generate a thin array of structured excitation radiation is swept in the X direction to generate a plane of excitation illumination. FIG. 25A illustrates a cross-sectional profile in the X-Z plane of a Bessel like beam propagating in the Y direction. The particular cross section shown in FIG. 25A is for a Bessel-like beam having a maximum numerical aperture of 0.60 and a minimum numerical aperture of 0.54. Higher electric field strengths are shown by whiter regions in FIG. 25A.

Figure 25B:
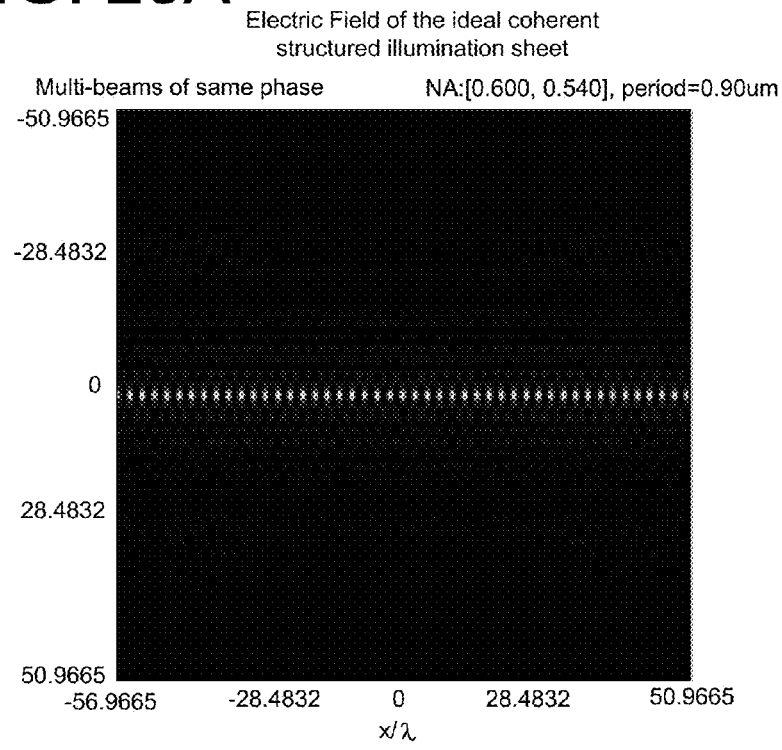

FIG. 25B illustrates the electric field, in the X-Z plane, of a structured light sheet formed by coherent sum of a linear, periodic array of Bessel-like beams that propagate in the Y direction. The individual Bessel-like beams have a maximum numerical aperture of 0.60 and a minimum numerical aperture is 0.54. The wavelength of the light is 488 nm, and the period of the array of beams is 0.90 μm, and the individual beams of the array all have the same phase. Higher electric field strengths are shown by whiter regions in FIG. 25B. The lengths shown on the axes of the panels of FIGS. 25A, 25B, 25C, 25D, 25E, and 25F are normalized to the wavelength of light in the medium within the sample chamber 1944.

Figure 25C:
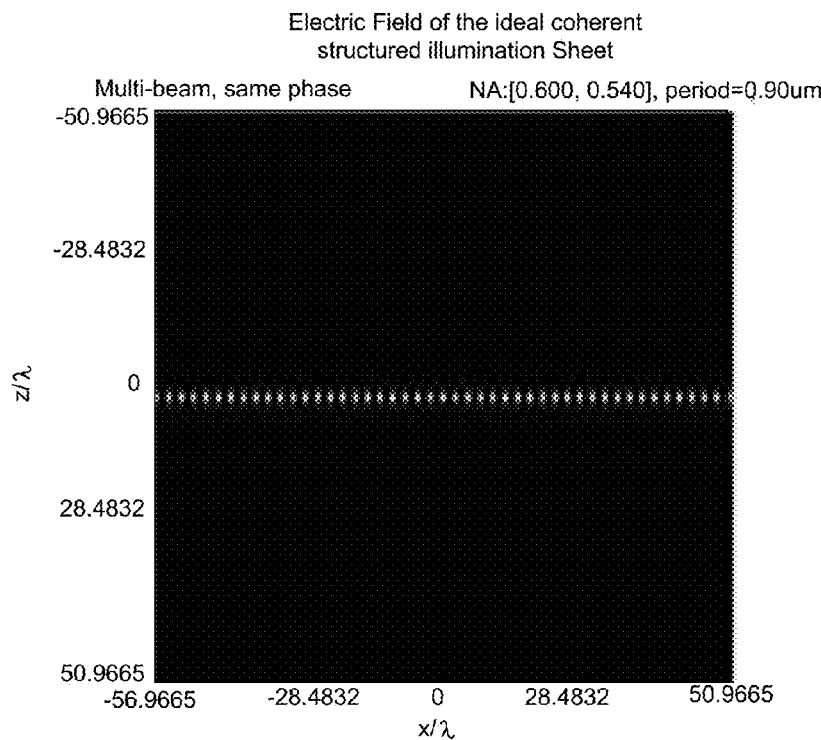
Figure 25D:
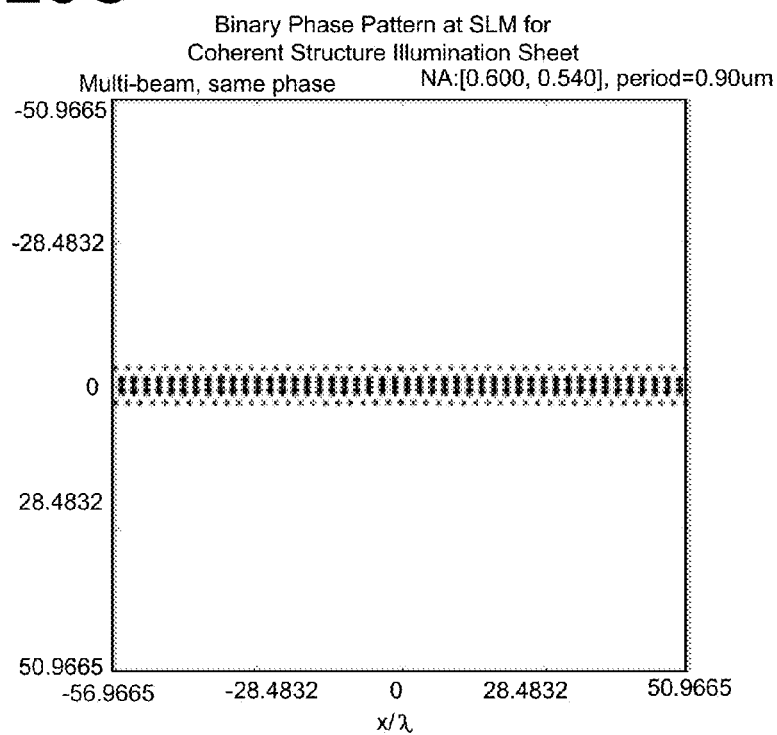
Figure 25E:
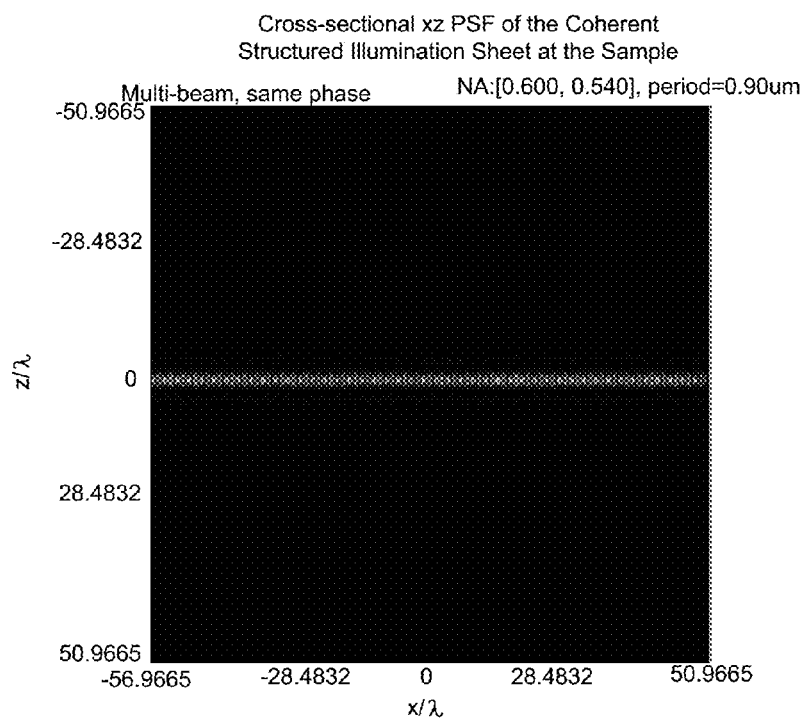
Figure 25F:
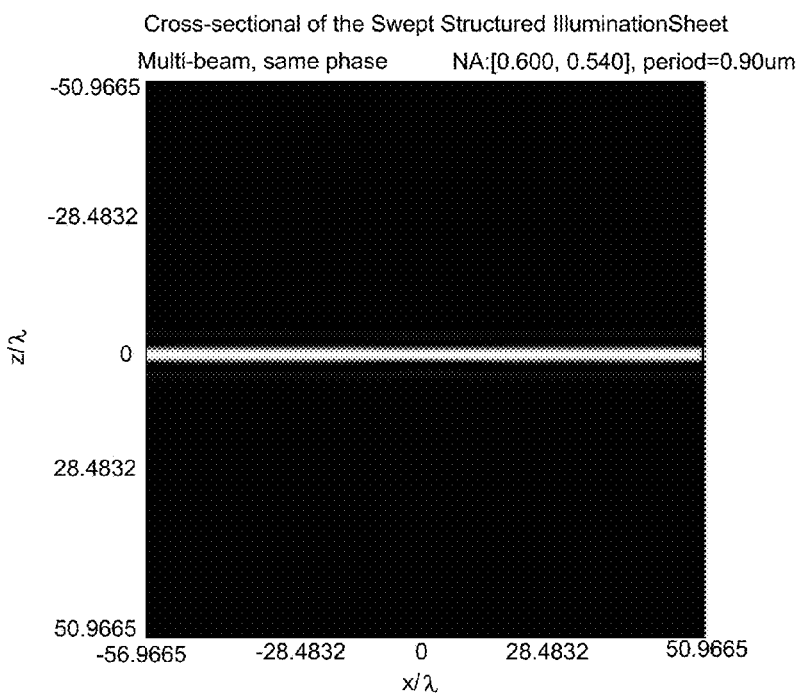

FIG. 25C illustrates the electric field, in the XZ plane, of the structured light sheet of FIG. 25B after a Gaussian envelope function has been applied to the field of the light sheet to bound the light sheet in the Z direction. Higher electric field strengths are shown by whiter regions. FIG. 25D illustrates the pattern of phase shifts applied to individual pixels of a binary spatial light modulator to generate the field shown in FIG. 25C. Pixels generating a phase shift of π are shown in black, and pixels generating a phase shift of zero are shown in white. FIG. 25E illustrates the cross-sectional point spread function, in the X-Z plane, of the structured plane of excitation radiation that is produced in the sample by the coherent array of Bessel-like beams, which are generated by the pattern on the spatial light modulator shown in FIG. 25D. Higher light intensities are shown by whiter regions. FIG. 25F illustrates the excitation beam intensity that is produced in the sample when the array of Bessel-like beams is swept or dithered in the X direction. Higher intensities are shown by whiter regions.

Changing the period of the array of the coherent Bessel-like beams can affect the overall electric field pattern resulting from the interference of the plurality of beams. In particular, for different periods of the array, the resulting electric field interference pattern can extend relatively more or less in the Z direction. This effect can be exploited to determine parameters of the coherent array that can be useful for generating images of the sample using super resolution structured illumination techniques as well as using a thin sheet of structured illumination that is swept in the X direction.

Figure 26A:
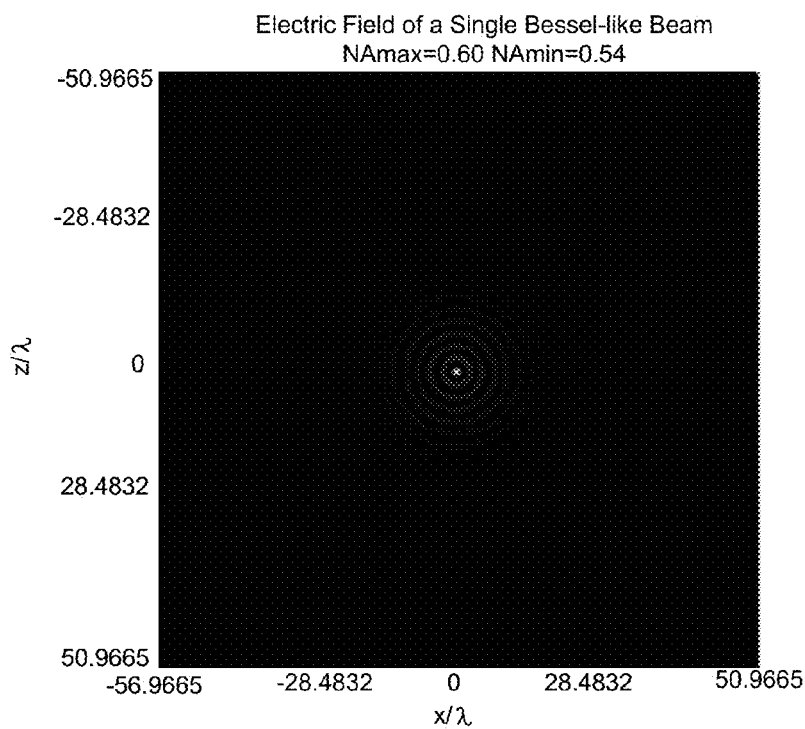
FIGS. 26A, 26B, 26C, 26D, 26E, and 26F show a series of graphical illustrations of the process shown in FIG. 24.

FIGS. 26A, 26B, 26C, 26D, 26E, and 26F show a series graphical illustrations of the process 2400, when the plane is used to generate an array of structured excitation radiation that is used to generate images of the sample using super resolution structured illumination techniques. Like FIG. 25A, FIG. 26A illustrates a cross-sectional profile in the X-Z plane of a Bessel like beam propagating in the Y direction. The particular cross section shown in FIG. 26A is identical to that of FIG. 25A and is for a Bessel-like beam having a maximum numerical aperture of 0.60 and a minimum numerical aperture of 0.54. The lengths shown on the axes of the panels of FIGS. 26A, 26B, 26C, 26D, 26E, and 26F are normalized to the wavelength of light in the medium within the sample chamber 1944.

Figure 26B:
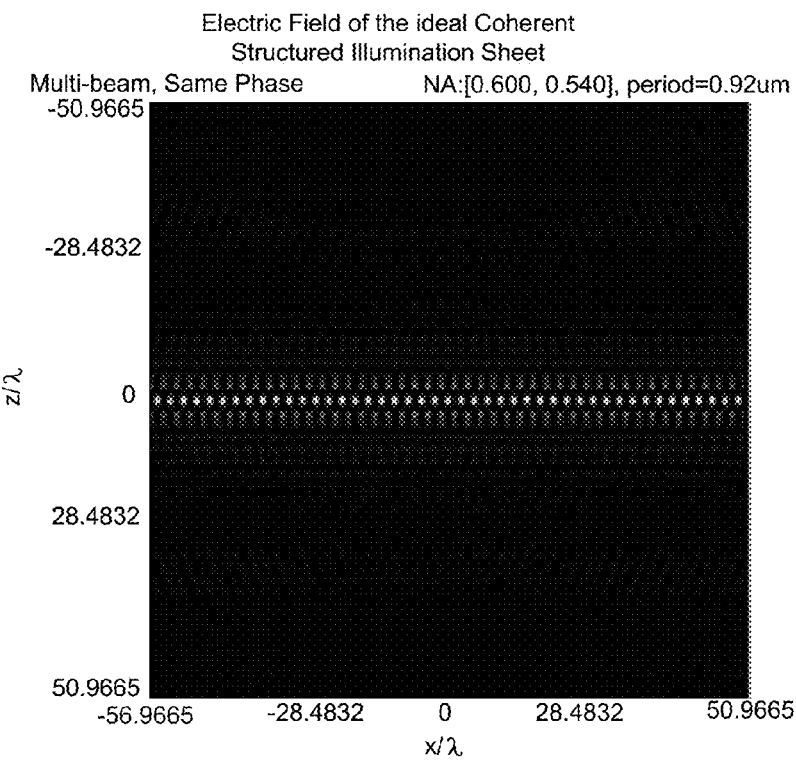

FIG. 26B illustrates the electric field, in the X-Z plane, of a structured light sheet formed by a coherent sum of a linear, periodic array of Bessel-like beams that propagate in the Y direction. The individual Bessel-like beams have a maximum numerical aperture of 0.60 and a minimum numerical aperture is 0.54. The wavelength of the light is 488 nm, and the period of the array of beams is 0.92 μm and the individual beams of the array all have the same phase. Thus, the period of the array illustrated in FIG. 26B is 0.02 μm longer than the period of the array illustrated in FIG. 25B.

Figure 26C:
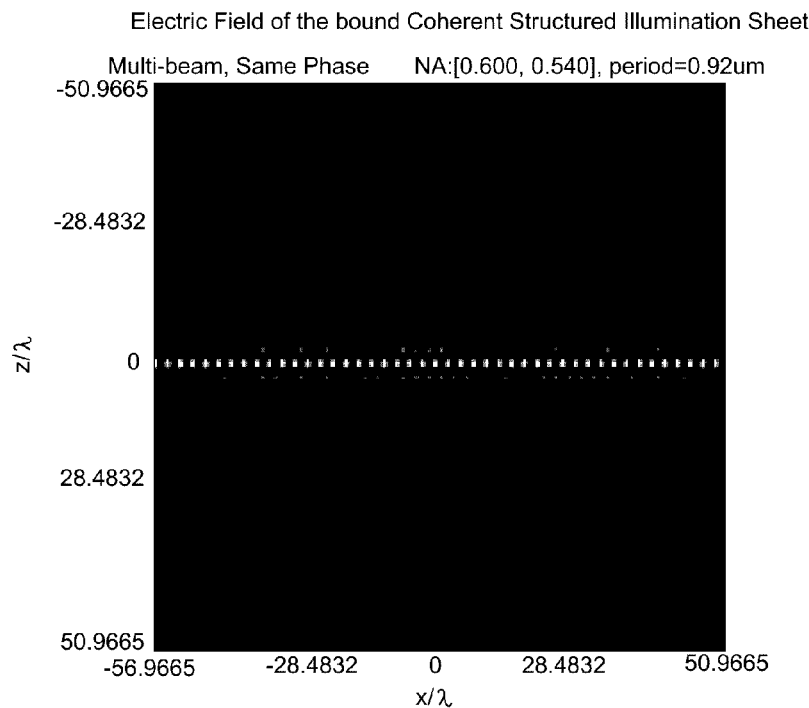

FIG. 26C illustrates the electric field, in the XZ plane, of the structured light sheet of FIG. 26B after a Gaussian envelope function has been applied to the field of the light sheet to bound the light sheet in the Z direction. Because the structured light sheets shown in FIGS. 26A, 26B, 26C, 26D, 26E, and 26F are to be used for super resolution structured illumination microscopy, in which it may be desirable to have the electric field extend further in the Z direction then when using the light sheet in a swept sheet mode, and therefore the envelope (or "bounding") function used in FIG. 26C may be relatively more relaxed than the bounding function used in FIG. 25C.

Figure 26D:
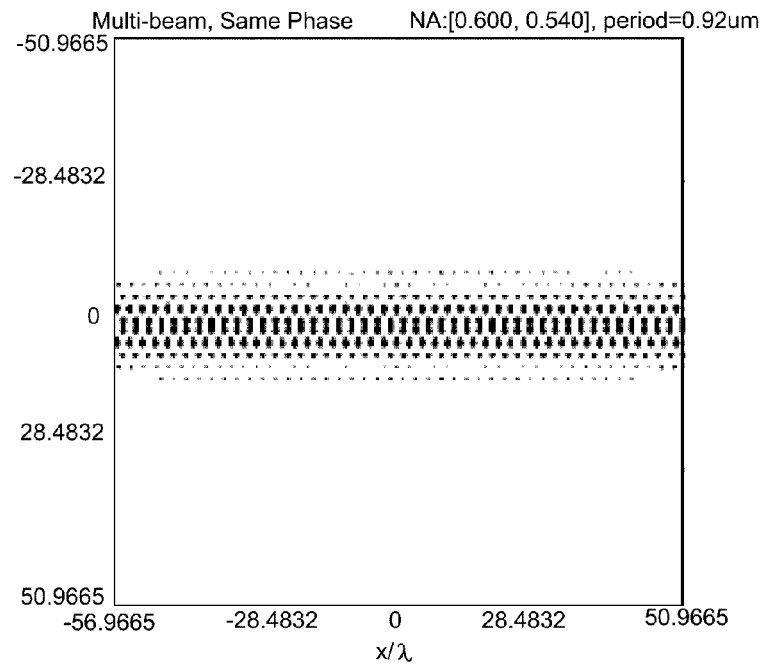
Figure 26E:
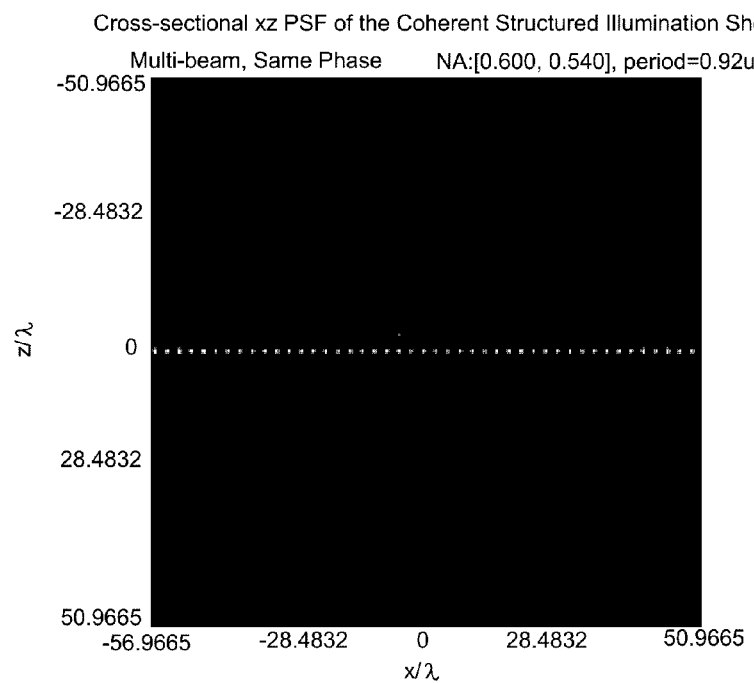
Figure 26F:
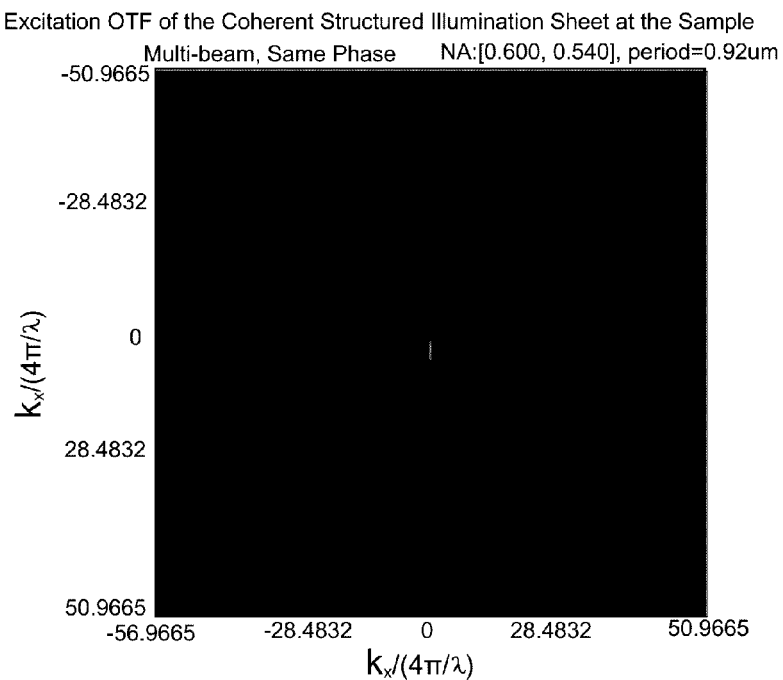

FIG. 26D illustrates the pattern of phase shifts applied to individual pixels of a binary spatial light modulator to generate the field shown in FIG. 26C. Pixels generating a phase shift of π are shown in black, and pixels generating a phase shift of zero are shown in white. FIG. 26E illustrates the cross-sectional point spread function, in the X-Z plane, of the structured plane of excitation radiation that is produced in the sample by the coherent array of Bessel-like beams, which are generated by the pattern on the spatial light modulator shown in FIG. 26D. FIG. 26F illustrates the modulation transfer function, which corresponds to the point spread functions shown in FIG. 26E. All of the MTFs are normalized to $4\pi/\lambda$, where $\lambda$ is the wavelength of light in the medium within the sample chamber 1944.

As can be seen from the electric field patterns and point spread function patterns in FIGS. 25 and 26, the coherent superposition of a plurality of Bessel-like beams bears little resemblance to the electric field patterns and point spread function patterns of individual Bessel-like beams. As is evident from a comparison of FIGS. 25A, 25B, 25C, 25D, 25E, and 25F and FIGS. 26A, 26B, 26C, 26D, 26E, and 26F, changing the period of the array of beams causes large changes in optical properties of the optical lattices (e.g., the period, symmetry, and degree of bounding in the Z direction of the lattices) that result from interference between the beams of the array. Instead, the coherent superposition of an array of Bessel-like beams, in general, forms a spatially-structured plane of excitation radiation that can be used to excite optical labels within a sample, which then emit light that is detected and used to generate an image of the sample. In some implementations, the spatially-structured plane of excitation radiation can be swept in a direction parallel to the plane to generate a thin sheet of excitation radiation. In some implementations, the spatially-structured plane of excitation radiation can be translated in discrete steps in a direction parallel to the plane and emit light can be detected when the plane is in each of the different positions. Then, the light detected from the sample when the plane is in each of the different positions can be algorithmically combined to generate a super resolution image of the sample.

FIGS. 27A, 27B, 27C, 27D, 27E, and 27F are schematic diagrams of the intensities of different modes of excitation radiation that is provided to the sample. FIG. 27A is a cross-sectional in the X-Z plane of a Bessel-like beam propagating in the Y direction. The particular cross section shown in FIG. 27A is for a Bessel-like beam having a wavelength of 488 nm and having a maximum numerical aperture of 0.60 and a minimum numerical aperture of 0.54. Higher intensities are shown by whiter regions. When the Bessel-like beam of FIG. 27A is swept in the X direction, then the time-averaged intensities in the X-Z plane shown in FIG. 27B results. FIG. 27C is a cross-sectional in the X-Z plane of a superposition of incoherent Bessel-like beams propagating in the Y direction, such as would occur if the single Bessel-like beam in FIG. 27A were moved in discrete steps. The pattern shown in FIG. 27C is for a 488 nm Bessel-like beam having a maximum numerical aperture of 0.60 and a minimum numerical aperture of 0.54, stepped in units of 0.90 μm. When multiple instances of the array of Bessel-like beams of FIG. 27C are moved in small increments in the X direction and the resulting signal integrated on a camera, then the time-averaged intensity in the X-Z plane shown in FIG. 27D results. FIG. 27E is a cross-section in the X-Z plane of a superposition of coherent Bessel-like beams propagating in the Y direction. The pattern shown in FIG. 27E is for an array of 488 nm Bessel-like beams having a maximum numerical aperture of 0.60 and a minimum numerical aperture of 0.54, with individual beams of the array being spaced 0.90 µm from each other. When the array of Bessel-like beams of FIG. 27E is swept or dithered in the X direction, then the time-averaged intensity in the X-Z plane shown in FIG. 27F results. As can be seen by a comparison of FIG. 27B, FIG. 27D, and FIG. 27F, the coherent array of Bessel-like beams can result in a light sheet that is more tightly confined in the Z direction that a light sheet that is produced by sweeping a single Bessel-like beams (FIG. 27B) or a light sheet that is produced by sweeping an incoherent array of Bessel-like beams (FIG. 27D).

Referring again to the electric field patterns in FIGS. 25B and 26B, and point spread function intensity patterns in FIGS. 25E and 26E, it can be seen that the coherent superposition of a plurality of Bessel-like beams forms a spatially-structured plane of excitation radiation. These patterns can be viewed as optical lattices that are created by interference within the sample between different beamlets of the beam that is modulated by the spatial light modulator 2312 shown in FIG. 23 and then enter the sample 2346 through the excitation objective 2342. Therefore, in some implementations, a pattern can be applied to the WME 2312 that creates an optical lattice within the sample, which can be used to generate a spatially-structured plane of excitation radiation that can be used to generate images of the sample 2346.

Figure 28:
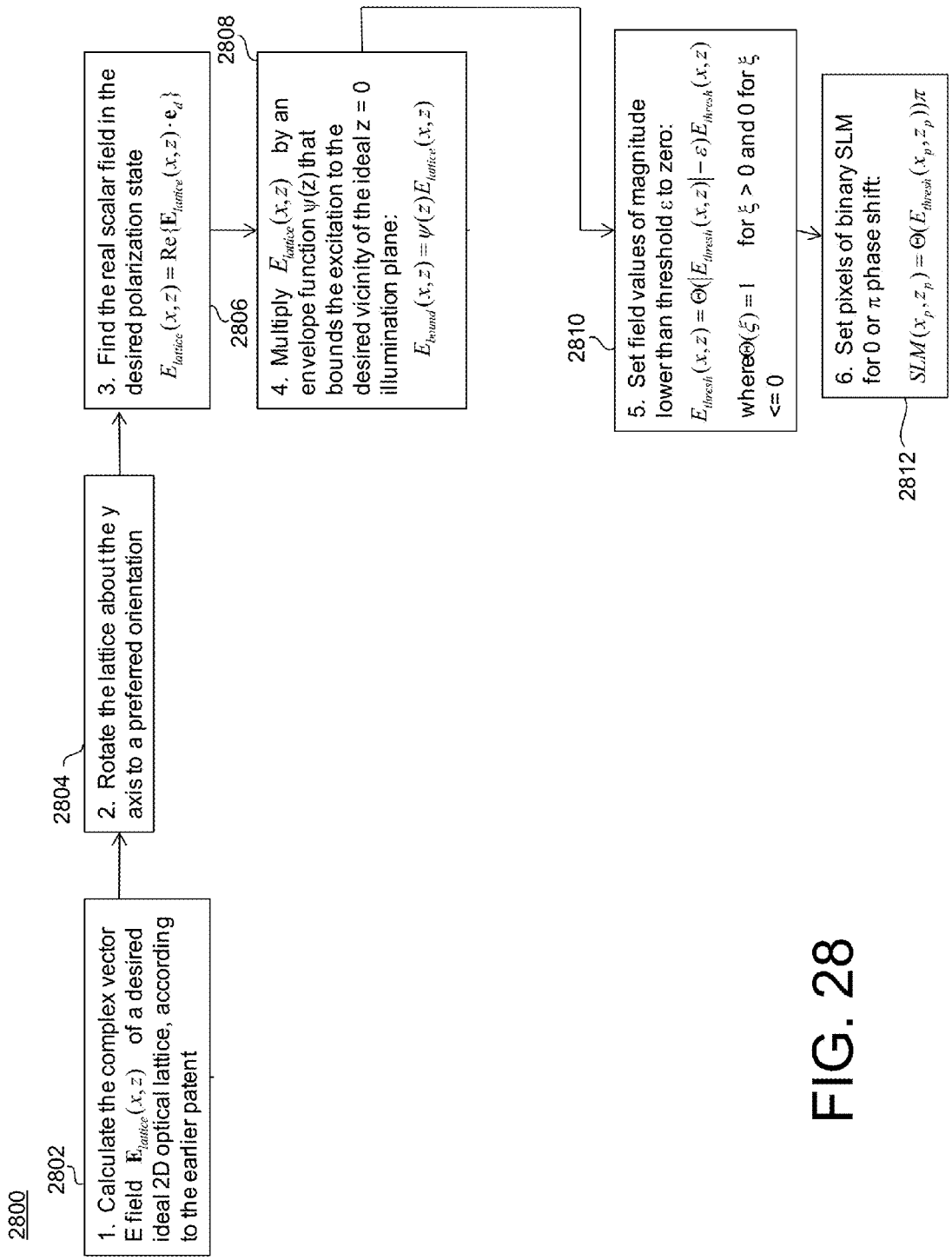
FIG. 28 is a flowchart of a process of determining a pattern to apply to a binary spatial light modulator, which will produce an optical lattice within the sample, where the optical lattice can be used as a coherent structured light sheet having a relatively low thickness extent in the Z direction over a sufficient length in the Y direction to image samples of interest.

FIG. 28 is a flowchart of a process 2800 of determining a pattern to apply to a binary spatial light modulator, which will produce an optical lattice within the sample, where the optical lattice can be used as a coherent structured light sheet having a relatively low thickness extent in the Z direction over a sufficient length in the Y direction to image samples of interest. In the process 2800, the complex electric field $E_{lattice}(x,z)$ of a selected two-dimensional 2D optical lattice can be calculated (step 2802). The selected optical lattice can be, for example, a fundamental lattice, a sparse lattice, a composite lattice, or a maximally symmetric composite lattice, as described in U.S. Pat. No. 7,609,391, entitled "Optical Lattice Microscopy," issued on Oct. 27, 2409, which is incorporated herein by reference. In some implementations, a maximally symmetric composite lattice can be selected to provide tight confinement of the excitation radiation in the Z direction when generating images of the sample using the swept sheet mode and to provide high spatial frequency components in the XZ plane when generating images of the sample using the super resolution, structured illumination mode. In some implementations, maximally symmetric composite hexagonal and square lattices can be used, because they can provide more wavevectors than lattices with other symmetry.

Then, the lattice can be rotated about the Y axis to a desired orientation (step 2804). For example, an orientation of the lattice in which lattice wavevectors lie along the X axis facilitates the construction of structured light sheets that are tightly confined in the Z direction. In another example, an orientation of the optical lattice in which a line of lattice intensity maxima lies along the x-axis can be desirable. In another example, an optical lattice having a periodicity and orientation such that adjacent lines of the lattice maximum along the X direction are separated by more than the desired light sheet thickness in the Z direction can be useful when using the lattice to generate images of the sample with the swept sheet mode. However, the lines of lattice maximum along the X direction should be separated by less than the desired light sheet thickness when using the super resolution, structured illumination mode to generate images of the sample.

After the orientation of the lattice is determined, the real scalar field of the optical lattice can be determined (step 2806), where the real scalar field is given by:

$$E_{lattice}(x,z) = \text{Re}\{E_{lattice}(x,z) \cdot e_d\},$$

Where $e_d$ is a vector in the direction of the desired polarization of the electric field. Next, the real scalar field of the optical lattice can be multiplied by an envelope function $\psi(z)$ that bounds the excitation light to the desired vicinity of the ideal Z=0 illumination plane (step 2808). The product of the real scalar field and the envelope function gives the function for the bound field:

$$E_{bound}(x,z) = \psi(z) E_{lattice}(x,z).$$

In some implementations, the envelope function can be a Gaussian function:

$$\psi(z) = \exp(-z^2/a^2)$$

Then, the field values having a magnitude lower than a threshold value, $\epsilon$, can be set to zero (step 2810). The thresholding step can be expressed mathematically as:

$$E_{thresh}(x,z) = \Theta(|E_{bound}(x,z)| - \epsilon) E_{bound}(x,z)$$

where $\Theta(\xi)=1$, for $\xi>0$ and 0 for $\xi<0$. Then, individual pixels values of a binary SLM that is used as the WME 2312 can be set to impose a 0 or $\pi$ phase shift on light that interacts with the SLM (step 2812), according to:

$$\text{SLM}(x_p,z_p) = \Theta(E_{thresh}(x_p,z_p))\pi,$$

where the "p" subscript references an individual pixel of the SLM. This pattern imposed on the SLM, which is conjugate to the sample 2346, will create an optical lattice within the sample.

Figure 29A:
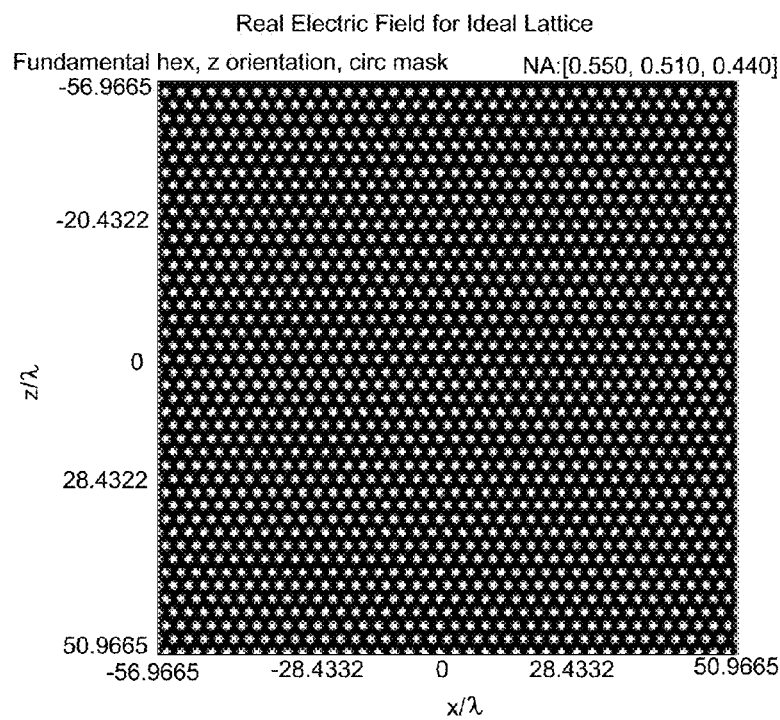
FIGS. 29A, 29B, 29C, 29D, and 29E show a series of graphical illustrations of the process shown in FIG. 28, when the process is used to generate an optical lattice of structured excitation radiation that is swept in the X direction to generate a plane of excitation illumination.

FIGS. 29A, 29B, 29C, 29D, and 29E show a series of graphical illustrations of the process 2800, when the process is used to generate an optical lattice of structured excitation radiation that is swept in the X direction to generate a plane of excitation illumination. FIG. 29A illustrates a cross-sectional profile in the X-Z plane of an ideal two-dimensional fundamental hexagonal lattice that is oriented in the Z direction. The optical lattice is formed by the coherent superposition of a plurality of beams that all converge on a cone corresponding to a numerical aperture of 0.51. The profile shows the real electric field strengths in the optical lattice, with higher electric field strengths being shown by whiter regions. The lengths shown on the axes of the panels of FIGS. 29A, 29B, 29C, 29D, and 29E are normalized to the wavelength of light in the medium within the sample chamber 1944.

Figure 29B:
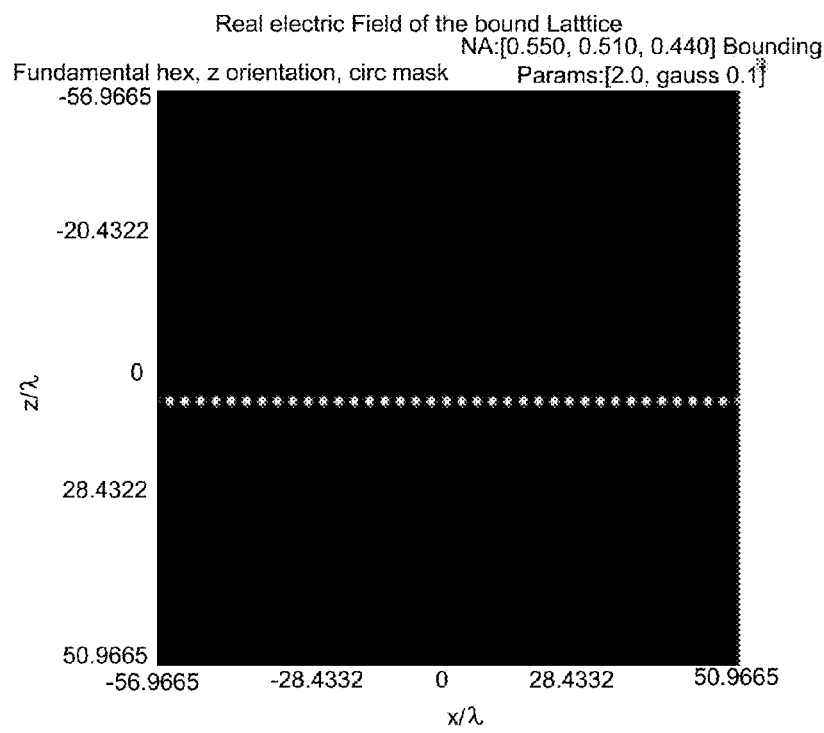
Figure 29C:
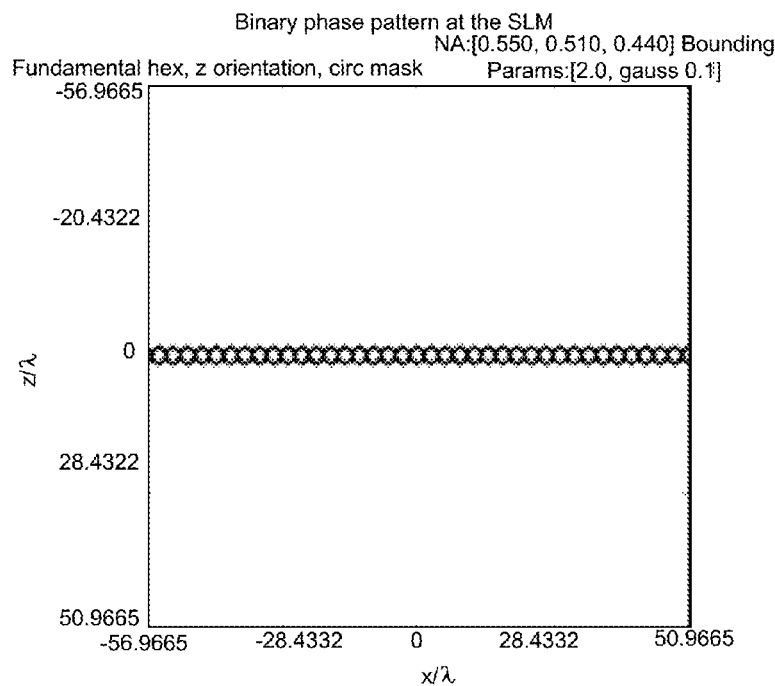
Figure 29D:
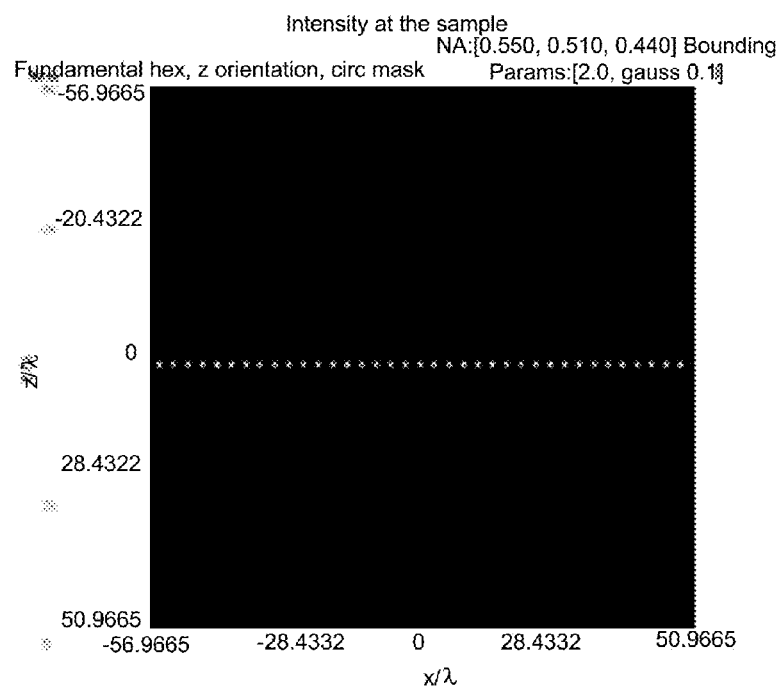
Figure 29E:
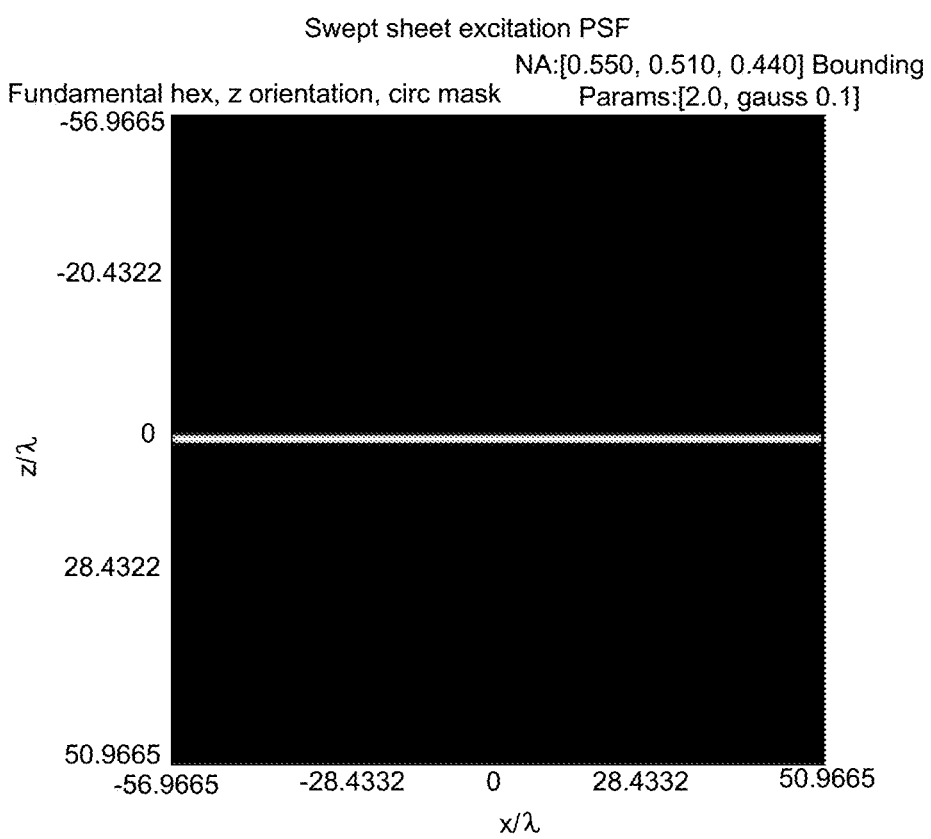

FIG. 29B illustrates the electric field, in the XZ plane, of the optical lattice of FIG. 29A after a Gaussian envelope function has been applied to the optical lattice to bound the lattice in the Z direction. Higher electric field strengths are shown by whiter regions. FIG. 29C illustrates the pattern of phase shifts applied to individual pixels of a binary spatial light modulator to generate the field shown in FIG. 29B. Pixels generating a phase shift of it are shown in black, and pixels generating a phase shift of zero are shown in white. FIG. 29D illustrates the cross-sectional point spread function, in the X-Z plane, of the structured plane of excitation radiation that is produced in the sample by the optical lattice, which is generated by the pattern on the spatial light modulator shown in FIG. 29C, and then filtered by an annular apodization mask that limits the maximum NA of the excitation to 0.55 and the minimum NA of the excitation to 0.44. Higher intensities are shown by whiter regions. FIG. 29E illustrates the excitation beam intensity that is produced in the sample when the bound optical lattice pattern in FIG. 29D is swept or dithered in the X direction. Higher intensities are shown by whiter regions.

Figure 30A:
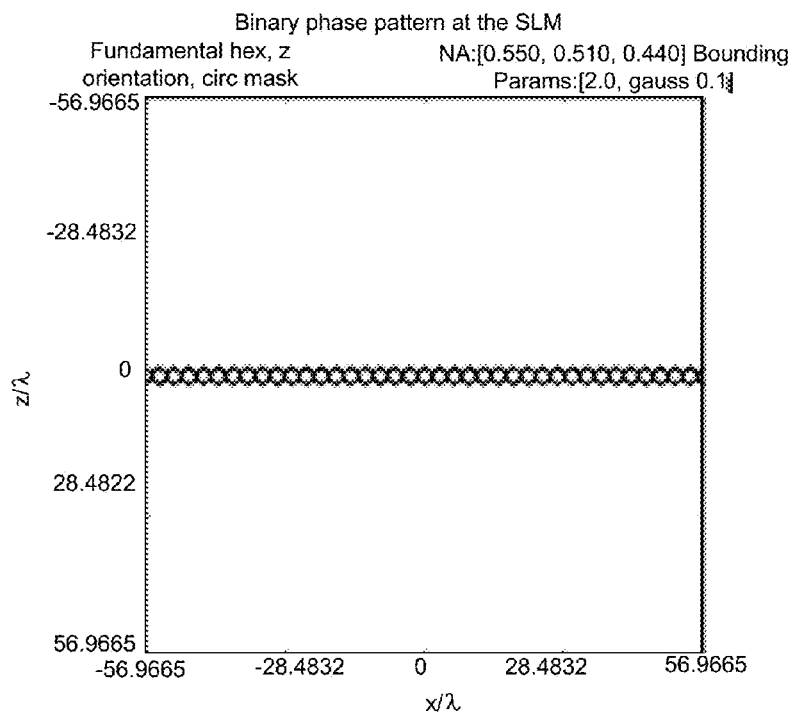
FIGS. 30A, 30B, 30C, 30D, 30E, and 30F illustrate the light patterns of at a plurality of locations along the beam path shown in FIG. 23 when the pattern shown in FIG. 29C is used on the SLM of FIG. 23.
Figure 30B:
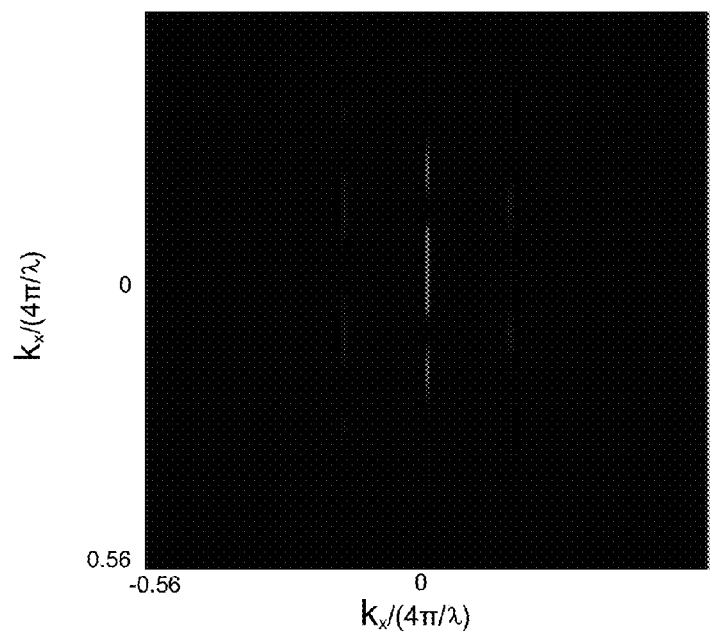
Figure 30C:
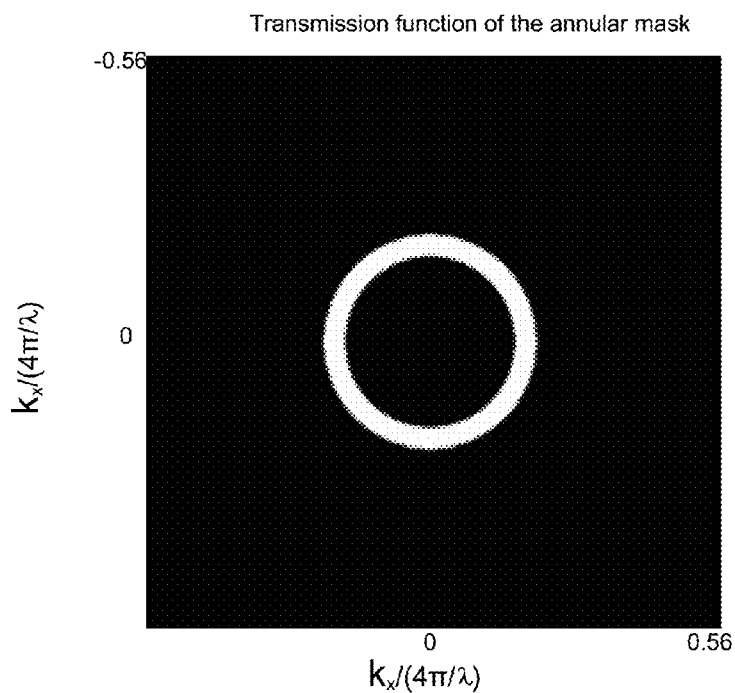
Figure 30D:
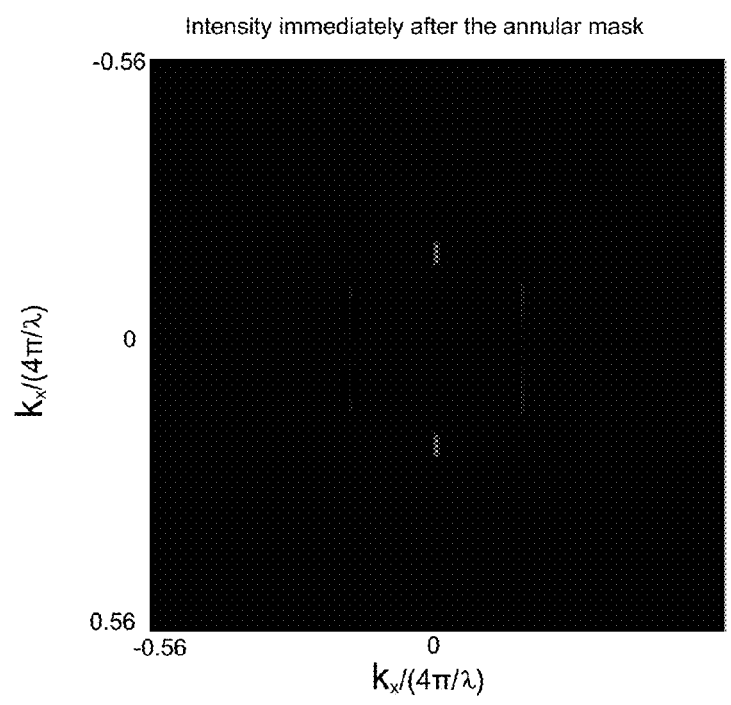
Figure 30E:
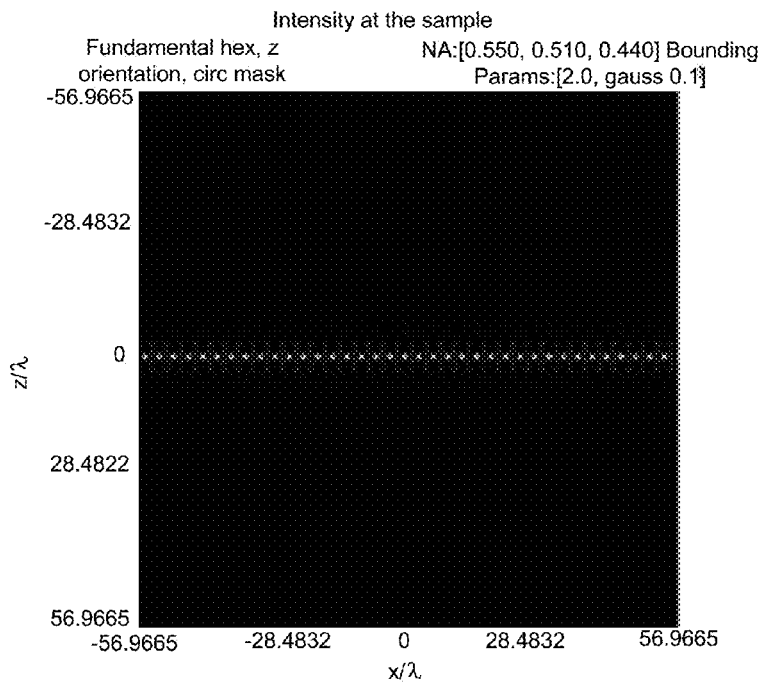
Figure 30F:
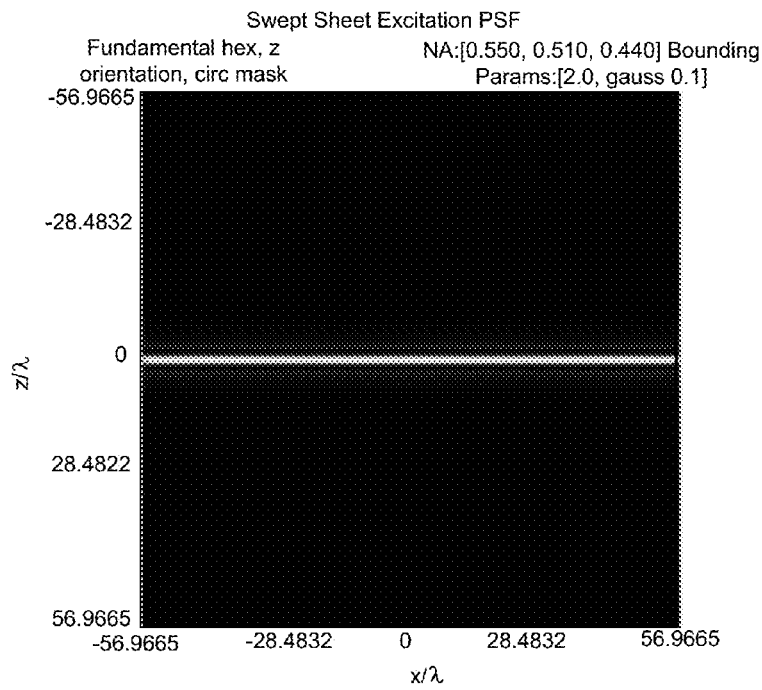

FIGS. 30A, 30B, 30C, 30D, 30E, and 30F illustrate the light patterns at a plurality of locations along the beam path shown in FIG. 23 when the pattern shown in FIG. 29C is used on the SLM 2312. For example, FIG. 30A is identical to FIG. 29C and illustrates the pattern of phase shifts applied to individual pixels of a binary spatial light modulator 2312 to generate the field shown in FIG. 29B. FIG. 30B illustrates the intensity of light that impinges on the apodization mask 2320 downstream from the SLM 2312. FIG. 30C illustrates the transmission function of the apodization mask 2320, and FIG. 30D illustrates the intensity of light immediately after the apodization mask 2320. As shown in FIG. 30D, the pattern of the light that exists just after the apodization mask 2320, which is conjugate to the rear pupil of the excitation objective, is a plurality of six vertical slits located on a surface of a cone, and when this pattern is focused by the excitation objective 2342 to the focal plane within the sample, the optical lattice shown in FIG. 29E (which is identical to the pattern shown in FIG. 29D) results. When this optical lattice is swept or dithered in the X direction, the sheet of excitation radiation shown in FIG. 30F results. The lengths shown on the axes of the panels of FIGS. 30A, 30B, 30C, 30D, 30E, and 30F are normalized to the wavelength of light in the medium within the sample chamber 1944.

Figure 31A:
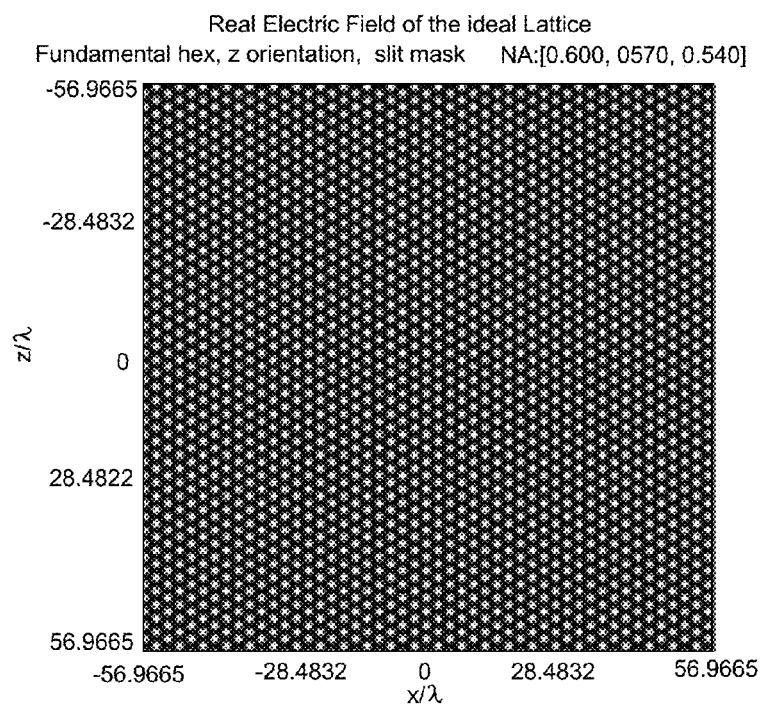
FIGS. 31A, 31B, 31C, 31D, and 31E show a series of graphical illustrations of the process, when the processes used to generate an optical lattice of structured excitation radiation that is translated in the X direction in discrete steps to generate images of the sample using superresolution, structured illumination techniques.

FIGS. 31A, 31B, 31C, 31D, and 31E show a series of graphical illustrations of the process 2800, when the processes used to generate an optical lattice of structured excitation radiation that is translated in the X direction in discrete steps to generate images of the sample using super-resolution, structured illumination techniques. FIG. 31A illustrates a cross-sectional profile in the X-Z plane of a two-dimensional fundamental hexagonal lattice that is oriented in the Z direction. The optical lattice is formed by the coherent superposition of a plurality of beams that all converge on a cone corresponding to a numerical aperture of 0.57. The lengths shown on the axes of all of the panels of FIGS. 31A, 31B, 31C, 31D, and 31E are normalized to the wavelength of light in the medium within the sample chamber 1944.

Figure 31B:
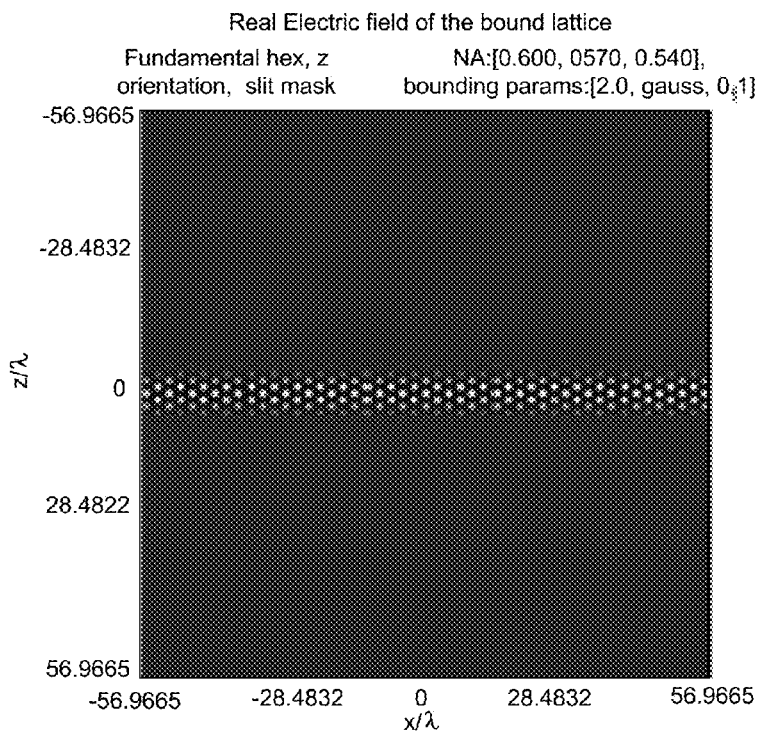
Figure 31C:
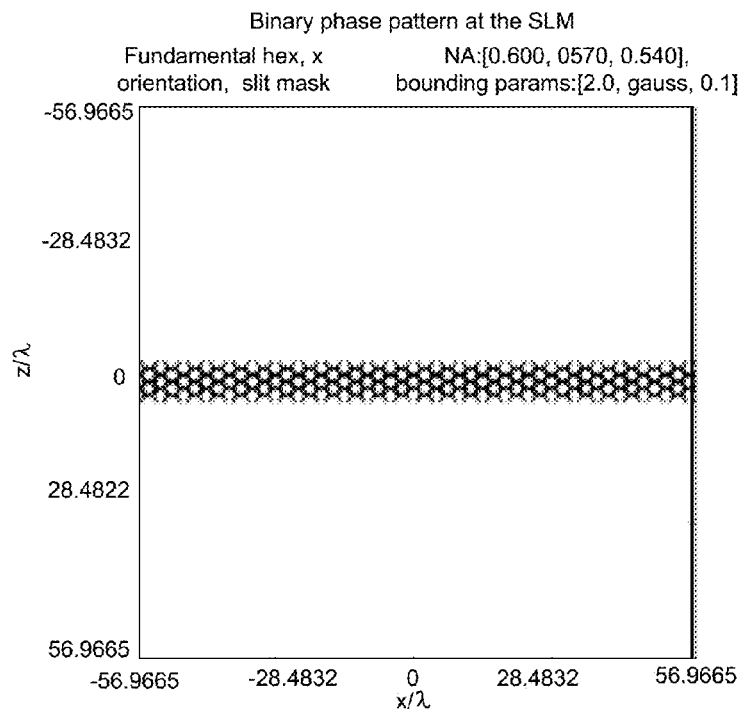
Figure 31D:
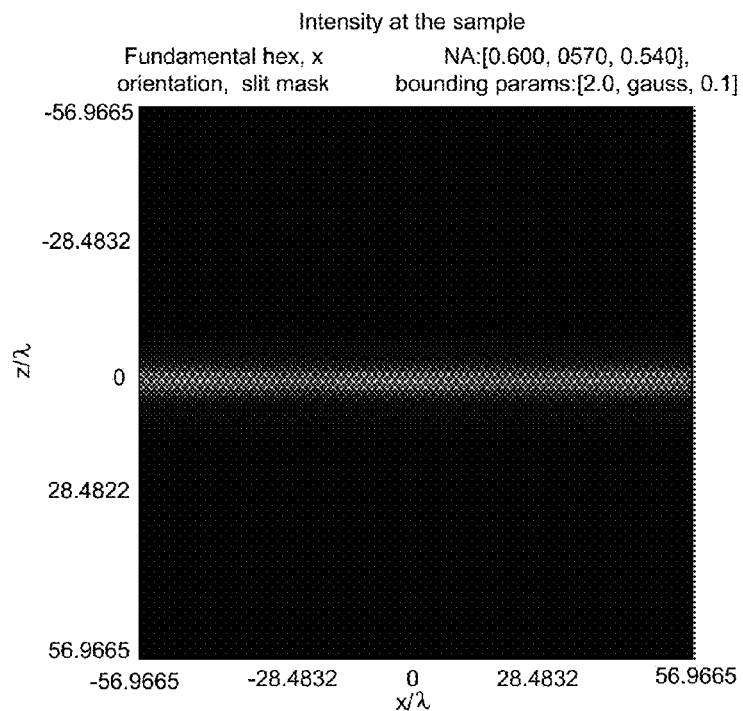
Figure 31E:
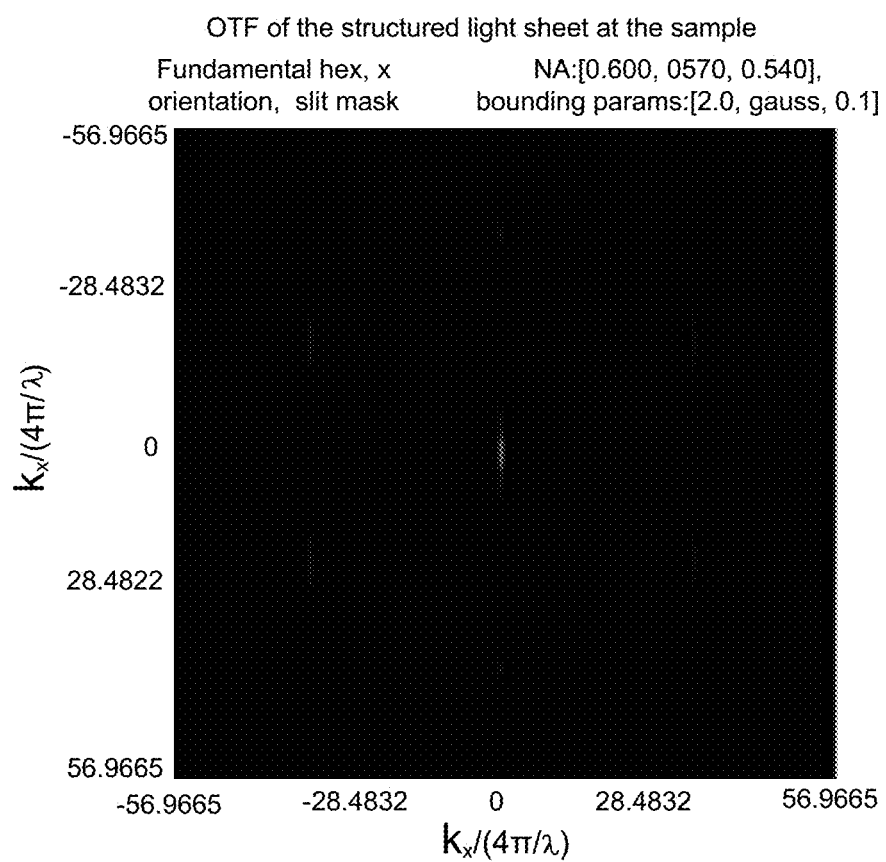

FIG. 31B illustrates the electric field, in the XZ plane, of the optical lattice of FIG. 31A after a Gaussian envelope function has been applied to the optical lattice to bound the lattice in the Z direction. Higher electric field strengths are shown by whiter regions. The envelope function used for FIG. 31B confines the lattice less tightly in the Z direction that the envelope function used for FIG. 29B. FIG. 31C illustrates the pattern of phase shifts applied to individual pixels of a binary spatial light modulator to generate the field shown in FIG. 31B. Pixels generating a phase shift of it are shown in black, and pixels generating a phase shift of zero are shown in white. FIG. 31D illustrates the cross-sectional point spread function, in the X-Z plane, of the structured plane of excitation radiation that is produced in the sample by the optical lattice, which is generated by the pattern on the spatial light modulator shown in FIG. 31C, and then filtered by an annular apodization mask that limits the maximum NA of the excitation to 0.60 and the minimum NA of the excitation to 0.54. Higher intensities are shown by whiter regions. FIG. 31E illustrates the modulation transfer function, in reciprocal space, which corresponds to the intensity pattern shown FIG. 31D. The MTF is normalized to $4\pi/\lambda$, where $\lambda$ is the wavelength of the excitation radiation. Higher spectral powers are shown by whiter regions.

Figure 32A:
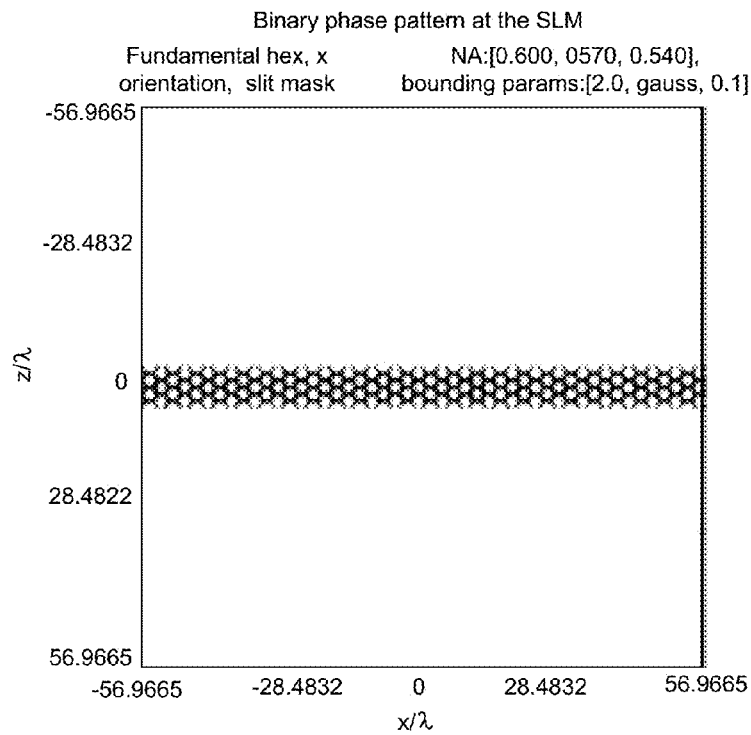
FIGS. 32A, 32B, 32C, 32D, 32E, and 32F illustrate the light patterns at a plurality of locations along the beam path shown in FIG. 23 when the pattern shown in FIG. 31C is used on the SLM of FIG. 23.
Figure 32B:
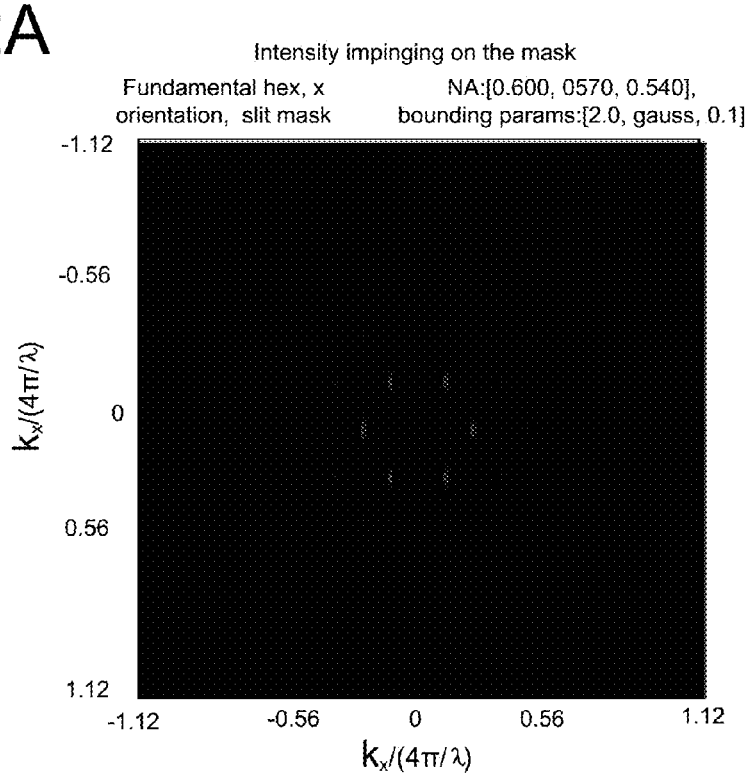
Figure 32C:
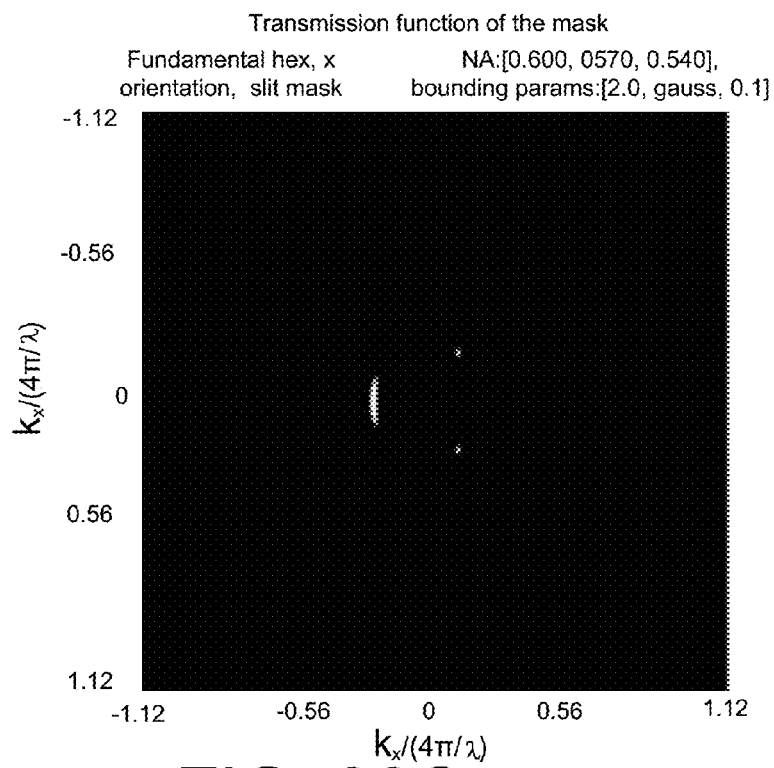
Figure 32D:
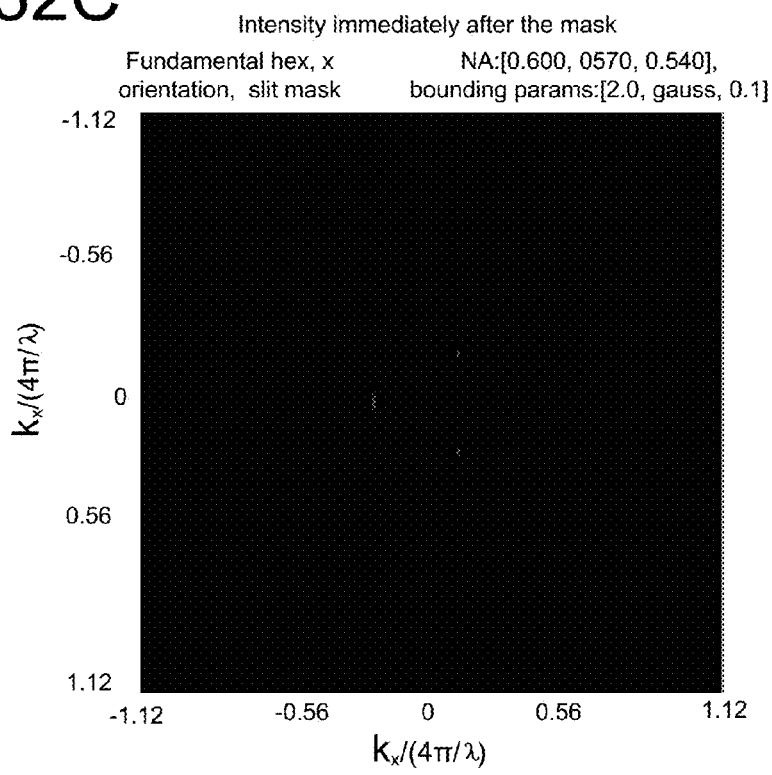
Figure 32E:
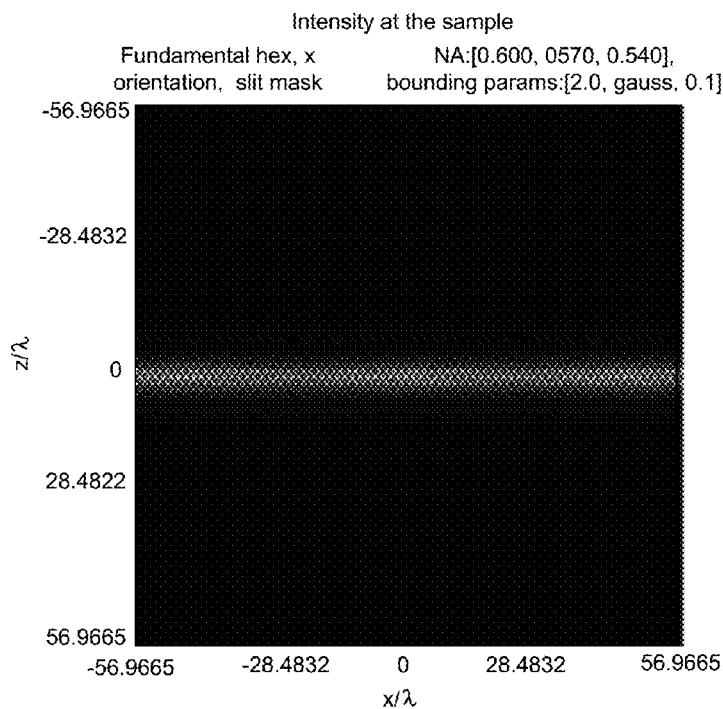
Figure 32F:
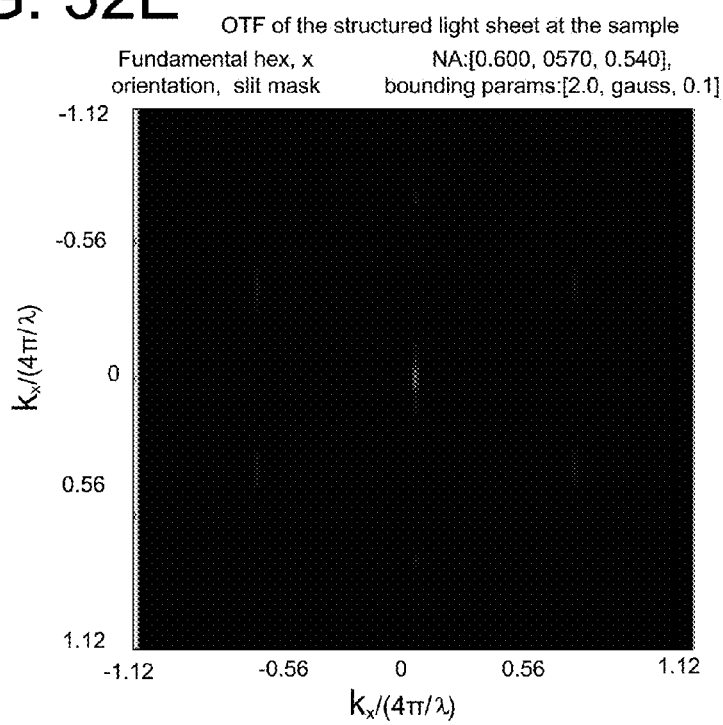

FIGS. 32A, 32B, 32C, 32D, 32E, and 32F illustrate the light patterns at a plurality of locations along the beam path shown in FIG. 23 when the pattern shown in FIG. 31C is used on the SLM 2312. For example, FIG. 32A is identical to FIG. 31C and illustrates the pattern of phase shifts applied to individual pixels of a binary spatial light modulator 2312 to generate the field shown in FIG. 31B. FIG. 32B illustrates the intensity of light that impinges on the apodization mask 2320 downstream from the SLM 2312 when the SLM includes the pattern of FIG. 32A. FIG. 32C illustrates the transmission function of the apodization mask 2320, and FIG. 32D illustrates the intensity of light immediately after the apodization mask 2320. The mask used to produce the transmission function shown in FIG. 32C includes the product of an annular mask and a mask having two slits, which transmits only three of the six beams shown in FIG. 32B. As shown in FIG. 32D, the pattern of the light that exists just after the apodization mask 2320, which is conjugate to the rear pupil of the excitation objective, is a plurality of three vertical slits located on a surface of a cone, and when this pattern is focused by the excitation objective 2342 to the focal plane within the sample, the optical lattice shown in FIG. 32E (which is identical to the pattern shown in FIG. 31D) results. The modulation transfer function for this lattice is shown in FIG. 32F. The lengths shown on the axes of all of the panels of FIGS. 32A, 32B, 32C, 32D, 32E, and 32F are normalized to the wavelength of light in the medium within the sample chamber 1944.

Referring again to FIG. 29, and, in particular, to FIG. 29B, the envelope function that are selected to bound the optical lattice to the vicinity of the Z=0 plane of the sample can have an effect on the intensity pattern of the swept light sheet shown in FIG. 29E. For example, when a strong envelope function is selected that tightly binds the optical lattice to the vicinity of the Z=0 plane, then the intensity of the optical lattice may be strongly confined to the line of intensity maxima along the Z=0 plane, but the extent of the individual maxima in the Z direction can be relatively large. On the other hand, when a weak envelope function is selected that only loosely binds the optical lattice to the vicinity of the Z=0 plane, then the optical lattice within the sample may include intensity maxima along the line of the Z=0 plane and also maxima along one or more lines that are displaced from the Z=0 plane. This phenomenon is shown in FIG. 33.

Figure 33A:
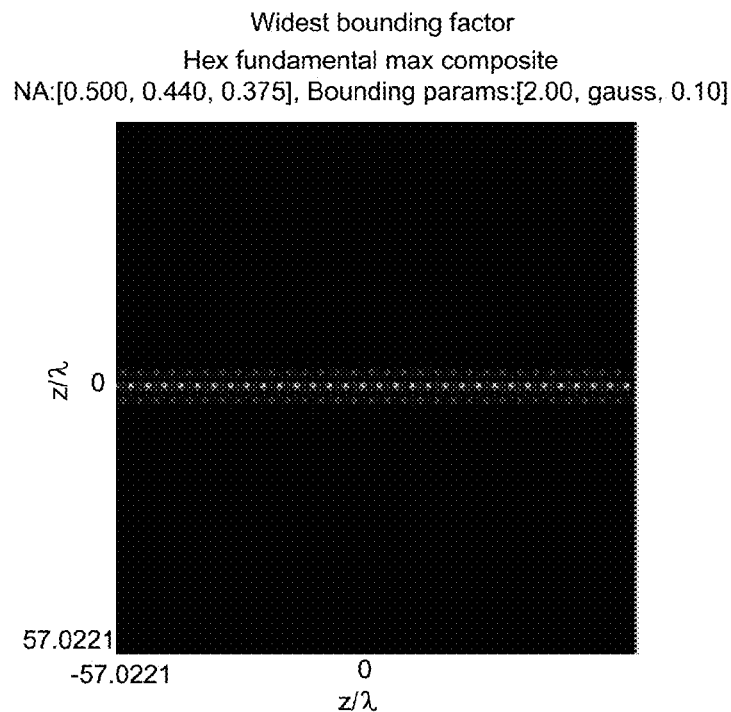
FIGS. 33A, 33B, 33C, 33D, 33E, 33F, 33G, and 33H are a plurality of graphs illustrating the effect of the Z axis bounding of the optical lattice on the light sheets produced in the sample.
Figure 33B:
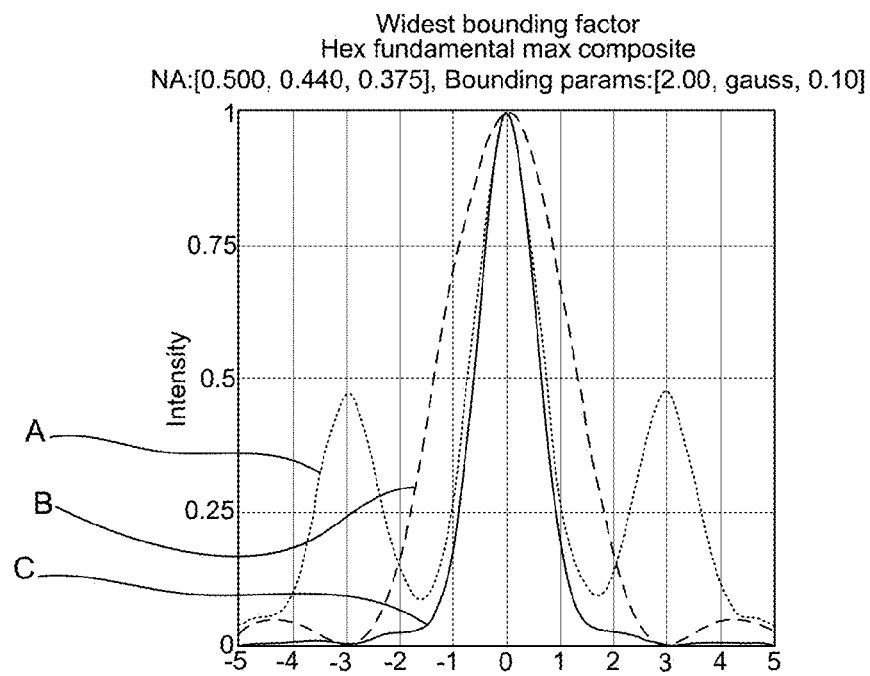

FIGS. 33A, 33B, 33C, 33D, 33E, 33F, 33G, and 33H are a plurality of graphs illustrating the effect of the Z axis bounding of the optical lattice on the light sheets produced in the sample. FIG. 33A illustrates the intensity of the optical lattice to which a wide, or weak, envelope function is applied. As can be seen in FIG. 33A, intensity maxima exist along the Z=0 plane and also a positive and negative nonzero values of Z. Sweeping or dithering this pattern in the X direction creates a light sheet whose intensity profile along the Z direction is shown in the curve A of FIG. 33B. Curve A shows side lobes peaked at three wavelengths away from the Z=0 plane. Curve B shown in FIG. 33B shows the point spread function of the detection objective 2348, and the curve C in FIG. 33B shows the normalized product of curves A and B, which is the overall point spread function of the optical system in the Z direction. In some implementations, the numerical aperture of the excitation objective and the numerical aperture of the detection objective can be selected such that the maximum intensity of a side lobe of the sheet of excitation illumination occurs at a Z position that corresponds to a minimum in the point spread function of the detection objective. In this manner, the overall point spread function shown in curve C can minimize the effect of the excitation illumination side lobes on images generated from the sample. The lengths shown on the axes of all of the panels of FIGS. 33A, 33B, 33C, 33D, 33E, 33F, 33G, and 33H are normalized to the wavelength of light in the medium within the sample chamber 1944.

Figure 33C:
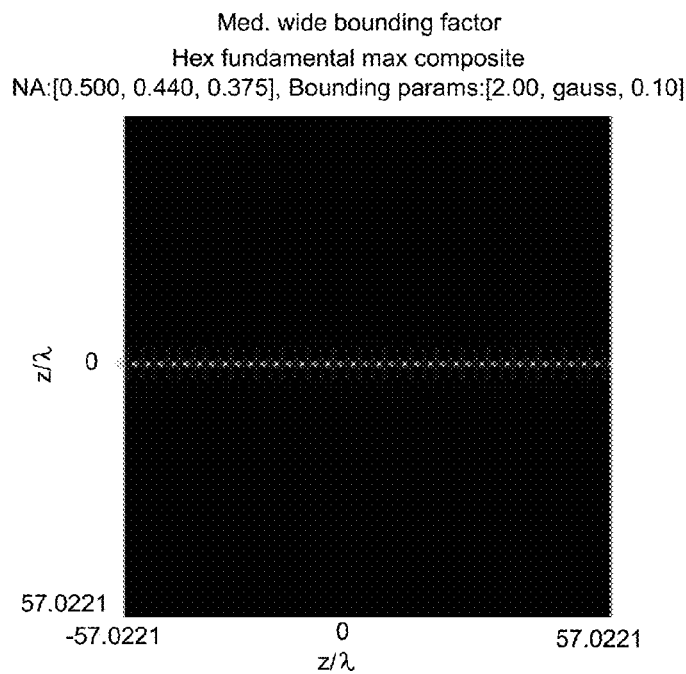
Figure 33D:
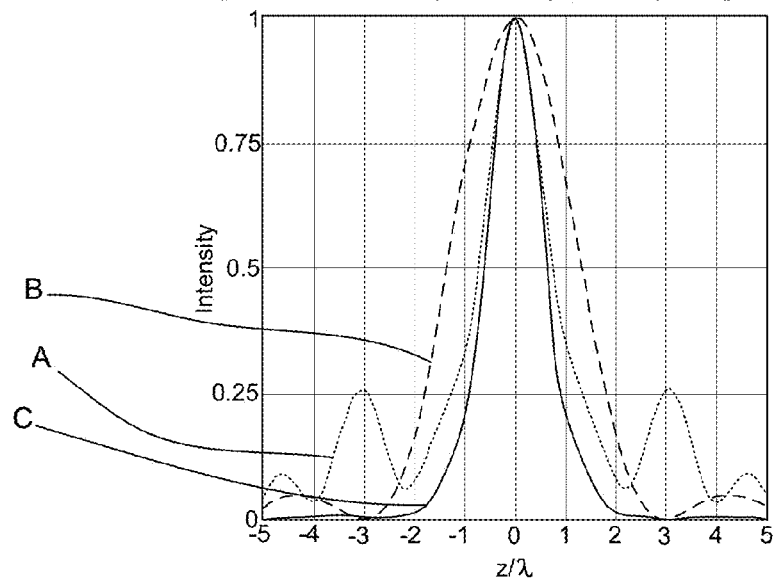
Figure 33E:
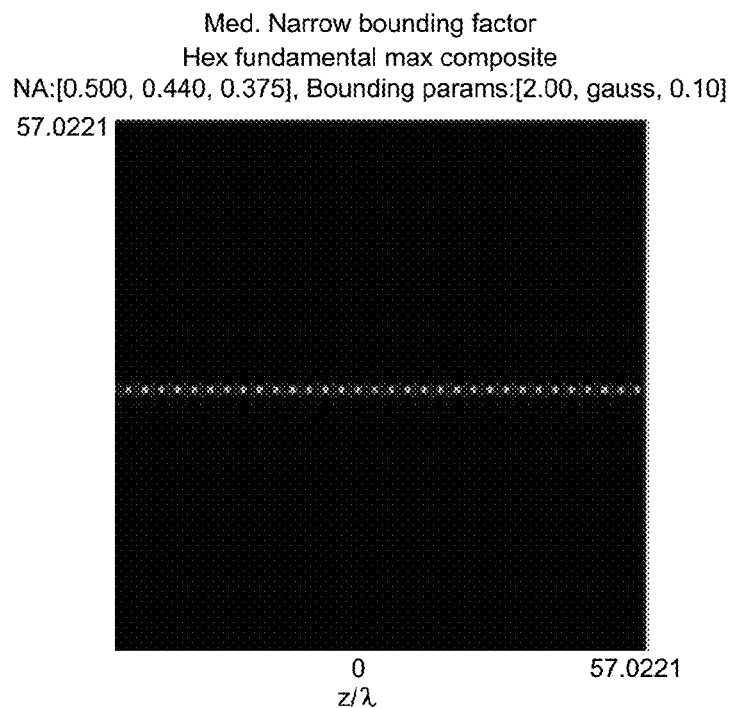
Figure 33F:
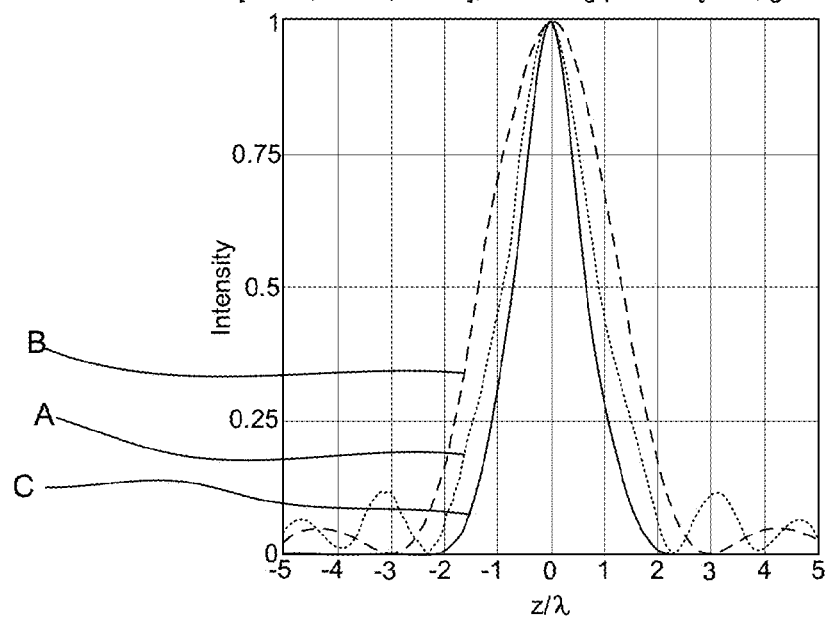
Figure 33G:
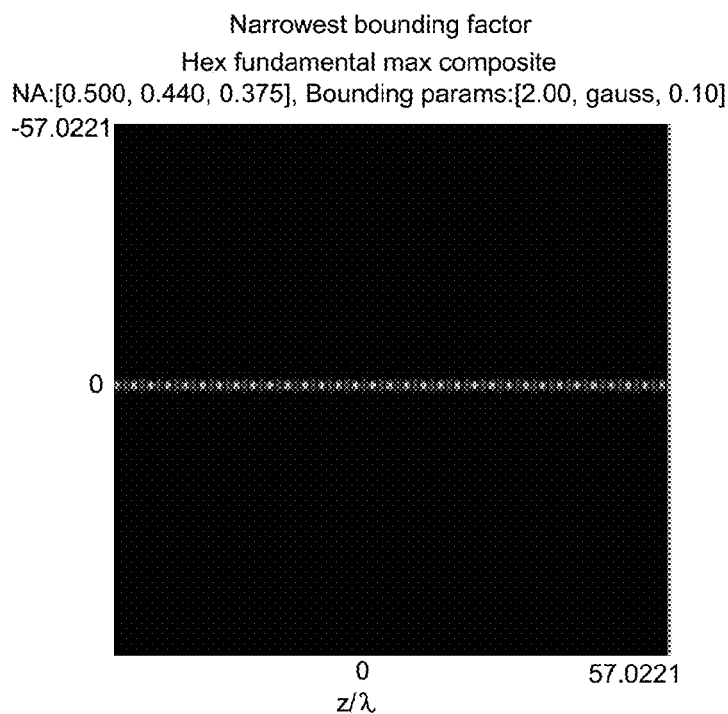
Figure 33H:
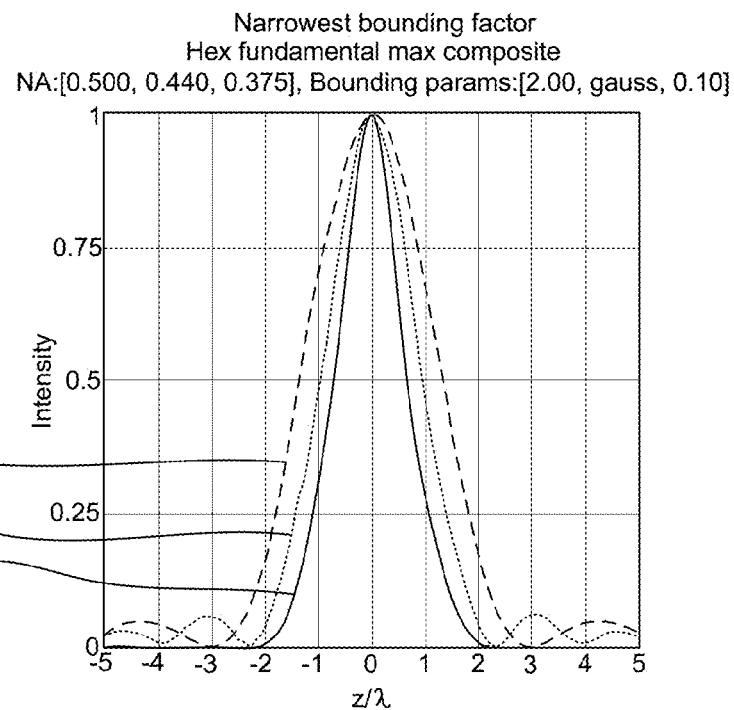

FIG. 33G illustrates the intensity of the optical lattice to which a narrow, or strong, envelope function is applied to the ideal optical lattice pattern. As can be seen in FIG. 33G, intensity maxima exist along the Z=0 plane, but there are no lines of intensity maxima along other planes. Sweeping or dithering this pattern in the X direction creates a light sheet whose intensity profile along the Z direction is shown in curve A of FIG. 33H. Curve A shows much smaller side lobes peaked at three wavelength away rom the Z=0 plane than in FIG. 33B. Curve B shown in FIG. 33H shows the point spread function of the detection objective 2348, and curve C in FIG. 33H shows the normalized product of curves A and B, which is the overall point spread function of the optical system in the Z direction. As can be seen from a comparison of FIG. 33B and FIG. 33H, the central peak in curve A of FIG. 33B is narrower than the central peak in curve A of FIG. 33H, but the side lobes of FIG. 33B are larger than the side lobes and FIG. 33H. Thus, bound optical lattices having different parameters can be selected to image different samples using different techniques. FIG. 33C and FIG. 33D are similar to FIGS. 33A and 33B, respectively, and to FIGS. 33G and 33H, respectively, except that a medium-wide envelope function is used. FIG. 33E and FIG. 33F are similar to FIGS. 33A and 33B, respectively, and to FIGS. 33G and 33H, respectively, except that a medium-narrow envelope function is used.

Implementations of the various techniques described herein may be implemented in digital electronic circuitry, or in computer hardware, firmware, software, or in combinations of them. Implementations may implemented as a computer program product, i.e., a non-transitory computer program tangibly embodied in an information carrier, e.g., in a machine-readable storage device (e.g., a computer-readable medium, a tangible computer-readable medium), for processing by, or to control the operation of, data processing apparatus, e.g., a programmable processor, a computer, or multiple computers. In some implementations, a non-transitory tangible computer-readable storage medium can be configured to store instructions that when executed cause a processor to perform a process. A computer program, such as the computer program(s) described above, can be written in any form of programming language, including compiled or interpreted languages, and can be deployed in any form, including as a stand-alone program or as a module, component, subroutine, or other unit suitable for use in a computing environment. A computer program can be deployed to be processed on one computer or on multiple computers at one site or distributed across multiple sites and interconnected by a communications network.

Method steps may be performed by one or more programmable processors executing a computer program to perform functions by operating on input data and generating output. Method steps also may be performed by, and an apparatus may be implemented as, special purpose logic circuitry, e.g., an FPGA (field programmable gate array) or an ASIC (application-specific integrated circuit).

Processors suitable for the processing of a computer program include, by way of example, both general and special purpose microprocessors, and any one or more processors of any kind of digital computer. Generally, a processor will receive instructions and data from a read-only memory or a random access memory or both. Elements of a computer may include at least one processor for executing instructions and one or more memory devices for storing instructions and data. Generally, a computer also may include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

Implementations may be implemented in a computing system that includes a back-end component, e.g., as a data server, or that includes a middleware component, e.g., an application server, or that includes a front-end component, e.g., a client computer having a graphical user interface or a Web browser through which a user can interact with an implementation, or any combination of such back-end, middleware, or front-end components. Components may be interconnected by any form or medium of digital data communication, e.g., a communication network. Examples of communication networks include a local area network (LAN) and a wide area network (WAN), e.g., the Internet.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the implementations. It should be understood that they have been presented by way of example only, not limitation, and various changes in form and details may be made. Any portion of the apparatus and/or methods described herein may be combined in any combination, except mutually exclusive combinations. The implementations described herein can include various combinations and/or sub-combinations of the functions, components and/or features of the different implementations described.

What is claimed is:

1. A method comprising:
   (a) focusing first excitation light having a first wavelength to a first focus within a sample;
   (b) scanning the first focus within a volume in the sample with one or more scanning optical elements;
   (c) de-scanning, with the one or more scanning optical elements, as the first focus is scanned within the volume, first signal light emitted from the first focus onto a wavefront sensor;
   (d) determining, based on the first signal light that is descanned onto the wavefront sensor, an average aberration created by the volume of the sample of a wavefront of the first excitation light;
   (e) focusing second excitation light having a second wavelength through the objective lens to a second focus within the volume in the sample;
   (e) scanning the second focus within the volume in the sample with the one or more scanning optical elements;
   (f) correcting a wavefront of the second excitation light by an amount according to the determined average aberration while the second focus is scanned within the volume;

(g) imaging second signal light emitted from the sample in response to the second excitation light onto a photosensitive detector as the second focus is scanned within the volume, (h) correcting a wavefront of the second signal light by an amount according to the determined average aberration while the second focus is scanned within the volume;

(i) repeating (a)-(h) for a plurality of different volumes in the sample; and (j) generating an image of the sample based on the detected second signal light from scanned foci within the different volumes.

2. The method of claim 1, wherein the first wavelength is longer than a wavelength of the first signal light and wherein the first wavelength is longer than the second wavelength.

3. The method of claim 1, wherein an optical path between the sample and the photosensitive detector includes a pinhole aperture in an opaque screen, wherein the pinhole is optically conjugate to the volume in the sample.

4. The method of claim 1, wherein correcting the wavefront of the second excitation light includes modulating a beam of the second excitation light by a wavefront modulating element and controlling portions of the wavefront modulating element to impart changes to subportions of the beam to achieve the correction of the wavefront of the second excitation light, and wherein the scanning optical elements and the wavefront modulating element are all optically conjugate to a rear pupil of the objective lens.

5. The method of claim 1, wherein correcting the wavefront of the second excitation light includes reducing a spatial extent of the second focus.

6. The method of claim 1, wherein the first wavelength is greater than 800 nm and wherein a wavelength of the first signal light is less than 800 nm.

7. The method of claim 1, wherein the first signal light emitted from the volume includes light emitted from a volume substantially centered at the first focus and wherein the volume has a spatial extent transverse to the optical axis of the objective lens that is greater than the diffraction-limited resolution of the objective lens.

8. The method of claim 1, wherein determining the average aberration created by the volume of the sample includes determining the aberration based on first signal light that is de-scanned onto the first photosensitive sensor from the volume within the sample that is greater than 2 $\mu m^3$.

9. The method of claim 1, wherein the wavefront sensor includes a direct wavefront sensor.

10. The method of claim 1, wherein the wavefront sensor includes a Shack-Hartmann sensor.

11. A method comprising:
(a) focusing excitation light to a focus within a sample;
(b) scanning the focus within a volume in the sample with one or more scanning optical elements;
(c) de-scanning, with the one or more scanning optical elements, as the focus is scanned within the volume, signal light emitted from the focus onto a wavefront sensor;
(d) determining, based on the signal light that is descanned onto the wavefront sensor, an average aberration created by the volume of the sample of a wavefront of the excitation light;
(e) correcting a wavefront of the excitation light by an amount according to the determined average aberration while the focus is scanned within the volume;
(f) imaging the signal light onto a photosensitive detector as the focus is scanned within the volume;

(g) correcting a wavefront of the imaged signal light by an amount according to the determined average aberration while the focus is scanned within the volume;

(h) repeating (a)-(g) for a plurality of different volumes in the sample; and (j) generating an image of the sample based on the imaged signal light from scanned foci within the different volumes.

12. The method of claim 11,
wherein the determined average aberration is determined for a first subportion of the volume that is scanned, and
wherein the corrected wavefront of the excitation light and the corrected wavefront of the imaged signal light are corrected based on the determined average aberration for the first subportion, when the determined focus is scanned over a second subportion of the volume.

13. The method of claim 12,
wherein the focus is scanned over the first subportion and over the second subportion sequentially.

14. The method of claim 13, wherein the focus is scanned sequentially over at least five subportions, including the first and second subportions.

15. The method of claim 11,
wherein a wavelength of the excitation light is approximately twice as great as a wavelength of the signal light.

16. The method of claim 11, wherein correcting the wavefront of the excitation light includes modulating a beam of the excitation light by a wavefront modulating element and controlling portions of the wavefront modulating element to impart changes to subportions of the beam to achieve the correction of the wavefront of the excitation light, and wherein the scanning optical elements and the wavefront modulating element are all optically conjugate to a rear pupil of the objective lens.

17. The method of claim 11, wherein correcting the wavefront of the excitation light includes reducing a spatial extent of the second focus.

18. The method of claim 11, wherein the wavelength of the excitation light is greater than 800 nm and wherein a wavelength of the signal light is less than 800 nm.

19. The method of claim 11, wherein the signal light emitted from the volume has a spatial extent transverse to the optical axis of the objective lens that is greater than the diffraction-limited resolution of the objective lens.

20. The method of claim 11, wherein determining the average aberration created by the volume of the sample includes determining the aberration based on signal light that is de-scanned onto the wavefront sensor from the volume within the sample that is greater than 2 $\mu m^3$.

21. The method of claim 11, wherein the wavefront sensor includes a direct wavefront sensor.

22. The method of claim 11, wherein the wavefront sensor includes a Shack-Hartmann sensor.

23. A method comprising:
(a) focusing first excitation light with a first objective lens to a first focus within a sample;
(b) scanning the first focus within a volume in the sample with one or more first scanning optical elements;
(c) de-scanning, with the one or more first scanning optical elements, as the first focus is scanned within the volume, first signal light emitted from the first focus onto a wavefront sensor;
(d) determining, based on the first signal light that is descanned onto the wavefront sensor, a first average aberration created by the volume of the sample of a wavefront of the first excitation light;

(e) focusing second excitation light through a second objective lens to a second focus within the volume in the sample;

(f) scanning the second focus within the volume in the sample with the one or more second scanning optical elements;

(g) de-scanning, with the one or more of the second scanning optical elements, as the second focus is scanned within the volume, second signal light emitted from the second focus onto a wavefront sensor;

(h) determining, based on the second signal light that is descanned onto the wavefront sensor, a second average aberration created by the volume of the sample of a wavefront of the second excitation light;

(i) providing third excitation light through the second objective lens to the volume in the sample;

(j) scanning the third excitation light within the volume in the sample with the one or more of the second scanning optical elements;

(k) correcting a wavefront of the third excitation light by an amount according to the determined second average aberration while the third excitation light is scanned within the volume;

(l) imaging, with the first objective lens, third signal light emitted from the sample in response to the third excitation light onto a photosensitive detector as the third excitation light is scanned within the volume, (m) correcting a wavefront of the third signal light by an amount according to the determined first average aberration while the third excitation light is scanned within the volume;

(n) repeating (a)-(m) for a plurality of different volumes in the sample; and (o) generating an image of the sample based on the detected second signal light from scanned foci within the different volumes.

24. The method of claim 23, wherein an optical path between the sample and the photosensitive detector includes a pinhole aperture in an opaque screen, wherein the pinhole is optically conjugate to the volume in the sample.

25. The method of claim 23, wherein correcting the wavefront of the third excitation light includes modulating a beam of the third excitation light by a wavefront modulating element and controlling portions of the wavefront modulating element to impart changes to subportions of the beam to achieve the correction of the wavefront of the third excitation light, and wherein the wavefront modulating element is optically conjugate to the volume of the sample.

26. The method of claim 23, wherein the wavefront sensor onto which the second signal light is de-scanned includes a direct wavefront sensor.

27. The method of claim 26, wherein the wavefront sensor includes a Shack-Hartmann sensor.

28. The method of claim 23, wherein providing the third excitation light includes providing a sheet of excitation light.

29. The method of claim 28, wherein the sheet of excitation light has a maximum thickness of about 3 µm over a distance of about 6 µm long propagation direction of the sheet.

30. The method of claim 28, wherein providing the sheet of excitation light includes providing a plurality of Bessel-like beams arranged substantially in a plane.

31. The method of claim 28, wherein providing the sheet of excitation light includes providing a Gaussian beam of excitation light and sweeping the Gaussian beam in a direction perpendicular to the propagation direction of the beam.

32. The method of claim 28, wherein providing the sheet of excitation radiation includes focusing a Gaussian beam of excitation radiation with a cylindrical lens to create the excitation radiation sheet in the sample.

33. The method of claim 28, wherein providing the sheet of excitation radiation includes providing a Bessel-like beam of excitation radiation and sweeping the Bessel-like beam in a direction perpendicular to a propagation direction of the beam.

34. The method of claim 28, wherein the sheet of excitation radiation includes a plurality of Bessel-like beams arranged substantially in a plane, wherein the plurality of Bessel-like beams partially overlap with neighboring Bessel-like beams in the sample, and wherein the plurality of Bessel-like beams are phase coherent with each other.

35. The method of claim 34, wherein the plurality of Bessel-like beams are spaced from their neighboring beams by distances such that destructive interference between neighboring Bessel-like beams occurs at positions that are not in the plane.

36. The method of claim 35, further comprising controlling relative phases of the different Bessel-like beams.

37. The method of claim 36, wherein the plurality of Bessel-like beams are spaced from their neighboring beams by distances that are less than a diameter of a first side lobe of the Bessel-like beams and wherein controlling the relative phrase of the different Bessel-like beams includes controlling the relative phases such that destructive interference between neighboring Bessel-like beams occurs at positions that are not in the plane.

38. The method of claim 36, wherein controlling the relative phrases of the Bessel-like beams includes reflecting the Bessel-like beams off a wavefront modulating element (WME) and controlling the WME to control the relative phrases.

39. The method of claim 38, wherein the WME includes a spatial light modulator (SLM).

40. An apparatus comprising:
a first source of first excitation light having a first wavelength;
a lens configured to focus the excitation light to a first focus within a sample;
a wavefront sensor;
one or more scanning optical elements configured to scan the first focus within a volume in the sample and configured to de-scan first signal light emitted from the first focus onto the wavefront sensor as the first focus is scanned within the volume;
a wavefront analysis module configured for determining, based on the first signal light that is descanned onto the wavefront sensor, an average aberration created by the volume of the sample of a wavefront of the first excitation light;
a second source of second excitation light having a second wavelength, wherein the lens is configured to focus the second excitation light to a second focus within the volume in the sample, and wherein the one or more scanning optical elements are configured for scanning the second focus within the volume in the sample;
a first wavefront modulating element configured for correcting a wavefront of the second excitation light by an amount according to the determined average aberration while the second focus is scanned within the volume;
a photosensitive detector configured for detecting second signal light emitted from the sample in response to the second excitation light as the second focus is scanned within the volume.

41. The apparatus of claim 40, further comprising one or more processors configured for generating an image of the sample based on the detected second signal light from scanned foci within different volumes of the sample.

42. The apparatus of claim 40, wherein the wavefront modulating element includes a spatial light modulator.

43. The method of claim 40, wherein the wavefront sensor includes a direct wavefront sensor.

44. The method of claim 43, wherein the wavefront sensor includes a Shack-Hartmann sensor.

45. An apparatus comprising:
- a first source of first excitation light;
- a lens configured to focus the excitation light to a first focus within a sample;
- a wavefront sensor;
- one or more scanning optical elements configured to scan the focus within a volume in the sample and to de-scan signal light emitted from the focus onto a wavefront sensor as the focus is scanned within the volume;
- a wavefront analysis module configured for determining, based on the signal light that is descanned onto the wavefront sensor, an average aberration created by the volume of the sample of a wavefront of the excitation light;
- a first wavefront modulating element configured for correcting a wavefront of the excitation light by an amount according to the determined average aberration while the focus is scanned within the volume;
- a photosensitive detector configured for detecting signal light received from the focus in response to the excitation light as the focus is scanned within the volume;
- a second wavefront modulating element configured for correcting a wavefront of the detected signal light by an amount according to the determined average aberration while the focus is scanned within the volume.

46. The apparatus of claim 45, further comprising one or more processors configured for generating an image of the sample based on the detected second signal light from scanned foci within different volumes of the sample.

47. The method of claim 45, wherein the wavefront sensor includes a direct wavefront sensor.

48. The method of claim 45, wherein the wavefront sensor includes a Shack-Hartmann sensor.

* * * * *

UNITED STATES PATENT AND TRADEMARK OFFICE
CERTIFICATE OF CORRECTION

PATENT NO. : 9,500,846 B2
APPLICATION NO. : 14/660906
DATED : November 22, 2016
INVENTOR(S) : Betzig et al.

It is certified that error appears in the above-identified patent and that said Letters Patent is hereby corrected as shown below:

On the Title Page

Item [72], delete "Asbhurn," and insert -- Ashburn, --, therefor.

In the Claims

Column 47, Line 4, Claim 1, delete "volume," and insert -- volume; --, therefor.

Column 49, Line 27, Claim 23, delete "volume," and insert -- volume; --, therefor.

Column 51, Line 7, Claim 43, delete "The method of claim" and insert -- The apparatus of claim --, therefor.

Column 51, Line 9, Claim 44, delete "The method of claim" and insert -- The apparatus of claim --, therefor.

Column 52, Line 18, Claim 47, delete "The method of claim" and insert -- The apparatus of claim --, therefor.

Column 52, Line 20, Claim 48, delete "The method of claim" and insert -- The apparatus of claim --, therefor.

Signed and Sealed this
Twelfth Day of February, 2019

Andrei Iancu
*Director of the United States Patent and Trademark Office*